(12) United States Patent
Vasireddi et al.

(10) Patent No.: US 12,071,418 B2
(45) Date of Patent: Aug. 27, 2024

(54) PROCESSES FOR PREPARATION OF DAPAGLIFLOZIN OR ITS SOLVATES OR CO-CRYSTALS THEREOF

(71) Applicant: LAURUS LABS LIMITED, Hyderabad (IN)

(72) Inventors: Uma Maheswar Rao Vasireddi, Hyderabad (IN); Sanjay Kumar Dehury, Hyderabad (IN); Madana Venkata Sudhakar Gutti, Hyderabad (IN); Krishna Murthy Thopudurthi, Hyderabad (IN)

(73) Assignee: LAURUS LABS LIMITED, Hyderabad (IN)

( * ) Notice: Subject to any disclaimer, the term of this patent is extended or adjusted under 35 U.S.C. 154(b) by 5 days.

(21) Appl. No.: 17/857,497

(22) Filed: Jul. 5, 2022

(65) Prior Publication Data
US 2022/0372010 A1    Nov. 24, 2022

Related U.S. Application Data

(62) Division of application No. 16/323,335, filed as application No. PCT/IB2017/054860 on Aug. 9, 2017, now Pat. No. 11,427,555.

(30) Foreign Application Priority Data

Aug. 9, 2016 (IN) .............................. 201641027121
Apr. 17, 2017 (IN) .............................. 201741013585

(51) Int. Cl.
C07D 309/10     (2006.01)

(52) U.S. Cl.
CPC .................................. *C07D 309/10* (2013.01)

(58) Field of Classification Search
CPC .................................................... C07D 309/10
See application file for complete search history.

(56) References Cited

U.S. PATENT DOCUMENTS

| | | | |
|---|---|---|---|
| 6,936,590 B2 | 8/2005 | Washburn et al. | |
| 2013/0023486 A1 | 1/2013 | Zhao et al. | |
| 2016/0347731 A1 | 12/2016 | Zhu | |
| 2017/0240520 A1 | 8/2017 | Hsiao | |

FOREIGN PATENT DOCUMENTS

| | | |
|---|---|---|
| WO | WO 2010/022313 | 2/2010 |
| WO | WO 2015/101916 | 6/2015 |
| WO | WO 2017/060925 | 4/2017 |

OTHER PUBLICATIONS

Chemical abstracts registry—2009.*
The International Search Report for PCT/IB2017/054860 dated Nov. 12, 2017.
International Search Report provided to the Office on Feb. 5, 2019.

* cited by examiner

*Primary Examiner* — Valerie Rodriguez-Garcia
(74) *Attorney, Agent, or Firm* — Blank Rome LLP

(57) ABSTRACT

The present invention generally relates to an improved process for the preparation of dapagliflozin of Formula I or its solvates or co-crystals thereof. Dapagliflozin is an inhibitor of sodium dependent glucose transporters and used for treating diabetes. The present invention also encompasses novel intermediates and their use in the preparation of dapagliflozin. An exemplary process according to the present is shown below, wherein $X_1$, $R_1$, $R_2$, $P_1$, $P_2$, $P_3$ and $P_4$ are as described herein.

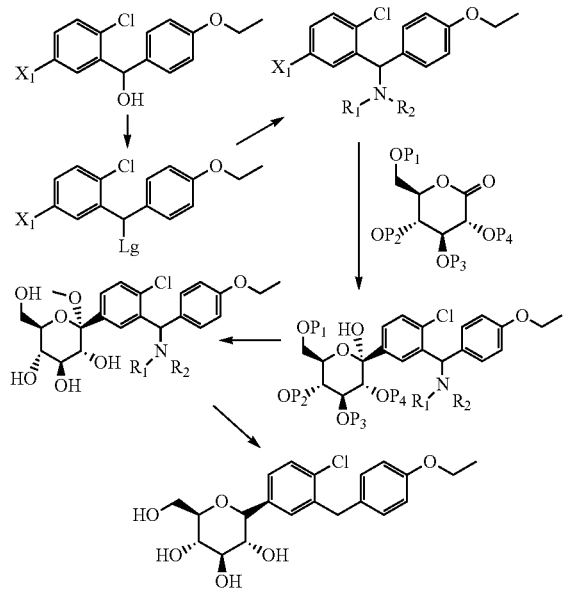

23 Claims, 3 Drawing Sheets

PROCESSES FOR PREPARATION OF DAPAGLIFLOZIN OR ITS SOLVATES OR CO-CRYSTALS THEREOF

CROSS-REFERENCE TO RELATED APPLICATIONS

This is a divisional application of U.S. patent application Ser. No. 16/323,335, filed on Feb. 5, 2019, which is a national stage application that claims the benefit of the filing date and disclose of International Application PCT/IB2017/054860, filed on Aug. 9, 2017, which is related to and claims the benefit of the filing date and disclosure under Indian Provisional Application No(s). 201641027121, filed on Aug. 9, 2016 entitled "Novel process for preparation of Dapagliflozin or its solvates or co-crystals thereof", and 201741013585, filed on Apr. 17, 2017 entitled "Novel process for preparation of Dapagliflozin or its solvates or co-crystals thereof," the content of each of which are incorporated by reference herein.

FIELD OF THE INVENTION

The present invention relates to an improved process for the preparation of dapagliflozin or its solvates or co-crystals thereof. The present invention also encompasses the novel intermediates used therein.

BACKGROUND OF THE INVENTION

Worldwide diabetes has become one of the major causes of death in adults, an increasing number of diabetes patients may sharply with the increase of obesity population. Approximately 100 million people worldwide suffer from type II diabetes (NIDDM—non-insulin-dependent diabetes mellitus), which is characterized by hyperglycemia due to excessive hepatic glucose production and peripheral insulin resistance, the root causes for which are as yet unknown. Hyperglycemia is considered to be the major risk factor for the development of diabetic complications, and is likely to contribute directly to the impairment of insulin secretion seen in advanced NIDDM. Normalization of plasma glucose in NIDDM patients would be predicted to improve insulin action, and to offset the development of diabetic complications. An inhibitor of the sodium-dependent glucose transporter SGLT2 in the kidney would be expected to aid in the normalization of plasma glucose levels, and perhaps body weight, by enhancing glucose excretion.

Dapagliflozin is an inhibitor of sodium dependent glucose transporters and used for treating diabetes, especially type II diabetes, as well as hyperglycemia, hyperinsulinemia, obesity, hypertriglyceridemia, Syndrome X, diabetic complications, atherosclerosis and related diseases, employing such C-aryl glucosides alone or in combination with one, two or more other type antidiabetic agent and/or one, two or more other type therapeutic agents such as hypolipidemic agents.

Dapagliflozin is chemically designated as (1S)-1,5-anhydro-1-C-[4-chloro-3-[(4-ethoxyphenyl) methyl] phenyl]-D-glucitol and approved as (2S)-1,2-propane-diol monohydrate under the brand name FARXIGA for the treatment of type 2 diabetes mellitus. It was developed by Bristol-Myers Squibb in partnership with AstraZeneca. The structural Formula of dapagliflozin (2S)-1,2-propanediol is represented as follows:

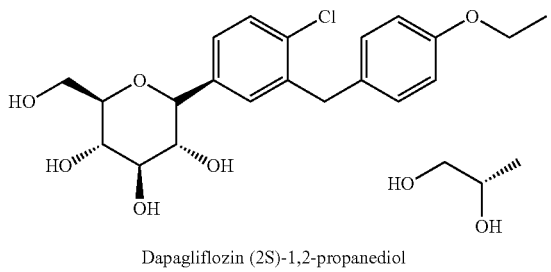

Dapagliflozin (2S)-1,2-propanediol

Dapagliflozin and its process for the preparation were first disclosed in U.S. Pat. No. 6,515,117 ("the '117 patent") and the disclosed processes of dapagliflozin involves the preparation of halogenated benzene derivative of Formula III by reaction of 5-bromo-2-chlorobenzoyl chloride with phenetole thereby isolating 5-bromo-2-chloro-4'-ethoxybenzophenone, which upon reduction in acetonitrile at 50° C. gives 4-bromo-1-chloro-2-(4-ethoxybenzyl)benzene of Formula III, coupling of TMS protected gluconolactone of Formula IV with halogenated benzene derivative of Formula III in presence of n-butyl lithium followed by methane sulfonic acid solution in presence of methanol to obtain O-methylglucoside intermediate of Formula V. By the reduction of resulting O-methylglucoside intermediate of Formula V with triethylsilane and boron trifluoride gives crude dapagliflozin, which upon purification by first converting it into tetra acetylated dapagliflozin of Formula VI followed by hydrolysis with lithium hydroxide gives pure dapagliflozin as an amorphous glassy off-white solid with purity 94%. The process disclosed in the '117 patent is schematically represented as follows:

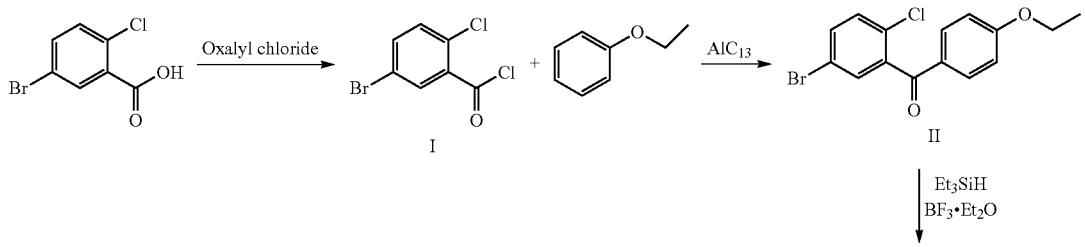

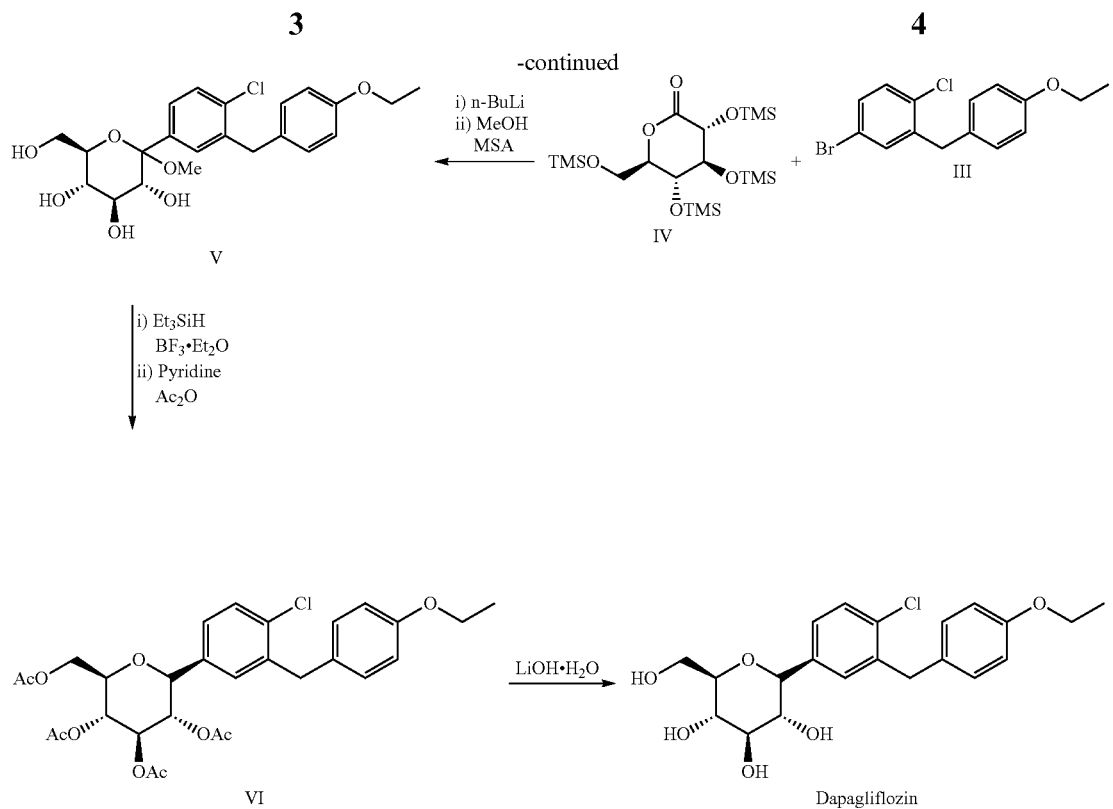

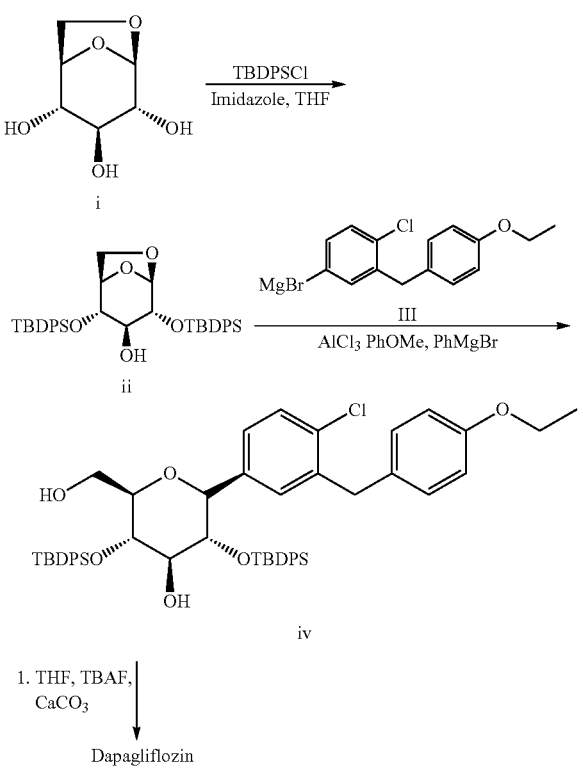

The Dapagliflozin obtained by U.S. '117 involves multiple, time consuming process steps which involves getting intermediate products as oily residue at various stages of the process, which is difficult to purify and handle for further process step. More over the workup involves multiple evaporation of solvent containing product which may result in product decomposition. Another draw back of the process is that the crude dapagliflozin obtained after reduction of O-methyl glucoside is a mixture of α and β anomers, which requires purification by acylation of crude Dapagliflozin using acetic anhydride results in desired tetraacetylated β-glucoside as white solid and the undesired α-glucoside remains in mother liquor followed by neutralization of desired tetraacetylated β-glucoside and finally recrystallization of the product with methylene chloride. The process requires multiple steps, multiple solvents for removal of α-anomer makes the process not viable for large scale manufacturing.

U.S. Pat. No. 7,375,213 ("the '213 patent") disclosed the similar product patent route to prepare dapagliflozin by coupling of gluconolactone with halogenated benzene derivative to obtain hydroxyl glucoside intermediate as solid, later glycosidation of —OH group to —OMe and simultaneous removal of acid-labile groups of glucoside moiety to yield above compound of Formula V.

U.S. Pat. No. 8,952,139 ("the '139 patent") disclosed an alternate process for preparation of dapagliflozin by coupling of 1,6-anhydro-β-D-glucopyranose compound of Formula (ii) with halogenated benzene derivative of Formula III to yield compound of Formula (iv) followed by converting compound of Formula (iv) to dapagliflozin. The process disclosed in the '139 patent is schematically represented as follows:

Organic Letters, 2012, vol, 14, No. 6, 1480-1483, disclosed the coupling of halogenated benzene derivative with 2,3,4,6-Tetra-O-Pivaloyl-β-D-Glucopyranosyl bromide in presence of Zinc reagent.

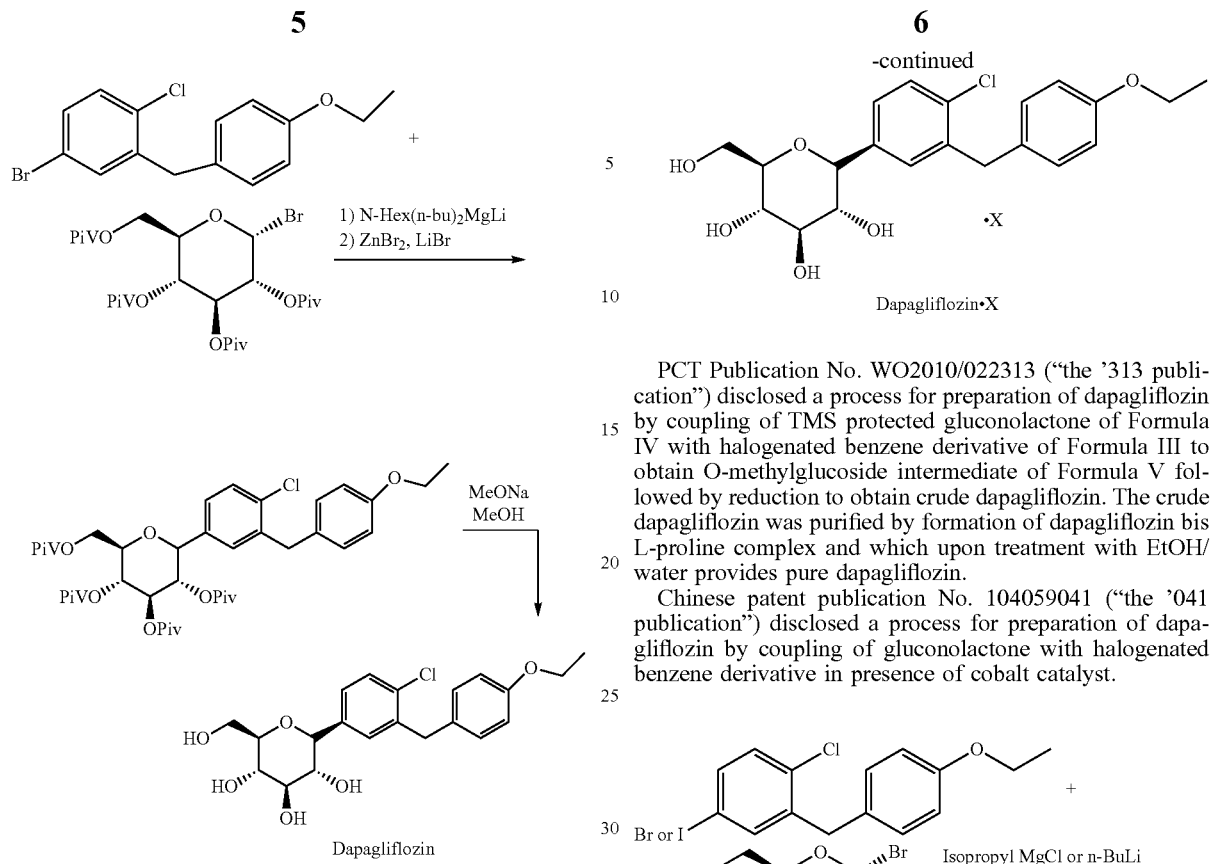

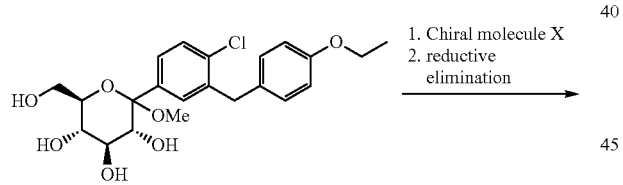

Chinese patent publication No. 102167715 ("the '715 publication") disclosed one pot method for the preparation of dapagliflozin co-crystals by reaction of O-methylglucoside with chiral molecule followed by selective removal of methoxy group with a reducing agent.

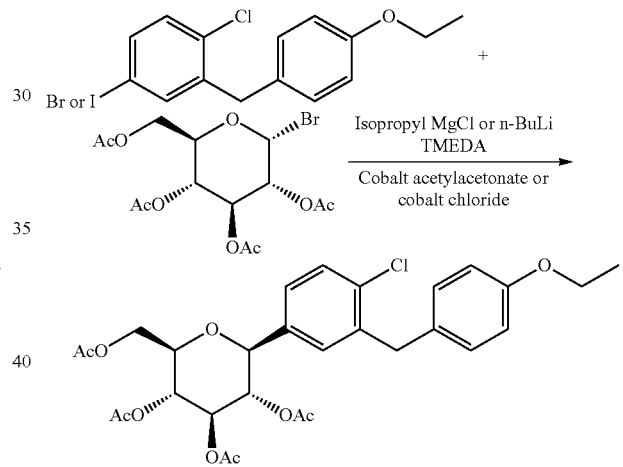

PCT Publication No. WO2010/022313 ("the '313 publication") disclosed a process for preparation of dapagliflozin by coupling of TMS protected gluconolactone of Formula IV with halogenated benzene derivative of Formula III to obtain O-methylglucoside intermediate of Formula V followed by reduction to obtain crude dapagliflozin. The crude dapagliflozin was purified by formation of dapagliflozin bis L-proline complex and which upon treatment with EtOH/water provides pure dapagliflozin.

Chinese patent publication No. 104059041 ("the '041 publication") disclosed a process for preparation of dapagliflozin by coupling of gluconolactone with halogenated benzene derivative in presence of cobalt catalyst.

Chinese patent publication No. 104529970 ("the '970 publication") disclosed the preparation of dapagliflozin by the following scheme:

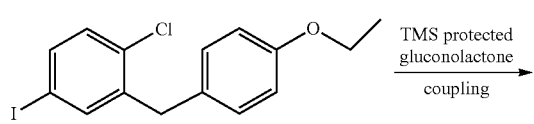

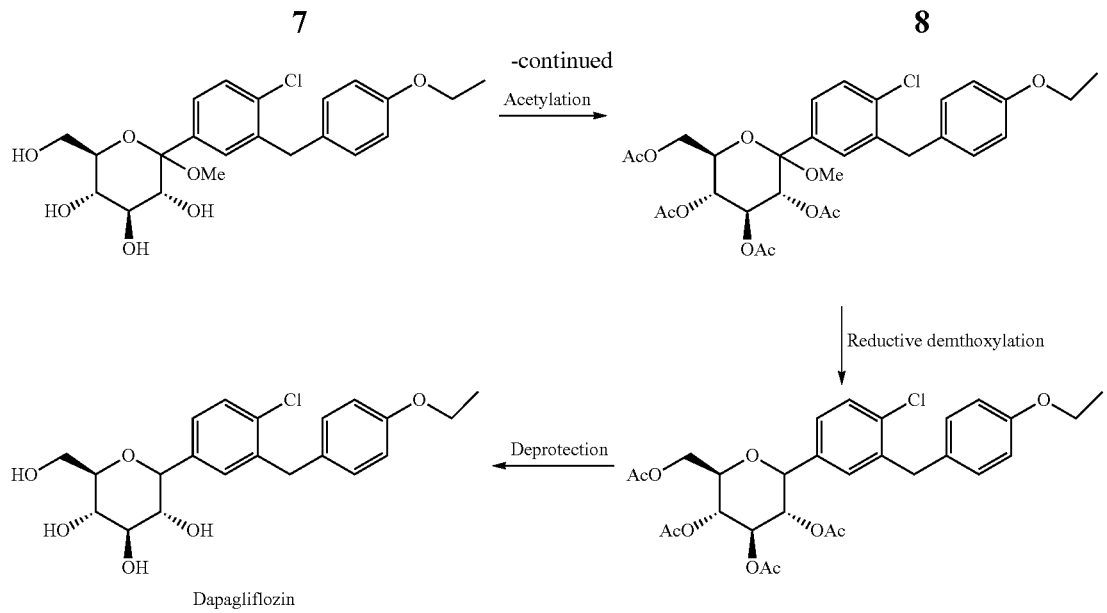
Chinese patent publication No. 104710486 ("the '486 publication") disclosed the preparation of dapagliflozin by coupling of TMS protected gluconolactone with halogenated benzene compound to obtain hydroxyl glucoside intermediate, which on later hydroxyl group reduction to obtain crude dapagliflozin. The crude dapagliflozin was purified via the acetylation.
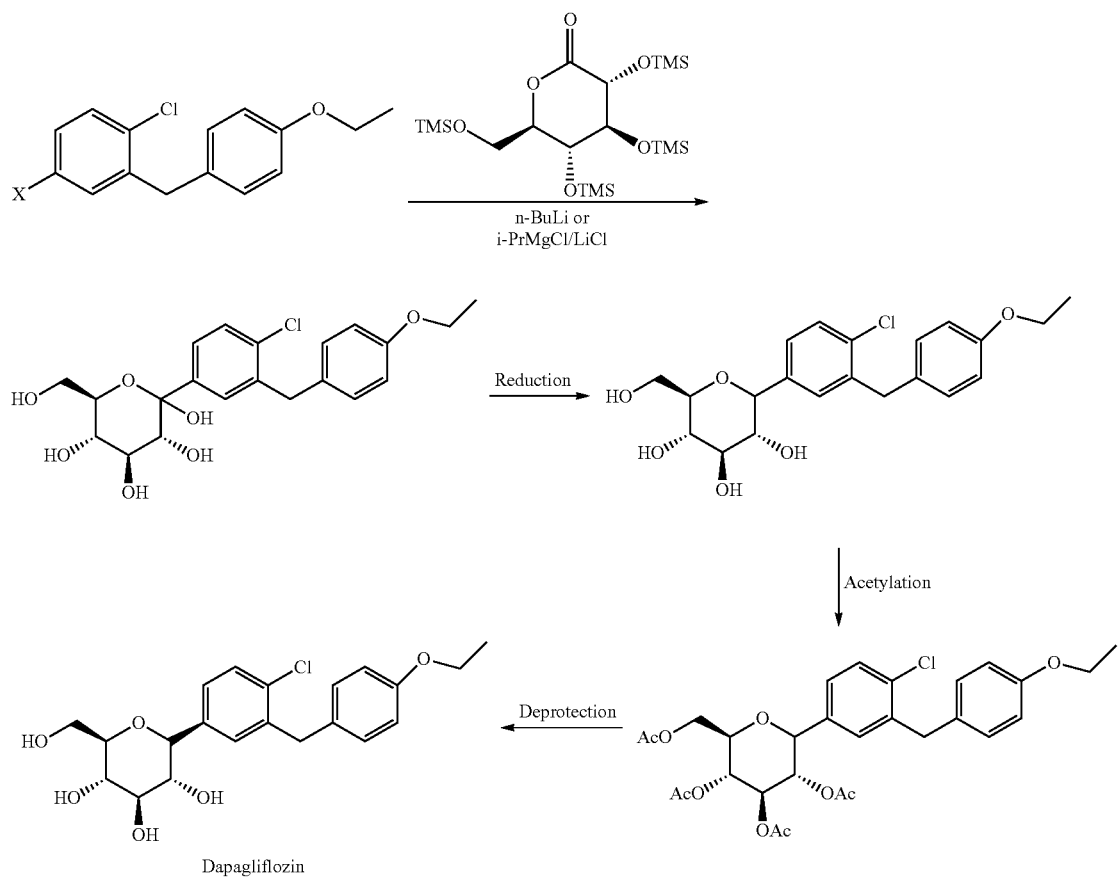

PCT Publication No. WO2015/155739 ("the '739 publication") disclosed a process for preparation of dapagliflozin by coupling of 1,6-anhydro-β-D-glucopyranose aluminium mixture with halogenated benzene aluminium mixture to obtain dapagliflozin.

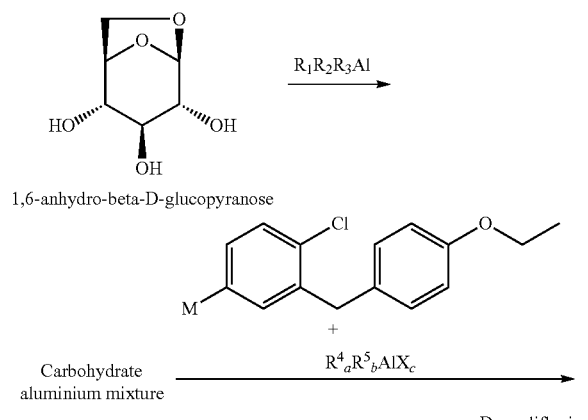

Chinese patent publication No. 105294624 ("the '624 publication") disclosed the preparation of dapagliflozin by coupling sulfonoylated glucone moiety with halogenated benzene compound in presence of Grignard reagent and Lewis acid to get tetra acetyl dapagliflozin and finally deacetylation of acetyl groups provides dapagliflozin.

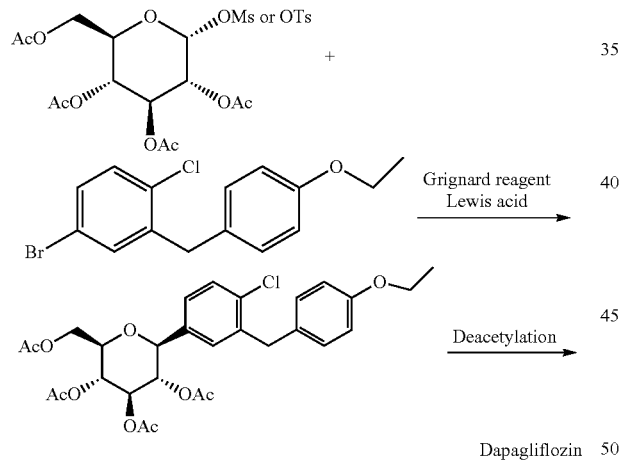

PCT Publication No. WO 2015/132803 ("the '803 publication") disclosed a process for preparation of dapagliflozin by deacetylation of tetraacetyl dapagliflozin using mild bases along with the formation of glycerol solvate results yield high pure dapagliflozin.

PCT Publication No. WO 2015/0040571 ("the '571 publication") disclosed the preparation of dapagliflozin by deacetylation of tetra acetyl protected dapagliflozin in the presence of an amine base.

PCT Publication No. WO 2015/044849 ("the '313 publication") disclosed the purification of dapagliflozin by acetylation of dapagliflozin with acetic anhydride in the absence of pyridine as solvent followed by deacetylation.

Chinese patent publication No. 104496952 ("the '912 publication") disclosed the coupling of halogenated benzene derivative with 2,3,4,6,-tetraacetoxy-α-D-glucopyranose bromide in presence of copper or grignard reagent at below −10° C.

Chinese patent publication No. 104961715 ("the '715 publication") disclosed the preparation of dapagliflozin by reduction of TMS protected hydroxyl glucoside compound by using hydroboron and sulfuric acid.

Chinese patent publication No. 105481915 ("the '915 publication") disclosed the preparation of Dapagliflozin by protection of hydroxyl groups of compound of Formula A to give compound of Formula B, coupling of compound of Formula B with halogenated benzene compound followed by deprotection of hydroxyl groups and finally removing —OMe group provides dapagliflozin.

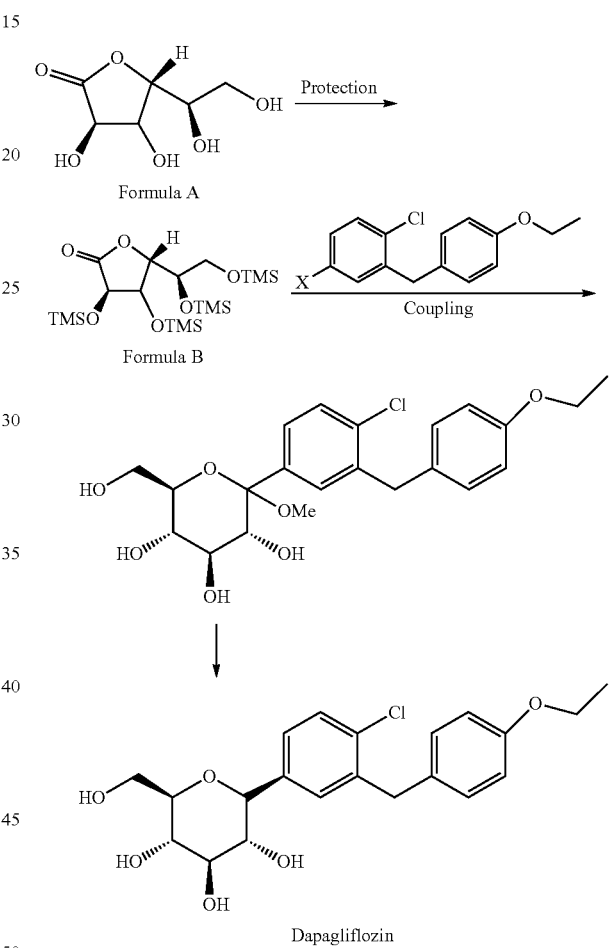

PCT Publication No. WO2016/147197 ("the '197 publication") disclosed the preparation of Dapagliflozin by coupling sulfonoylated glucone moiety with halogenated benzene compound, glycosidation of OH group of the resulting compound with alcohols such as allyl alcohol, isopropyl alcohol or propargyl alcohol results yield allyl, isopropyl or propargyl glucoside intermediate of Formula V. By the reduction of resulting intermediate of Formula V with triethylsilane and boron trifluoride gives Dapagliflozin.

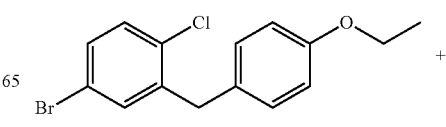

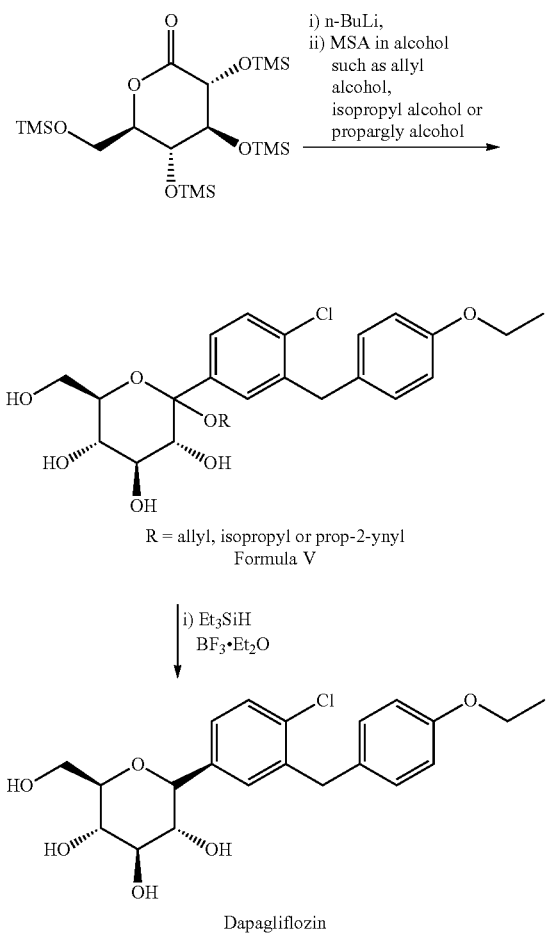

R = allyl, isopropyl or prop-2-ynyl
Formula V

Dapagliflozin

Other patent publication No(s) WO2015/063726, IN3942/CHE/2010, CN103570510A, CN104086379B and CN104478670A disclosed the preparation dapagliflozin intermediate of 4-halo-1-chloro-2-(4-ethoxybenzyl)benzene.

Our co-pending Indian Patent application IN201641010442 ("the '442 Application) disclosed co-crystals of dapagliflozin, wherein the co-crystal former is selected from the group comprising DL-pipecolic acid, D-pipecolic acid, L-pipecolic acid, ammonia, nicotinic acid, isonicotinic acid, pyridine, pyrazine-2-carboxylic acid, imidazole, morpholine, proline and the like.

Though existence of various processes for the preparation of dapagliflozin and its intermediates, there remains a need for an alternative processes for the preparation of dapagliflozin producing high yields and purity, which is suitable for an industrial scale.

Thus the present invention provides a novel process for the preparation of dapagliflozin of Formula I or its solvates or co-crystals thereof by using novel intermediates.

SUMMARY OF THE INVENTION

In accordance with one embodiment, the present invention provides a process for preparation of dapagliflozin of Formula I or its solvates or co-crystals thereof.

In accordance with another embodiment, the present invention provides a process for preparation of dapagliflozin of Formula I or its co-crystals thereof,

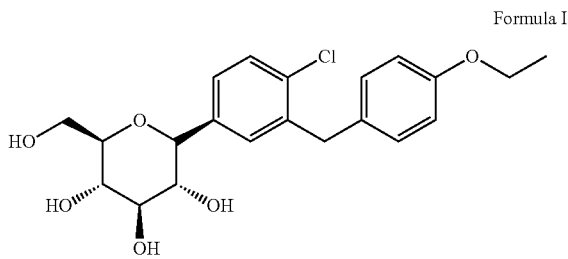

Formula I comprising:
a) reacting a compound of Formula VIa; wherein "P" represents hydrogen or a suitable hydroxyl protecting group and $X_1$ represents a suitable leaving group;

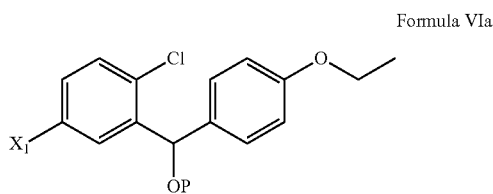

Formula VIa with glucono lactone of Formula VIII to obtain a compound of Formula IX, wherein $P_1$, $P_2$, $P_3$ and $P_4$ independently represents hydrogen or a suitable hydroxyl protecting group;

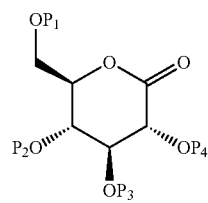

Formula VIII

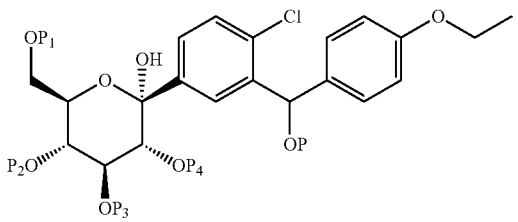

Formula IX b) converting the compound of Formula IX to a compound of Formula XI, wherein $R_1$ represents a hydrogen or an alkyl group; and Formula XI

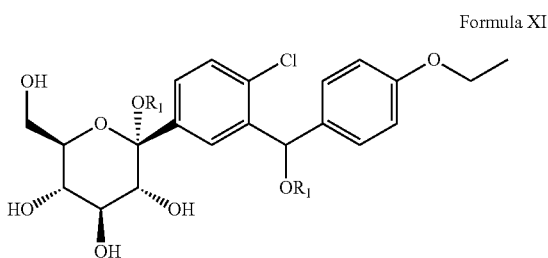

c) reducing the compound of Formula XI with a suitable reducing agent to obtain dapagliflozin of Formula I.

In accordance with another embodiment, the present invention provides a process for preparation of dapagliflozin of Formula I or its co-crystals thereof, Formula I

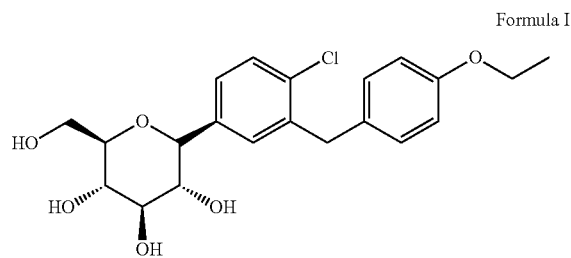

comprising:
a) reacting an aldehyde compound of Formula IV with a compound of Formula V, wherein $X_1$ and $X_2$ independently represents a suitable leaving group; to obtain a compound of Formula VI, wherein "$X_1$" represents a suitable leaving group;

Formula IV

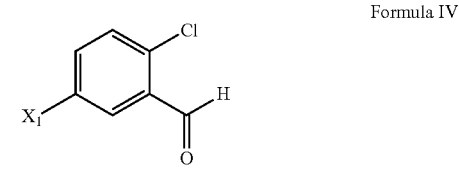

Formula V

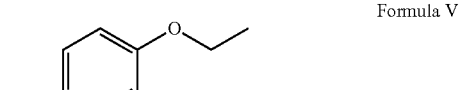

Formula VI

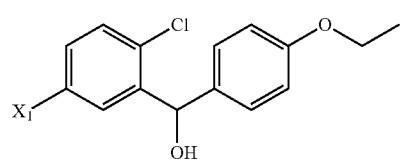

b) optionally protecting the hydroxyl group of compound of Formula VI to obtain a compound of Formula VIa, wherein "$X_1$" is same as defined above and P represents hydrogen or a suitable hydroxyl protecting group;

Formula VIa

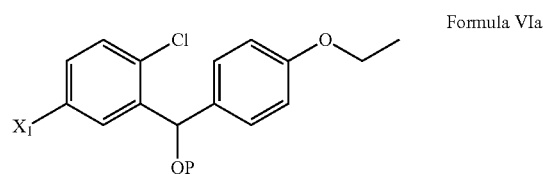

c) reacting the compound of Formula VIa with glucono lactone of Formula VIII to obtain a compound of Formula IX, wherein P, $P_1$, $P_2$, $P_3$ and $P_4$ independently represents hydrogen or a suitable hydroxyl protecting group;

Formula VIII

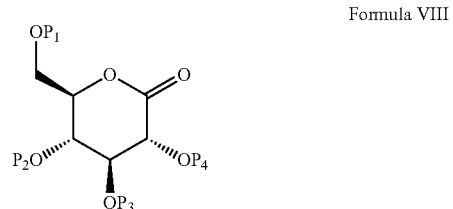

Formula IX

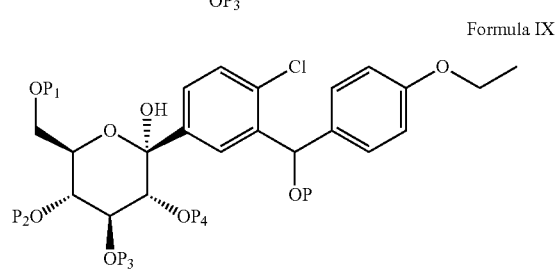

d) converting the compound of Formula IX to a compound of Formula XI, wherein $R_1$ represents a hydrogen or an alkyl group; and Formula XI

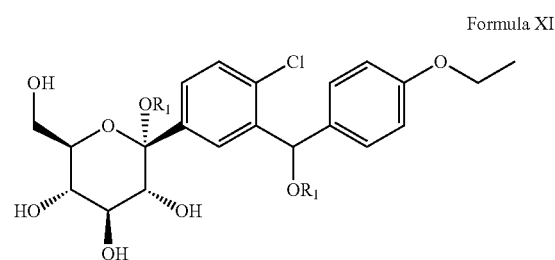

e) reducing the compound of Formula XI with a suitable reducing agent to obtain dapagliflozin of Formula I.

In accordance with another embodiment, the present invention provides a process for preparation of dapagliflozin of Formula I or its solvates or co-crystals thereof, comprising:
a) protecting a hydroxyl group of compound of Formula VI to obtain a compound of Formula VIa, wherein "$X_1$" represents a suitable leaving group and P represents a suitable hydroxyl protecting group;
b) condensing the compound of Formula VIa with glucono lactone of Formula VIII to obtain a compound of Formula IX, wherein P, $P_1$, $P_2$, $P_3$ and $P_4$ independently represents hydrogen or a suitable hydroxyl protecting group;

c) converting the compound of Formula IX to a compound of Formula XI, wherein $R_1$ represents a hydrogen or an alkyl group; and
d) reducing the compound of Formula XI with a suitable reducing agent to obtain dapagliflozin of Formula I.

In accordance with another embodiment, the present invention provides a process for preparation of dapagliflozin of Formula I or its solvates or co-crystals thereof, comprising:
a) converting a compound of Formula IX to a compound of Formula XI, wherein P, $P_1$, $P_2$, $P_3$, $P_4$ independently represents hydrogen or a suitable hydroxyl protecting group and $R_1$ represents a hydrogen or an alkyl group; and
b) reducing the compound of Formula XI with a suitable reducing agent to obtain dapagliflozin of Formula I.

In accordance with another embodiment, the present invention provides a process for the preparation of dapagliflozin of Formula I or its solvates or co-crystals thereof, comprising: reducing a compound of Formula XI with a suitable reducing agent to obtain dapagliflozin of Formula I, wherein $R_1$ represents hydrogen or an alkyl group.

In accordance with another embodiment, the present invention provides a process for preparation of dapagliflozin of Formula I or its solvates or co-crystals thereof, comprising:
a) protecting a hydroxyl group of compound of Formula VI to obtain a compound of Formula VIa, wherein "$X_1$" represents a suitable leaving group and P represents a suitable hydroxyl protecting group; and
b) converting the compound of Formula VIa into dapagliflozin of Formula I.

In accordance with another embodiment, the present invention provides a process for preparation of dapagliflozin of Formula I or its solvates or co-crystals thereof, comprising:
a) reacting a compound of Formula VIa with glucono lactone of Formula VIII to obtain a compound of Formula IX wherein P, $P_1$, $P_2$, $P_3$ and $P_4$ independently represents hydrogen or a suitable hydroxyl protecting group; and
b) converting the compound of Formula IX into dapagliflozin of Formula I.

In accordance with another embodiment, the present invention provides a compound of Formula VIa:

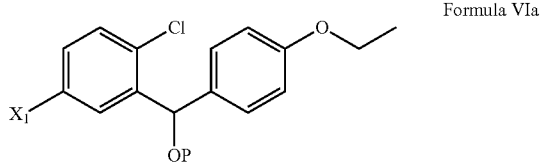

Formula VIa wherein "$X_1$" represents a suitable leaving group and P represents a suitable hydroxyl protecting group.

In accordance with another embodiment, the present invention provides a compound of Formula VIa:

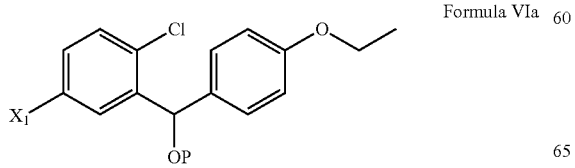

Formula VIa wherein "$X_1$" represents a suitable leaving group, which is selected form the group consisting of fluoro, chloro, bromo or iodo and the like and P represents a suitable hydroxyl protecting, which is selected from the group consisting of alkyl, allyl, pivaloyl, acetyl (Ac), tosyl (Ts), mesyl (Ms), trimethylsilyl (TMS), triethylsilyl (TES), triisopropylsilyl (TIPS), tertiary butyldimethylsilyl (TBS), benzyl (Bn), para-methoxybenzyl (PMB), trityl (Tr), para-bromobenzoyl, para-nitrobenzoyl, benzoyl (Bz), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like.

In accordance with another embodiment, the present invention provides a compound of Formula VIa1, Formula VIa2 or Formula VIa3.

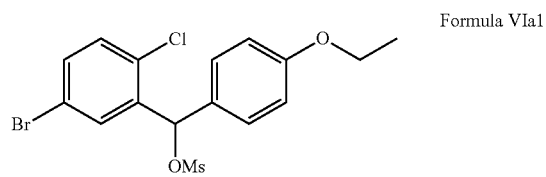

Formula VIa1

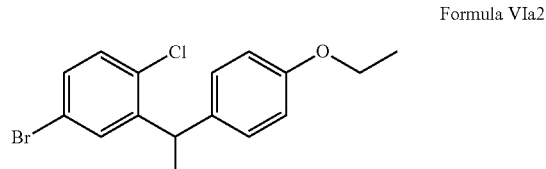

Formula VIa2

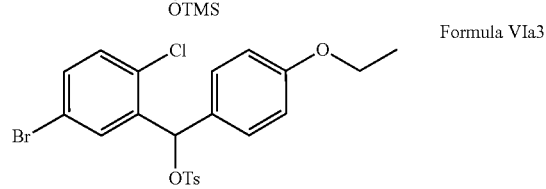

Formula VIa3

In accordance with another embodiment, the present invention provides a process for preparation of a compound of Formula VIa, comprising:

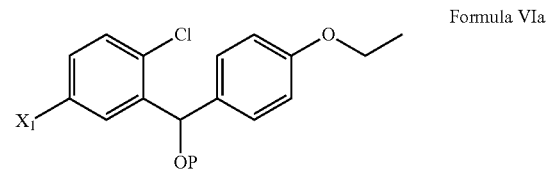

Formula VIa wherein "$X_1$" represents a suitable leaving group and P represents a suitable protecting group;
a) reacting an aldehyde compound of Formula IV with a compound of Formula V, wherein $X_1$ and $X_2$ independently represents a suitable leaving group; to obtain a compound of Formula VI, wherein "$X_1$" represents a suitable leaving group; and
b) protecting the hydroxyl group of compound of Formula VI with a suitable hydroxyl protecting group to obtain a compound of Formula VIa, wherein "$X_1$" is same as defined above and P represents a suitable hydroxyl protecting group.

In accordance with another embodiment, the present invention provides a compound of Formula IX:

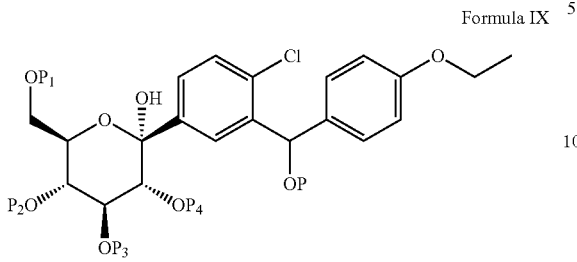

Formula IX wherein P, $P_1$, $P_2$, $P_3$ and $P_4$ represents hydrogen or a suitable hydroxyl protecting group.

In accordance with another embodiment, the present invention provides a compound of Formula IX:

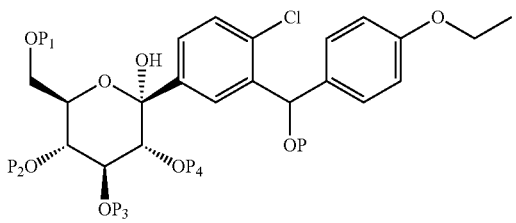

Formula IX wherein P, $P_1$, $P_2$, $P_3$ and $P_4$ independently represents hydrogen or a suitable hydroxyl protecting group, wherein the hydroxyl protecting groups are selected from the group consisting of alkyl, allyl, pivaloyl, acetyl (Ac), tosyl, mesyl, trimethylsilyl (TMS), triethylsilyl (TES), triisopropylsilyl (TIPS), tertiary butyldimethylsilyl (TBS), 2-(trimethylsilyl)ethoxymethyl (SEM), benzyl (Bn), para-methoxybenzyl (PMB), trityl (Tr), para-bromobenzoyl, para-nitrobenzoyl, benzoyl (Bz), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), and the like. Further, the protecting groups for hydroxyl groups may form acetal or silyl acetal together with adjacent hydroxyl groups.

In accordance with another embodiment, the present invention provides a compound of Formula IXa1, Formula IXa2 or Formula IXa3.

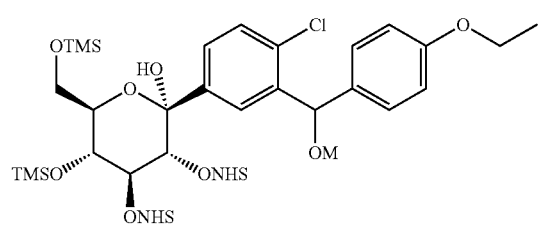

Formula IXa1

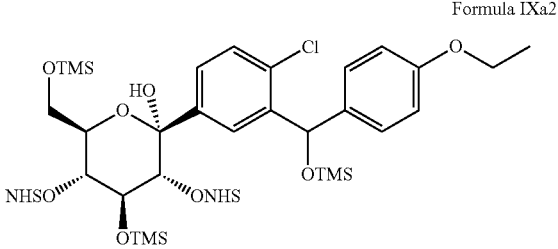

Formula IXa2

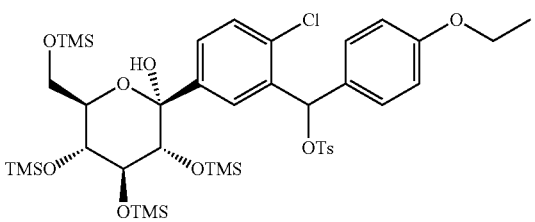

Formula IXa3

In accordance with another embodiment, the present invention provides a compound of Formula XI.

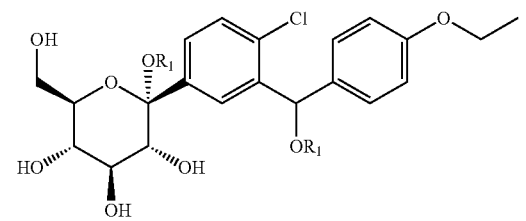

Formula XI wherein $R_1$ represents hydrogen or a $C_{1-12}$ alkly group.

In accordance with another embodiment, the present invention provides a compound of Formula XIa, Formula XIb, Formula XIc or Formula XId.

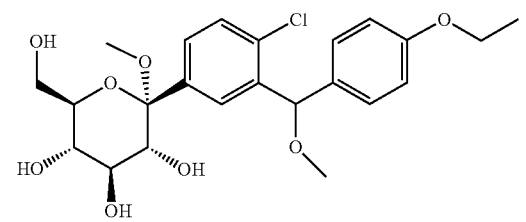

Formula XIa

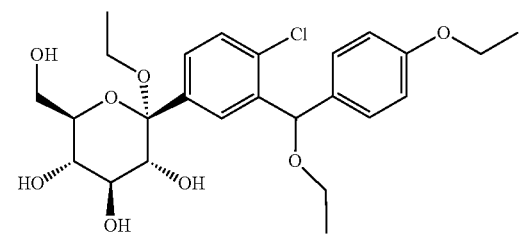

Formula XIb

-continued

Formula XIc

Formula XId

In accordance with another embodiment, the present invention provides a process for preparation of a compound of Formula XI, comprising: converting a compound of Formula IX to a compound of Formula XI, wherein P, $P_1$, $P_2$, $P_3$, $P_4$ independently represents hydrogen or a suitable hydroxyl protecting group and $R_1$ represents a hydrogen or an alkyl group;

Formula IX

Formula XI

In accordance with another embodiment, the present invention provides a process for purification of a compound of Formula XI, comprising:
i) dissolving a compound of Formula XI in one or more solvents,
ii) adding an antisolvent to the step a) solution or vice-versa, and
iii) filtering the pure compound of Formula XI;
wherein the one or more solvents are selected from the group consisting ethers, esters, aromatic hydrocarbons, halogenated hydrocarbons and the like and mixtures thereof, wherein the antisolvent is selected from the group consisting of water, aliphatic or cyclic hydrocarbons and mixtures thereof.

In accordance with another embodiment, the present invention provides a process for the preparation of dapagliflozin of Formula I or its solvates or co-crystals thereof, Formula I comprising:
a) protecting a hydroxyl group of compound of Formula VI-I with trimethyl silyl chloride to obtain a compound of Formula VIa2;

Formula VI-I

Formula VIa2 b) reacting the compound of Formula VIa2 with tetrakis-2,3,4,4-tetra-O-trimetylsilyl-β-D-glucono lactone of Formula VIIIa to obtain compound of Formula IXa2;

Formula IXa2 c) glycosidating the compound of Formula IXa2 with a suitable acid in the presence of methanol to obtain a compound of Formula XIa; and Formula XIa

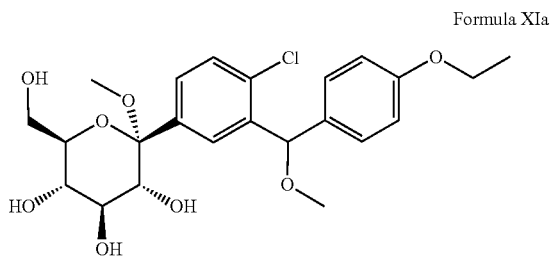 [SMILES: CCOc1ccc(C(OC)c2cc([C@]3(OC)O[C@H](CO)[C@@H](O)[C@H](O)[C@H]3O)ccc2Cl)cc1]

Formula VIII

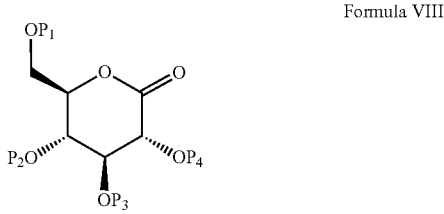

d) reducing the compound of Formula XIa with a suitable reducing agent to obtain dapagliflozin of Formula I.

In accordance with another embodiment, the present invention provides a process for preparation of dapagliflozin of Formula I or its solvates or co-crystals thereof;

Formula IX'

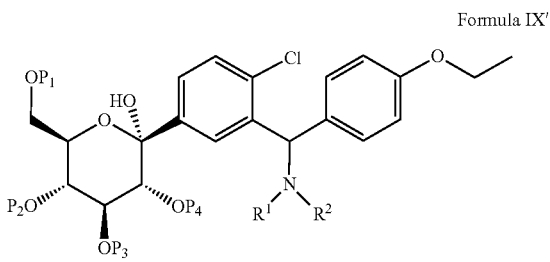

Formula I

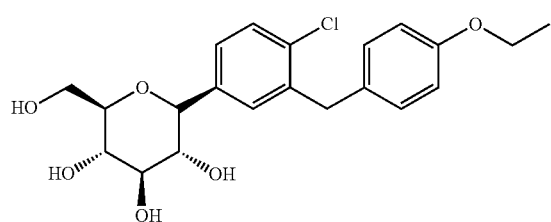

c) converting the compound of Formula IX' to a compound of Formula XI'; wherein $P_1$, $P_2$, $P_3$, $P_4$, $R^1$ and $R^2$ are same as defined above; and Formula XI'

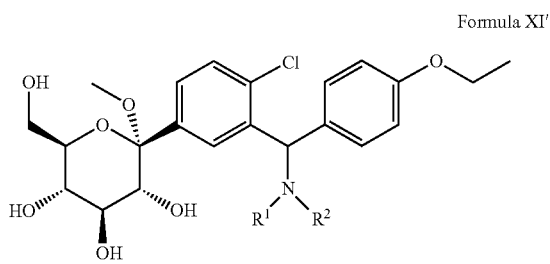

comprising:
a) reacting a compound of Formula VI or a reactive derivative thereof with a suitable amine source to obtain a compound of Formula VII;

d) reducing the compound of Formula XI' with a suitable reducing agent to obtain dapagliflozin of Formula I.

In accordance with another embodiment, the present invention provides a compound of Formula VII;

Formula VI

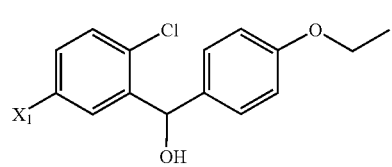

Formula VII

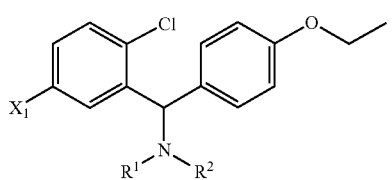

Formula VII

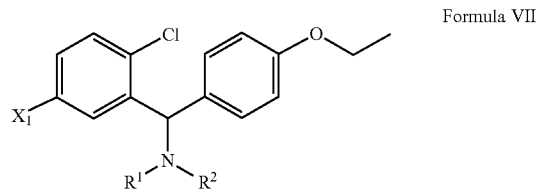

wherein "$X_1$" represents a suitable leaving group and $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring;

b) reacting the compound of Formula VII with glucono lactone of Formula VIII to obtain a compound of Formula IX'; wherein $R^1$ & $R^2$ are same as defined above and $P_1$, $P_2$, $P_3$ and $P_4$ independently represents a suitable hydroxyl protecting group;

wherein "$X_1$" represents a suitable leaving group and $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring.

In accordance with another embodiment, a compound of Formula VII includes, but are not limited to a compound of Formula VIIa, VIIb, VIIc, VIId or VIIe;

Formula VIIa
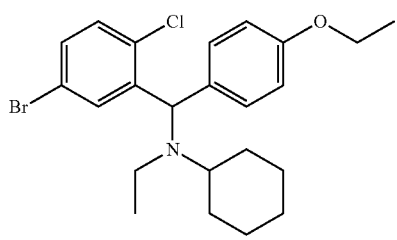

Formula VIIb
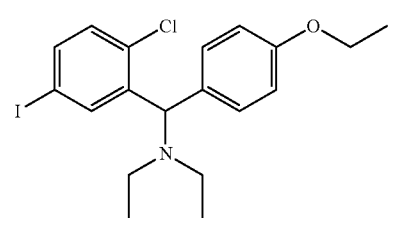

Formula VIIc
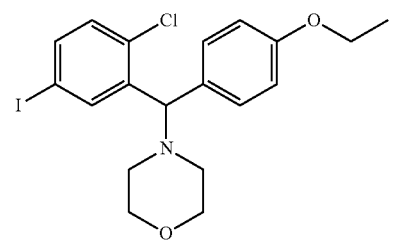

Formula VIId
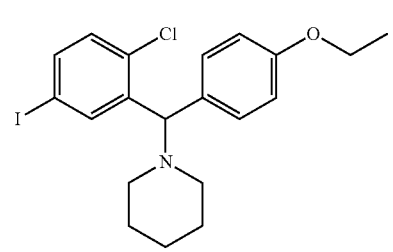

Formula VIIe
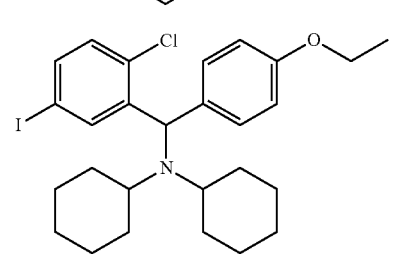

In accordance with another embodiment, the present invention provides a compound of Formula IX';

Formula IX'
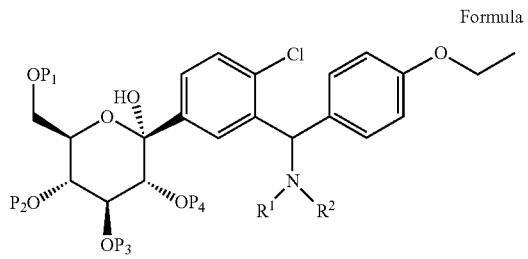

wherein "$X_1$" represents a suitable leaving group and $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring; and $P_1$, $P_2$, $P_3$, $P_4$ represents a suitable hydroxyl protecting group.

In accordance with another embodiment a compound of Formula IX' includes, but is not limited to a compound of Formula IX'a, IX'b, IX'c or IX'd;

Formula IX'a
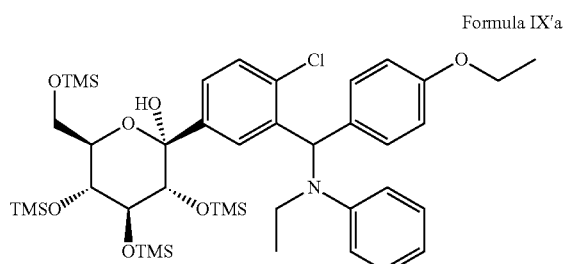

Formula IX'b
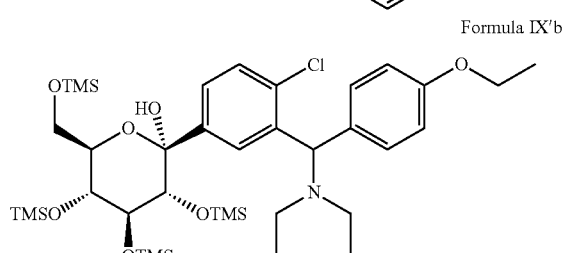

Formula IX'c
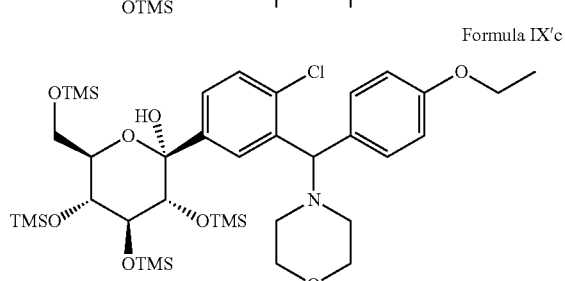

Formula IX'd
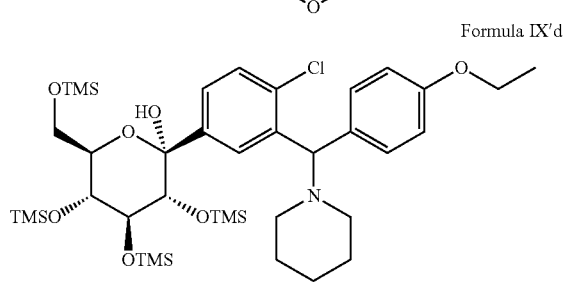

In accordance with another embodiment, the present invention provides a compound of Formula X';

Formula X'
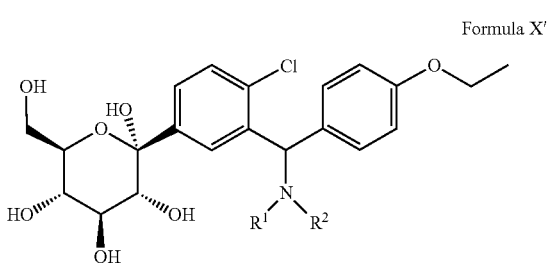

wherein $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring.

In accordance with another embodiment, a compound of Formula X' includes, but are not limited to a compound of Formula X'a, X'b, X'c or X'd;

Formula X'a
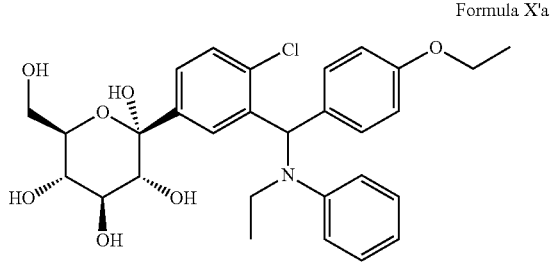

Formula X'b
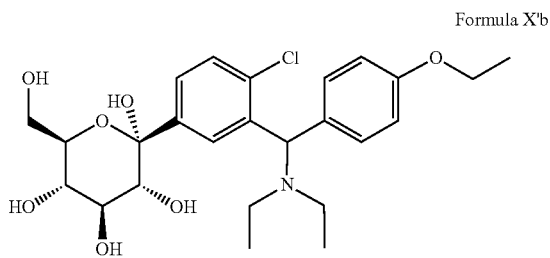

Formula X'c
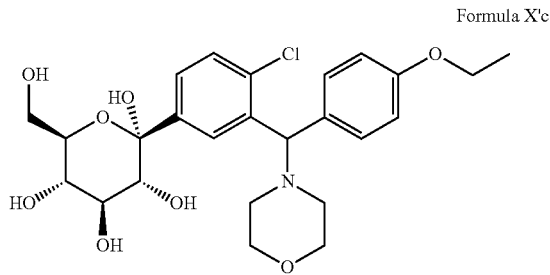

Formula X'd
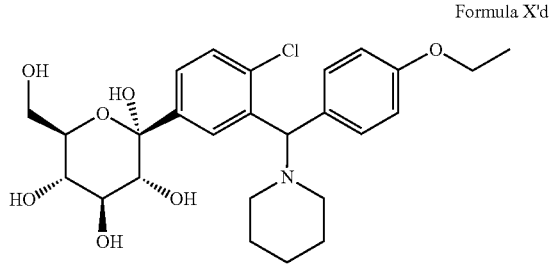

In accordance with another embodiment, the present invention provides a compound of Formula XI';

Formula XI'
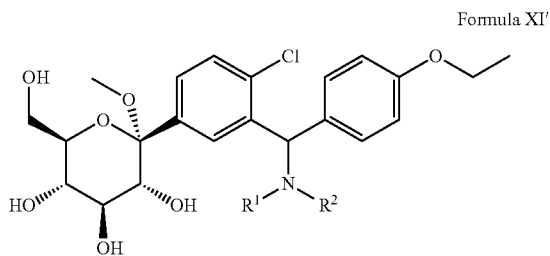

wherein $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring.

In accordance with another embodiment, a compound of Formula XI' includes, but are not limited to a compound of Formula XI'a, XI'b, XI'c or XI'd;

Formula XI'a
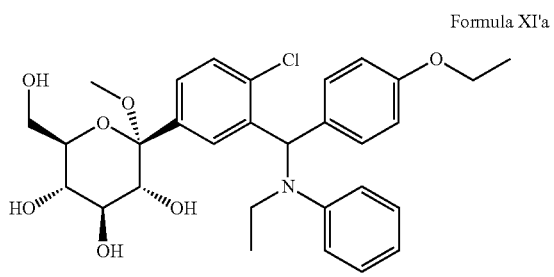

Formula XI'b
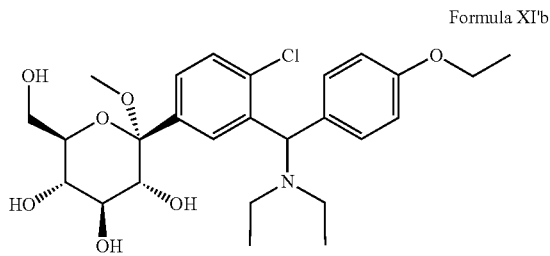

Formula XI'c
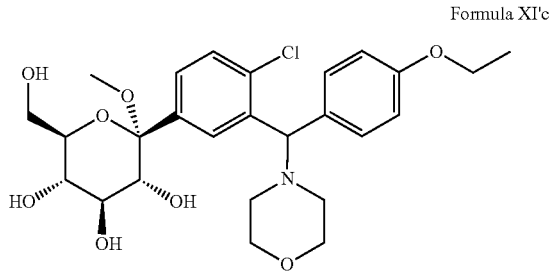

-continued

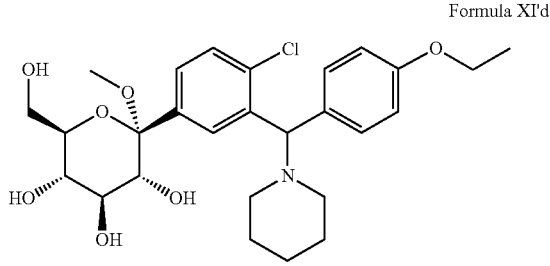

Formula XI'd

In accordance with another embodiment, the present invention provides a process for the preparation of dapagliflozin using one or more of the novel intermediates of Formula VIa, VII, IX, IX', X, X', XI and/or XI' In accordance with another embodiment, the present invention provides a process for the preparation of dapagliflozin of Formula I or its solvates or co-crystals thereof,

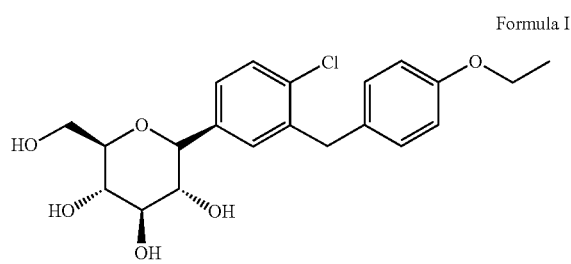

Formula I comprising:
a) converting a compound of Formula VI-I into its mesylate compound of Formula VIa1;

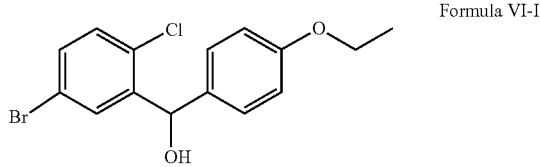

Formula VI-I

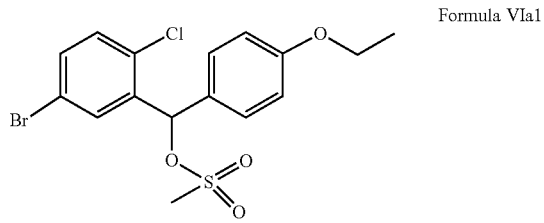

Formula VIa1 b) reacting the compound of Formula VIa1 with N-ethyl-N-phenyl amine to obtain compound of Formula VIIa;

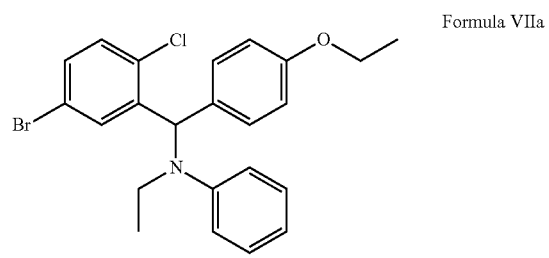 [SMILES: CCOc1ccc(C(c2cc(Br)ccc2Cl)N(CC)c2ccccc2)cc1]

Formula VIIa c) condensing the compound of Formula VIIa with tetrakis-2,3,4,4-tetra-O-trimetylsilyl-β-D-glucono lactone to obtain compound of Formula IX'a;

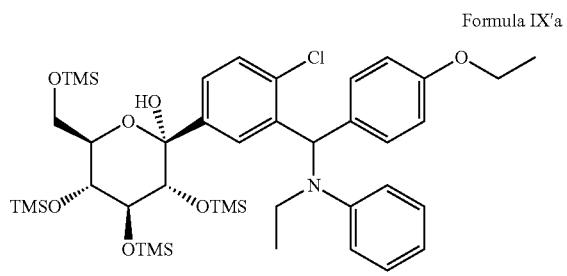

Formula IX'a d) glycosidating the compound of Formula IX'a with a suitable acid to obtain a compound of Formula XI'a; and

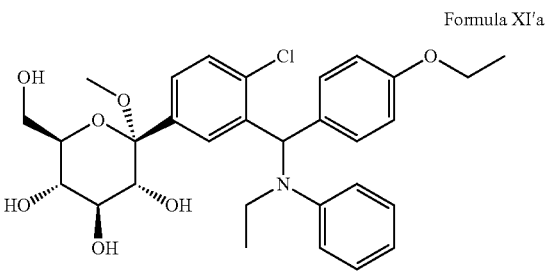 [SMILES: CCOc1ccc(C(c2cc([C@]3(OC)O[C@H](CO)[C@@H](O)[C@H](O)[C@H]3O)ccc2Cl)N(CC)c2ccccc2)cc1]

Formula XI'a e) reducing the compound of Formula XI' with a suitable reducing agent to obtain dapagliflozin of Formula I.

In accordance with another embodiment, the present invention provides a purification process of dapagliflozin of Formula I, comprising:
a) providing a solution of dapagliflozin in one or more organic solvents,
b) adding co-crystal former to the step a) solution,
c) isolating the dapagliflozin co-crystals,
d) converting the dapagliflozin co-crystals into dapagliflozin of Formula I, and
e) isolating the pure dapagliflozin of Formula I; wherein the suitable co-crystal former is selected from the group comprising: DL-pipecolic acid, D-pipecolic acid, L-pipecolic acid, ammonia, nicotinic acid, pyrazine-2-carboxylic acid, imidazole, morpholine and the like.

In accordance with another embodiment, the present invention provides a process for the preparation of dapagliflozin of Formula I or its solvates or co-crystals thereof, comprising:

i) reacting benzoic acid of Formula II with N,O-dimethyl hydroxyl amine or a salt thereof to obtain amide compound of Formula III, wherein "X₁" represents a suitable leaving group;

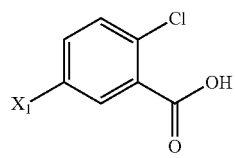

Formula II

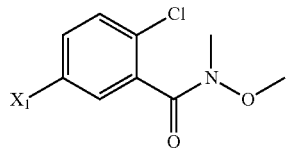

Formula III ii) reducing the compound of Formula III with a suitable reducing agent to obtain an aldehyde compound of Formula IV, wherein "X₁" represents a suitable leaving group;

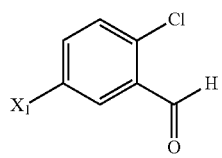

Formula IV iii) reacting the aldehyde compound of Formula IV with a compound of Formula V, wherein X₁ and X₂ independently represents a suitable leaving group;

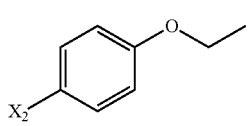

Formula V to obtain a compound of Formula VI, wherein "X₁" represents a suitable leaving group; and

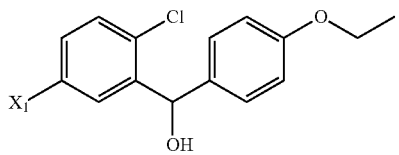

Formula VI iv) converting the compound of Formula VI into dapagliflozin of Formula I.

In accordance with another embodiment, the present invention provides a process for the preparation of dapagliflozin of Formula I or its solvates or co-crystals thereof, comprising:
a) reacting an aldehyde compound of Formula IV with a compound of Formula V to obtain a compound of Formula VI, wherein X₁ and X₂ independently represents a suitable leaving group; and
b) converting the compound of Formula VI into dapagliflozin of Formula I.

In accordance with another embodiment, the present invention provides a process for the preparation of dapagliflozin of Formula I or its solvates or co-crystals thereof, comprising: converting a compound of Formula VI into dapagliflozin of Formula I or its solvates or co-crystals thereof; wherein "X₁" represents a suitable leaving group.

In accordance with another embodiment, the present invention provides a process for the purification of a compound of Formula VI, comprising:
i) dissolving a compound of Formula VI in a suitable solvent,
ii) optionally adding an antisolvent to the step a) solution,
iii) cooling the solution to precipitation, and
iv) filtering the pure compound of Formula VI; wherein the suitable solvent is selected from the group consisting of alcohols, aromatic hydrocarbons, aliphatic or cyclic hydrocarbons and mixtures thereof.

In accordance with another embodiment, the present invention provides a process for the preparation of dapagliflozin of Formula I or its solvates or co-crystals thereof having less than about 10 ppm of desethyl dapagliflozin of Formula XII, less than about 0.15% of a compound of Formula XIII and a compound of Formula XIV, comprising: reacting aldehyde compound of Formula IV with a compound of Formula V to obtain compound of Formula VI and converting the compound of Formula VI in to dapagliflozin of Formula I; wherein the compound of Formula V comprises less than about 10 ppm of desethyl compound of Formula Va and/or less than 0.15% by weight of one or more compounds of Formula Vb, compounds of Formula Vc, compounds of Formula Vd and compounds of Formula Ve.

In accordance with another embodiment, the present invention provides a process for the preparation of dapagliflozin of Formula I having less than about 10 ppm of desethyl dapagliflozin of Formula XII; comprising:
a) reacting an aldehyde compound of Formula IV with a compound of Formula V to obtain a compound of Formula VI, wherein X₁ and X₂ independently represents a suitable leaving group; and
b) converting the compound of Formula VI into dapagliflozin of Formula I; wherein the compound of Formula V having less than about 10 ppm of desethyl compound of Formula Va.

In accordance with another embodiment, the present invention provides dapagliflozin of Formula I or its solvates or co-crystals thereof having a total purity of greater than 99.50%, as measured by HPLC.

In accordance with another embodiment, the present invention provides compound of Formula VI-I having less than 0.200 as measured by HPLC of one or more of impurities of Formula B, Formula C or Formula D:

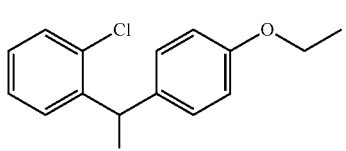

Formula B

Desbromo impurity

-continued

Formula C

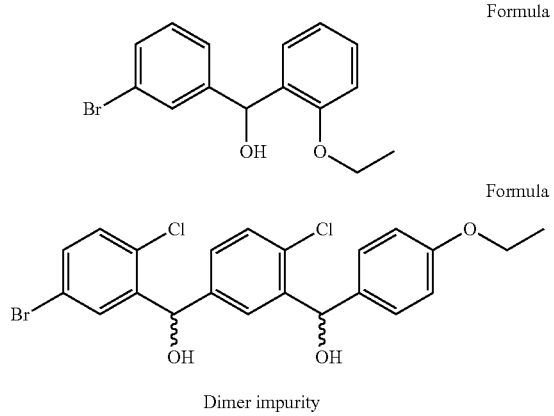

Formula D

Dimer impurity

In accordance with another embodiment, the present invention provides dapagliflozin of Formula I substantially free of one or more of following compounds:

Formula B

Desbromo impurity

Formula C

Formula D

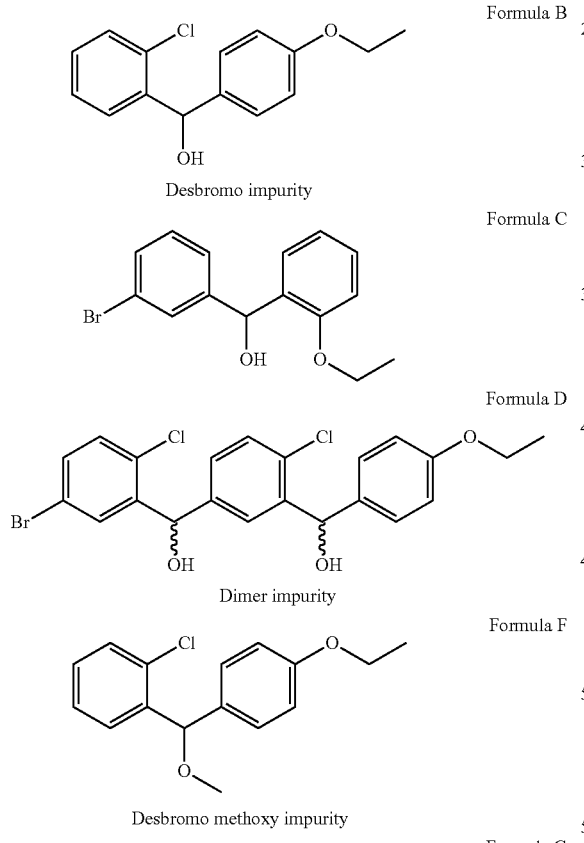

Dimer impurity

Formula F

Desbromo methoxy impurity

Formula G

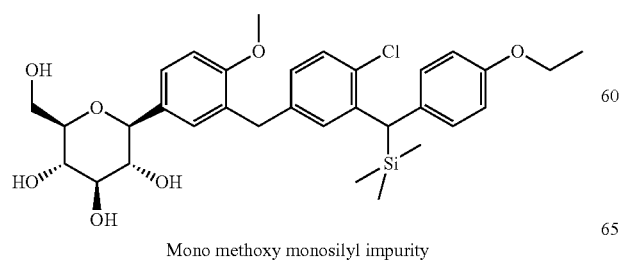

Mono methoxy monosilyl impurity

Formula J

Dimer impurity

In accordance with another embodiment, the present invention provides dapagliflozin of Formula I or its solvates or co-crystals thereof contains less than 0.1% of α-anomer impurity of Formula H as determined by HPLC.

In accordance with another embodiment, the present invention provides dapagliflozin of Formula I or its solvates or co-crystals thereof contains less than 0.1% of dimer impurity of Formula J as determined by HPLC.

In accordance with another embodiment, the present invention provides dapagliflozin of Formula I or its solvates or co-crystals thereof containing less than 0.3%, as measured by HPLC of total impurities of Formula H and Formula J.

In accordance with another embodiment, the present invention provides a compound of Formula B;

Formula B

Desbromo impurity

In accordance with another embodiment, the present invention provides a compound of Formula C;

Formula C

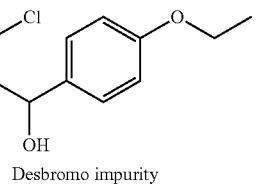

In accordance with another embodiment, the present invention provides a compound of Formula D;

Formula D

Dimer impurity

In accordance with another embodiment, the present invention provides a compound of Formula F;

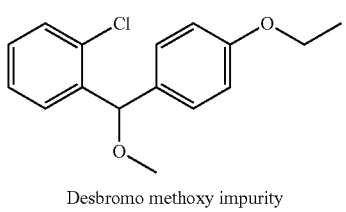

Desbromo methoxy impurity

In accordance with another embodiment, the present invention provides a compound of Formula G;

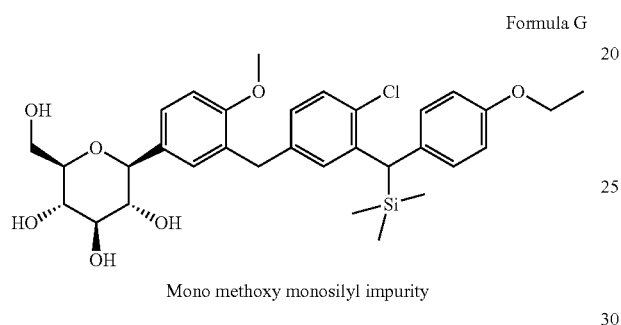

Mono methoxy monosilyl impurity

In accordance with another embodiment, the present invention provides a compound of Formula J;

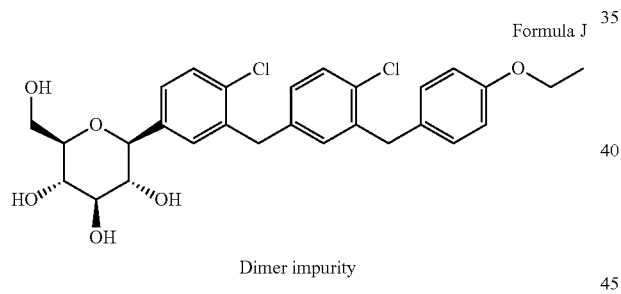

Dimer impurity

In accordance with another embodiment, the present invention provides a pharmaceutical composition comprising dapagliflozin or its solvates or co-crystals thereof prepared by the processes of the present invention and at least one pharmaceutically acceptable excipient.

DETAILED DESCRIPTION OF THE INVENTION

Figure 1:
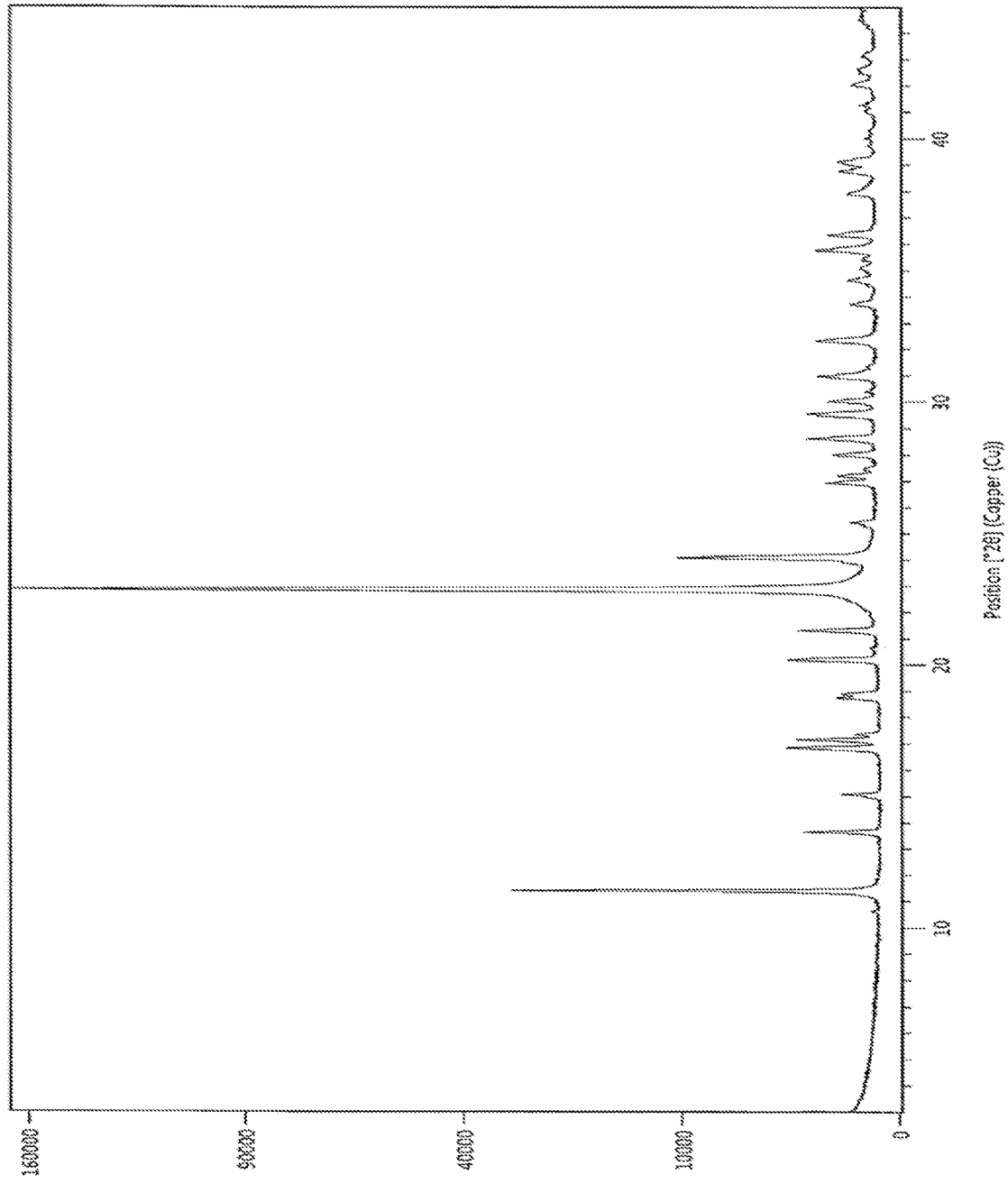
FIG. 01 is the PXRD spectrum of compound of Formula VI-I

The present invention provides a process for the preparation of dapagliflozin of Formula I or its solvates or co-crystals thereof by using novel intermediates.

In one embodiment, the present invention provides a process for preparation of dapagliflozin of Formula I or its co-crystals thereof;

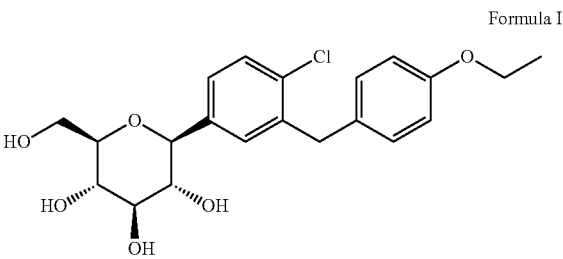 [SMILES: CCOc1ccc(Cc2cc([C@@H]3O[C@H](CO)[C@@H](O)[C@H](O)[C@H]3O)ccc2Cl)cc1]

comprising:
a) reacting a compound of Formula VIa with glucono lactone of Formula VIII to obtain a compound of Formula IX

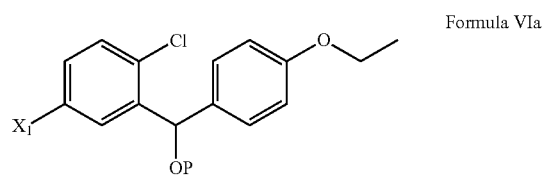

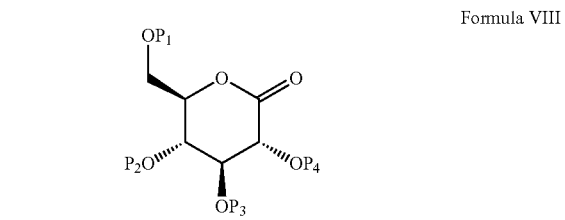

wherein "P" represents hydrogen or a suitable hydroxyl protecting group and $X_1$ represents a suitable leaving group; $P_1$, $P_2$, $P_3$ and $P_4$ independently represents hydrogen or a suitable hydroxyl protecting group;

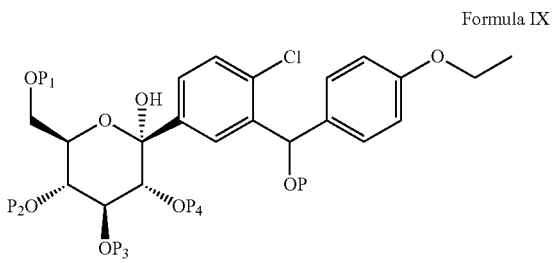

b) converting the compound of Formula IX to a compound of Formula XI, wherein $R_1$ represents hydrogen or a $C_{1-12}$ alkyl group; and

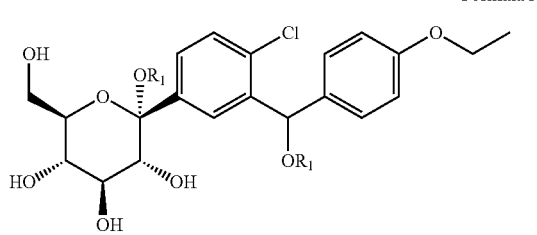

Formula XI c) reducing the compound of Formula XI with a suitable reducing agent to obtain dapagliflozin of Formula I.

Unless otherwise specified the term "$X_1$" and "$X_2$" used herein are represents a suitable leaving group and are selected from but not limited to halogen such as fluoro, chloro, bromo, iodo and the like; preferably bromo or iodo.

Unless otherwise specified the substituents "P" "$P_1$", "$P_2$", "$P_3$" and "$P_4$" represents a "suitable hydroxyl protecting group". Examples of hydroxyl protecting groups include, but are not limited, to alkyl, allyl, pivaloyl, acetyl (Ac), tosyl (Ts), mesyl (Ms), trimethylsilyl (TMS), triethylsilyl (TES), triisopropylsilyl (TIPS), tertiary butyldimethylsilyl (TBS), 2-(trimethylsilyl) ethoxymethyl (SEM), benzyl (Bn), para-methoxybenzyl (PMB), trityl (Tr), para-bromobenzoyl, para-nitrobenzoyl, benzoyl (Bz), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM) and the like.

Unless otherwise specified the term "co-crystals" used herein the specification refers a to crystalline material comprised of two or more unique solids at room temperature, each containing distinctive physical characteristics, such as structure, melting point and heats of fusion.

The starting materials of compounds of Formula VIa is known in the art and can be prepared by any of conventional methods reported in the art or can be prepared according to the present invention described herein below.

The step a) of the aforementioned process involves the reaction of a compound of Formula VIa; wherein $X_1$ represents a suitable leaving group and "P" represents hydrogen or a suitable hydroxyl protecting group with glucono lactone of Formula VIII to obtain a compound of Formula IX, wherein $P_1$, $P_2$, $P_3$ and $P_4$ independently represents hydrogen or a suitable hydroxyl protecting group;

Preferably, the compound of Formula VIa; wherein the "$X_1$" is a suitable leaving group and P is hydrogen is first converted into its hydroxyl protecting derivative of Formula VIa by treating with a suitable hydroxyl protecting group to obtain a compound of Formula VIa; wherein P represents a suitable hydroxyl protecting group.

In a preferred embodiment, the hydroxyl group of compound of Formula VIa; wherein "P" represents hydrogen is protected with suitable hydroxyl protecting group to obtain a compound of Formula VIa; wherein "P" represents a suitable hydroxyl protecting group.

In another embodiment, the compounds of Formula VIa thus formed herein is represented as follows:

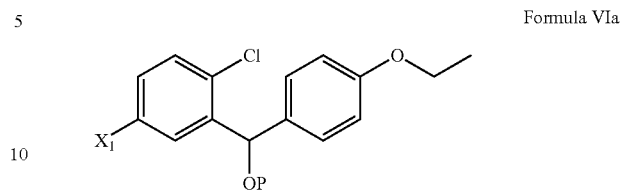

Formula VIa wherein the suitable hydroxyl-protecting group "P" includes, but are not limited to, alkyl, allyl, pivaloyl, acetyl (Ac), tosyl (Ts), mesyl (Ms), trimethylsilyl (TMS), triethylsilyl (TES), triisopropylsilyl (TIPS), tertiary butyldimethylsilyl (TBS), 2-(trimethylsilyl)ethoxymethyl (SEM), benzyl (Bn), para-methoxybenzyl (PMB), trityl (Tr), para-bromobenzoyl, para-nitrobenzoyl, benzoyl (Bz), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM) and the like; preferably mesyl, tosyl or trimethyl silyl.

The protection of hydroxyl group of compound of Formula VIa; wherein "P" is hydrogen; is carried out in presence of a base and a suitable organic solvent at a temperature of about 0° C. to about 50° C.

The base used herein for protection of hydroxyl group is selected from the group consisting of triethylamine, isopropyl ethylamine, diisopropyl amine, diisopropyl ethylamine, N-methyl morpholine, piperidine, pyridine and the like and mixtures thereof; preferably triethyl amine.

The suitable organic solvent used herein is selected from, but is not limited to halogenated hydrocarbons, ethers, amides and mixtures thereof. The halogenated hydrocarbons include, but are not limited to methylene chloride, ethylene chloride, chloroform and the like; ethers include, but are not limited to tetrahydrofuran, dimethyl ether, diisopropyl ether, methyl tertiary butyl ether, 1,4-dioxane and the like; amides include, but are not limited to dimethyl formamide, dimethyl acetamide and the like and mixtures thereof, preferably methylene chloride.

The protection of hydroxyl group is carried out at a temperature of about 0° C. to about 50° C.; preferably the reaction is carried out at 25-35° C. and maintained the reaction mass for a period of about 30 minutes to about 5 hours.

In another embodiment, the present invention provides a compound of Formula VIa:

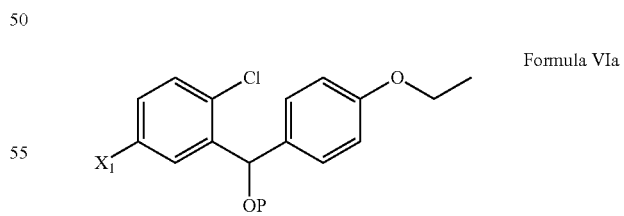

Formula VIa wherein "$X_1$" represents a suitable leaving group selected form the group consisting of fluoro, chloro, bromo or iodo and the like; and P represents hydrogen or a suitable hydroxyl protecting group selected from the group consisting of alkyl, allyl, pivaloyl, acetyl (Ac), tosyl (Ts), mesyl (Ms), trimethylsilyl (TMS), triethylsilyl (TES), triisopropylsilyl (TIPS), tertiary butyldimethylsilyl (TBS), 2-(trimethylsilyl) ethoxymethyl (SEM), benzyl (Bn), para-methoxybenzyl (PMB), trityl (Tr), para-bromobenzoyl, para-nitrobenzoyl, benzoyl (Bz), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM)), and the like.

In a preferred embodiment, the present invention provides compounds of Formula VIa1, Formula VIa2 or Formula VIa3.

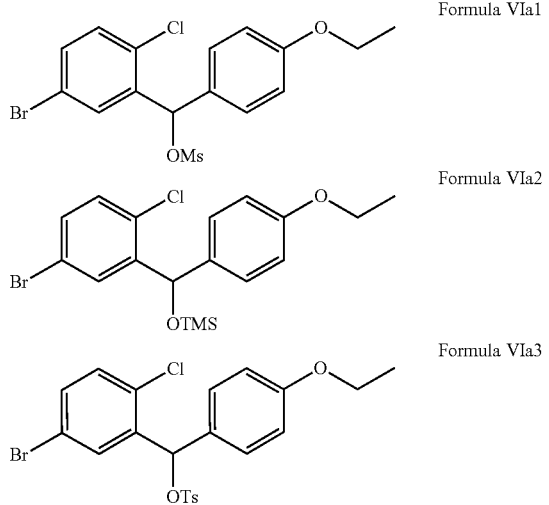

Formula VIa1

Formula VIa2

Formula VIa3

In another embodiment, the compound of Formula VIa can be used as an intermediate or as a starting material in the preparation of dapagliflozin of Formula I.

The resultant compound of Formula VIa thus formed may be isolated or further processed without isolating into next stage; preferably it may be further processed in to next stage by isolating the compound of Formula VIa.

The compound of Formula VIa obtained from the process described above is converted in to a compound of Formula IX by condensing the compound of Formula VIa with glucono lactone of Formula VIII, wherein the substituents "P", "$P_1$", "$P_2$", "$P_3$" and "$P_4$" represents hydrogen or a suitable hydroxyl protecting group.

Preferably, the glucono lactone of Formula VIII is represented as follows:

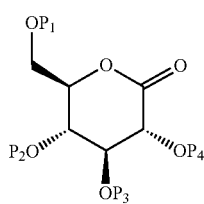

wherein $P_1$, $P_2$, $P_3$ and $P_4$ independently represents hydrogen or a suitable hydroxyl protecting group, wherein the hydroxyl protecting groups are selected from the group consisting of alkyl, allyl, pivaloyl, acetyl (Ac), tosyl, mesyl, trimethylsilyl (TMS), triethylsilyl (TES), triisopropylsilyl (TIPS) or tertiary butyldimethylsilyl (TBS), 2-(trimethylsilyl) ethoxymethyl (SEM), benzyl (Bn), para-methoxybenzyl (PMB), trityl (Tr), para-bromobenzoyl, para-nitrobenzoyl, benzoyl (Bz), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), and the like. Further, the protecting groups for hydroxyl groups may form acetal or silyl acetal together with adjacent hydroxyl groups; preferably $P_1$, $P_2$, $P_3$ and $P_4$ independently represents trimethylsilyl group.

Advantageously the compound of Formula VIa is first treated with a water immiscible organic solvent and then the solvent may be removed to limit the moisture content in the reaction. The water immiscible organic solvent used herein is selected from the group consisting of toluene, xylene, ethyl acetate, heptane, hexane and the like; preferably toluene.

Typically the condensation of compound of Formula VIa with glucono lactone of Formula VIII may be carried out in presence of a base in a suitable solvent at a temperature of about −100° C. to about 10° C. to obtain a compound of Formula IX.

The base used herein for condensation includes, but is not limited to organolithium compounds such as n-butyl lithium, sec-butyl lithium or tert-butyllithium; sodium hydride, potassium hydride, isopropylmagnesium chloride-lithium chloride complex, sec-butylmagnesium chloride lithium chloride complex or (trimethylsilyl) methyl lithium; preferably the base is n-butyl lithium.

The suitable solvent used herein for condensation includes but is not limited to ethers, aromatic hydrocarbons, alcohols, halogenated hydrocarbons and the like and mixtures thereof. The ethers include, but are not limited to tetrahydrofuran, dimethyl ether, diisopropyl ether, methyl tertiary butyl ether, 1,4-dioxane and the like; aromatic hydrocarbons include, but are not limited to toluene, xylene and the like; alcohols include, but are not limited to methanol, ethanol, isopropanol, n-propanol, t-butanol and the like; halogenated hydrocarbons include, but are not limited to methylene chloride, ethylene chloride, chloroform and the like; and mixture thereof; Preferably the suitable solvent is a mixture of toluene and tetrahydrofuran.

The condensation reaction is carried out at a temperature of about −100° C. to about 10° C. for about 1-5 hours; preferably the reaction is carried out at about −90° C. to about −80° C. for about 3 hrs.

After completion of the reaction, the resultant compound of Formula IX thus formed may be isolated as a solid or proceed further without isolating the compound of Formula IX in to subsequent reactions.

In another embodiment, the compound of Formula IX thus obtained is used as such for the subsequent reactions without isolating from the reaction mass as solid.

In another embodiment, the present invention provides a compound of Formula IX:

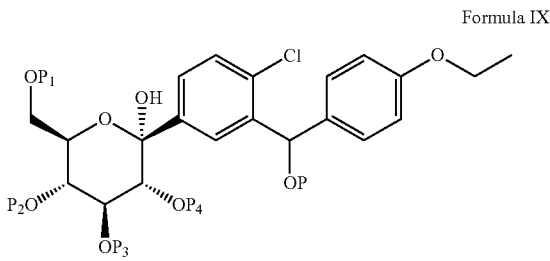

Formula IX wherein the substituents "P", "$P_1$", "$P_2$", "$P_3$" and "$P_4$" represents hydrogen or a "suitable hydroxyl protecting group", wherein the hydroxyl protecting groups are selected from the group consisting of alkyl, allyl, pivaloyl, acetyl (Ac), tosyl (Ts), mesyl (Ms), trimethylsilyl (TMS), triethylsilyl (TES), triisopropylsilyl (TIPS), tertiary butyldimethylsilyl (TBS), 2-(trimethylsilyl) ethoxymethyl (SEM), benzyl (Bn), para-methoxybenzyl (PMB), trityl (Tr), para-bromobenzoyl, para-nitrobenzoyl, benzoyl (Bz), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), and the like. Further, the protecting group for hydroxyl groups may form acetal or silyl acetal together with adjacent hydroxyl groups.

In a preferred embodiment, the present invention provides compounds of Formula IXa1, Formula IXa2 or Formula IXa3.

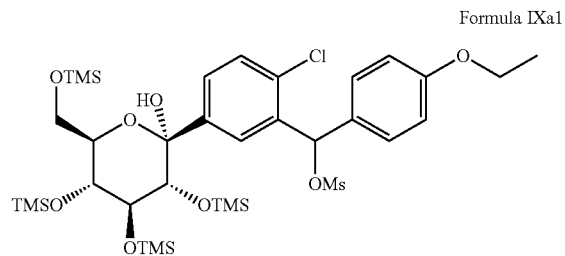

Formula IXa1

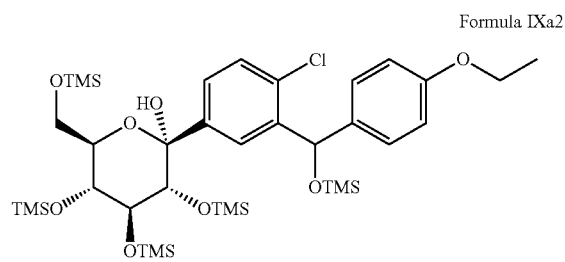

Formula IXa2

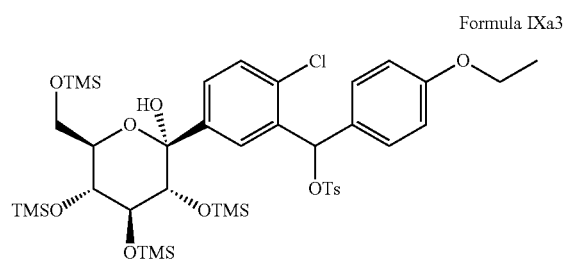

Formula IXa3

In another embodiment, the compound of Formula IX thus obtained can be used as an intermediate or as a starting material in the preparation of dapagliflozin of Formula I.

The compound of Formula IX obtained from the process described as above is converted in to the compound of Formula XI by glycosidation of compound of Formula IX through formation of dihydroxy compound of Formula X as an intermediately product, wherein the substituents "P", "$P_1$", "$P_2$", "$P_3$" and "$P_4$" represents hydrogen or a suitable hydroxyl protecting group.

The intermediatery dihydroxy compound of Formula X is represented as follows:

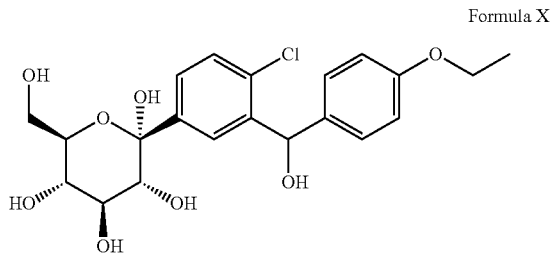 [SMILES: CCOc1ccc(C(O)c2cc([C@]3(O)O[C@H](CO)[C@@H](O)[C@H](O)[C@H]3O)ccc2Cl)cc1]

Formula X

The conversion of step b) of the compound of Formula IX to a compound of Formula XI, wherein the substituents "P", "$P_1$", "$P_2$", "$P_3$" and "$P_4$" represents hydrogen or a suitable hydroxyl protecting group involves with a suitable glycosidation reagent in presence of a suitable nucleophilic compound such as an alcohol compound.

The glycosidation reagent used herein is capable of facilitating deprotection of the hydroxyl groups through removal of the protecting groups "P", "$P_1$", "$P_2$", "$P_3$" and "$P_4$", which results dihydroxy compound of Formula X, which is then simultaneously forming corresponding dialkoxy compound of Formula XI by using a suitable alcohol group.

The compound of Formula XI is specifically represented are as follows:

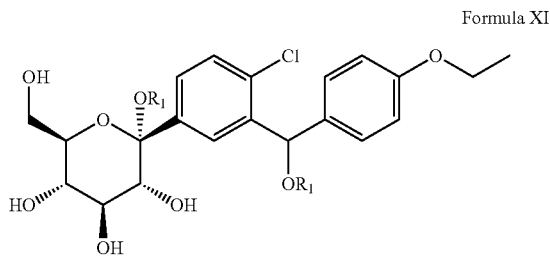

Formula XI wherein $R_1$ represents hydrogen or an alkyl group; preferably $C_{1-12}$ alkyl group.

The suitable glycosidation reagent used herein is selected from the group consisting of an organic acid selected from formic acid, acetic acid, trifluoroacetic acid, methanesulfonic acid, oxalic acid or p-toluene sulfonic acid; an inorganic acid selected from hydrochloric acid, sulfuric acid or nitric acid; and a lewis acid selected from boron trifluoride diethyletherate, scandium (III) trifluoromethanesulfonate, titanium (IV) isopropoxide, tin (IV) chloride, zinc (II) bromide or zinc (II) chloride; preferably the glycosidation reaction is carried out by using methane sulfonic acid or hydrochloric acid.

Further the alcohol used herein for the glycosidation reaction is $C_{1-12}$ alcohol, which is selected from methanol, ethanol, isopropanol and 2-methoxy ethanol and the like; preferably the alcohol is methanol or 2-methoxy ethanol.

The glycosidation reaction is carried out preferably by using methane sulfonic acid in methanol medium at a temperature of about 20° C. to about 65° C.; preferably at about 25° C. to about 35° C.

It is observed that by the use of insufficient amount of an acid such as methanesulfonic acid during the glycosidation reaction, hydroxyl impurity of Formula E is formed which is once formed and is carried forward in subsequent reaction steps and results in the final dapagliflozin API of low purity and it is difficult to remove this impurity from the final API which requires additional crystallization steps to remove this impurity.

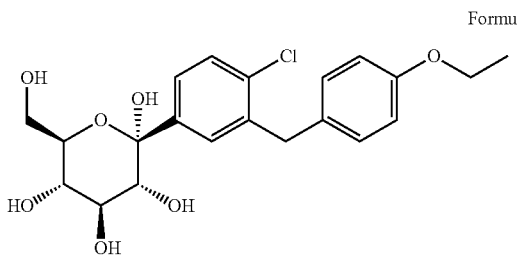

Formula E

Thus in order to avoid the formation of hydroxyl impurity of Formula E it is necessary to maintain the sufficient amount of acid during the glycosidation.

In another embodiment, the present invention provides a process for the preparation of dapagliflozin having less than 0.1% of hydroxyl impurity of Formula E, as measured by HPLC by maintaining the sufficient amount of acid during the glycosidation.

In another embodiment, the present invention provides pure dapagliflozin of Formula I or its solvates or co-crystals having less than 0.1% of hydroxyl impurity of Formula E, as measured by HPLC.

The resultant compound of Formula XI thus formed may be isolated as a solid or proceed further without isolating the compound of Formula XI in to subsequent reactions. Preferably the compound of Formula XI is isolated as a solid from the reaction mass.

In another embodiment, the present invention provides a compound of Formula XI;

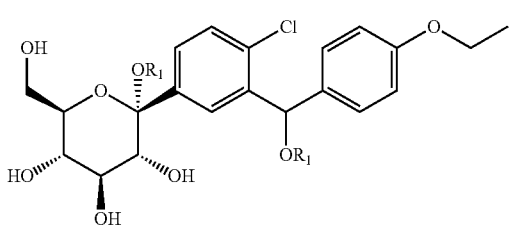

Formula XI wherein $R_1$ represents hydrogen or $C_{1-12}$ alkyl group.

In another embodiment, the present invention provides a compound of Formula XIa, Formula XIb, Formula XIc or Formula XId.

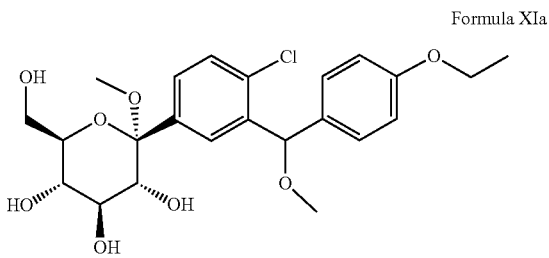

Formula XIa

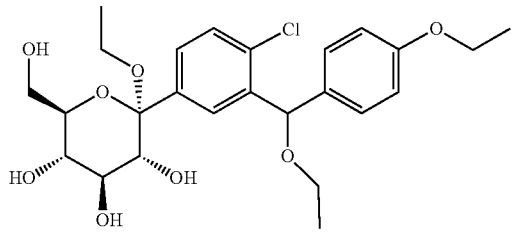

Formula XIb

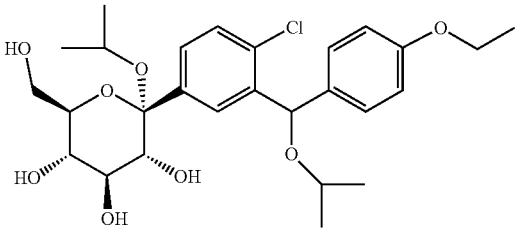

Formula XIc

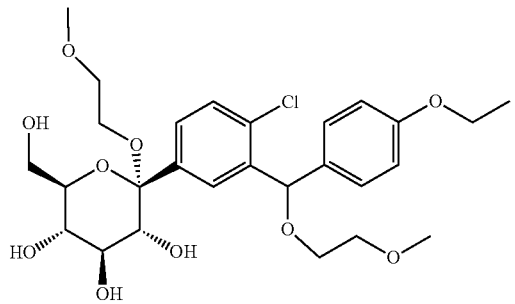

Formula XId

The compound of Formula XI; preferably the compound of Formula XIa thus obtained by the process of the present invention may contain compounds of Formula F and compound of Formula G as impurities, which are present in the range of about 2% to about 5% by HPLC and each impurity represented as follows:

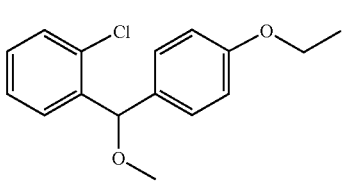

Formula F

Desbromo methoxy impurity

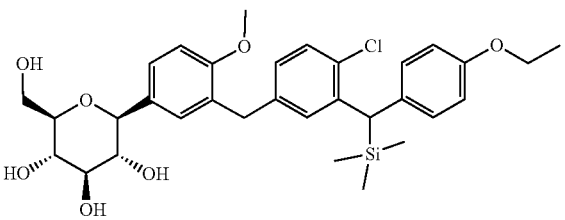

Formula G

Mono methoxy monosilyl impurity

Without removing these impurities at this stage of the synthesis, the same may carry forward to further steps in subsequent reactions and generates corresponding impurities in each stage up to the final stage, as a result getting the final product with low product yields and purity. In order to remove these impurities from each stage of the synthesis requires multiple purification processes that make the process lengthy and not viable on commercial scale.

Thus the present invention involves the purification of compound of Formula XI, in order to avoid repetitive purifications to separate impurities in each stage of the synthesis up to the final API. After completion of the reaction the product containing organic solvent may be evaporated under vacuum to obtain a compound of Formula XI as residue. The residue so obtained is purified by using a novel solvent system to obtain a pure compound of Formula XI.

In another embodiment, the present invention provides a process for purification of a compound of Formula XI using a suitable solvent system.

In accordance with another embodiment, the present invention provides a process for purification of a compound of Formula XI, comprising:
  i) dissolving a compound of Formula IX in one or more solvents,
  ii) adding an antisolvent to the step i) solution or vice-versa, and
  iii) filtering the pure compound of Formula IX;
wherein the one or more solvents are selected from the group consisting of esters, ethers, aromatic hydrocarbons, halogenated hydrocarbons and the like and mixtures thereof, wherein the antisolvent is selected from the group consisting of water, aliphatic or cyclic hydrocarbons and mixtures thereof.

Examples of one or more organic solvents of step i) includes but are not limited to esters such as methyl acetate, ethyl acetate, isopropyl acetate, n-propyl acetate, n-butyl acetate, t-butyl acetate and the like; ethers such as tetrahydrofuran, dimethyl ether, diisopropyl ether, methyl tertiary butyl ether, 1,4-dioxane and the like; aromatic hydrocarbons such as toluene, xylene and the like; halogenated hydrocarbons such as methylene chloride, ethylene chloride, chloroform and the like and mixtures thereof; preferably the organic solvent is methyl tertiary butyl ether.

The suitable temperature for step i) reaction is about 25° C. to about reflux temperature of the solvent used. Any other temperatures may also be acceptable, provided a clear solution of the concerned materials is obtained in the solvents chosen; preferably at about 25° C. to about 35° C.

Step ii) of the aforementioned process involves precipitation of compound of Formula XI by either addition of suitable antisolvent to the step i) solution or addition of step i) solution into a suitable antisolvent.

The suitable antisolvent include, but are not limited to water, aliphatic or cyclic hydrocarbons such as n-hexane, n-heptane, cyclohexane, cycloheptane and the like and mixtures thereof; preferably the suitable antisolvent is cyclohexane.

The anti-solvent is added to step i) reaction solution at about 10° C. to about 20° C. and the resultant pure compound of Formula XI can be recovered by conventional techniques, for example filtration. The resultant pure compound of Formula XI further dried at a temperature ranging from about 30° C. to about 60° C.

The compound of Formula XI; preferably the compound of Formula XIa1 thus obtained according to purification process of the invention having less than 2% of compound of Formula F and less than 1% of compound of Formula G as impurities as measured by HPLC.

In another embodiment, the compound of Formula XI obtained according to the processes of the invention can be used as an intermediate or as a starting material in the preparation of dapagliflozin of Formula I.

The conversion of the compound of Formula XI to dapagliflozin of Formula I or its solvates or co-crystals involves reduction of the compound of Formula XI with suitable reducing agents according to step c) of the aforementioned embodiment.

The step c) of the aforementioned process involves the reduction of compound of Formula XI with a suitable reducing agent to obtain dapagliflozin of Formula I or its solvates or co-crystals, wherein the reduction reaction is carried out optionally in presence of a Lewis or bronsted acid at a temperatures of about −70° C. to about 30° C.

The suitable reducing agents used herein includes, but are not limited to silanes, such as triethyl, tripropyl, triisopropyl or diphenylsilane; sodium borohydride, sodium cyanoborohydride, zinc borohydride, borane reducing agents, lithium aluminium hydride, diisobutylaluminium hydride or samarium iodide; preferably the reducing agent is triethyl silane.

The suitable Bronsted acid used herein, includes, but is not limited to hydrochloric acid, toluenesulphonic acid, trifluoroacetic acid, acetic acid and the like. The suitable Lewis acid used herein, includes, but is not limited to boron trifluoride diethyl etherate, trimethylsilyltriflate, titanium tetrachloride, tin tetrachloride, scandium triflate, zinc iodide and the like; preferably the lewis acid is boron trifluoride etherate.

The reduction of compound of Formula XI is carried out in a suitable solvent. The suitable solvent, includes, but is not limited to halogenated hydrocarbons such as methylene chloride, chloroform and the like; ethers such as diethyl ether, tetrahydrofuran, dioxane and the like; nitriles such as acetonitrile, propionitrile, benzonitrile and the like; aromatic hydrocarbons such as toluene, xylene and the like; aliphatic or cyclic hydrocarbons such as n-hexane, n-heptane, cyclohexane, cycloheptane and the like and mixtures thereof.

Preferably, the step c) reaction carried out with a suitable combination of reagents consists, for example, triethylsilane and boron trifluoride etherate in a mixture of acetonitrile and methylene chloride at temperatures of about −60° C. to about 30° C. for about a period of 30 minutes to about 3 hours.

After completion of the reaction, the resultant dapagliflozin of Formula I can be isolated by known methods in the art for example separating the product containing organic layer and removal of solvent or proceed further without isolating the dapagliflozin of Formula I in to subsequent reactions. Preferably the resulting dapagliflozin of Formula I is converted in to its co-crystal form with a suitable co-crystal former as an intermediate in the preparation of pure dapagliflozin.

In another embodiment, alternatively, the compound of Formula IX is reacted with a suitable acid to obtain a dihydroxy compound of Formula X, which is then converted in to the dapagliflozin of Formula I by treating with a suitable reducing agent according to step c) of the aforementioned embodiment.

Dapagliflozin of Formula I thus obtained by the process of the invention may contaminate with α-anomer impurity of Formula H and dimer impurity of Formula J, which needs to be removed by purification in order to meet regulatory requirements.

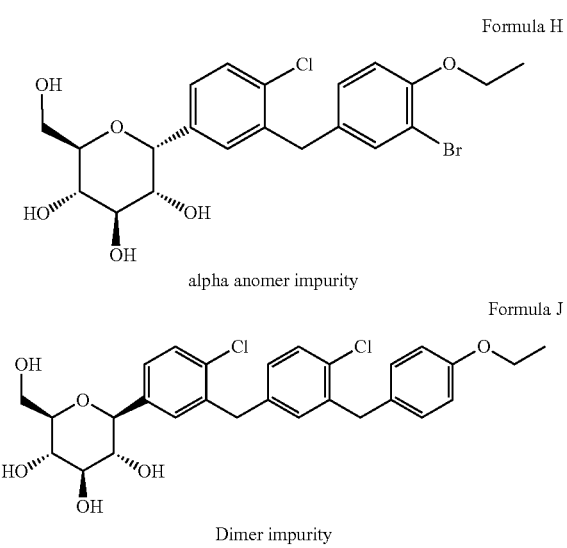

alpha anomer impurity

Dimer impurity

In another embodiment, the present invention provides a process for purification of dapagliflozin of Formula I, comprising: forming dapagliflozin co-crystals as intermediate, converting dapagliflozin co-crystals into pure dapagliflozin of Formula I.

In another embodiment, the present invention provides a process for the purification of dapagliflozin of Formula I, comprising:
a) providing a solution or suspension of dapagliflozin in one or more organic solvents,
b) adding co-crystal former to the step a) reaction mass,
c) isolating the dapagliflozin co-crystals,
d) converting the dapagliflozin co-crystals into dapagliflozin, and
e) isolating the pure dapagliflozin of Formula I.

Examples of one or more organic solvents of step a) includes but are not limited to esters such as methyl acetate, ethyl acetate, isopropyl acetate, n-propyl acetate, n-butyl acetate, t-butyl acetate and the like; alcohols such as methanol, ethanol, isopropanol, n-propanol, n-butanol, isobutanol and the like; ethers such as tetrahydrofuran, dimethyl ether, diisopropyl ether, methyl tertiary butyl ether, 1,4-dioxane and the like, water and mixtures thereof, preferably the organic solvent is ethyl acetate.

The suitable temperature for providing a solution of dapagliflozin may be carried out at a temperature of about 25° C. to reflux temperature.

The co-crystal former of step b) is selected from the group comprising DL-pipecolic acid, D-pipecolic acid, L-pipecolic acid, ammonia, nicotinic acid, pyrazine-2-carboxylic acid, imidazole, morpholine and the like; preferably the co-crystal former is DL-pipecolic acid.

The suitable temperature for step b) reaction is about 20° C. to about reflux temperature of the solvent used; preferably at about 75° C. to about 85° C. for about 3 hrs.

The isolation of dapagliflozin co-crystals may be carried out by known methods in the art, for example, filtration, and the obtained dapagliflozin co-crystals may optionally be further dried at suitable temperatures i.e. about 40° C. to about 60° C. for about 8 hrs.

Step d) of the foregoing process involves conversion of dapagliflozin co-crystals into dapagliflozin of Formula I.

The dapagliflozin co-crystals are treated with water and a water immiscible solvent such as ethyl acetate at a temperature of about 0° C. to 50° C., preferably at about 25° C. to 35° C. and then separating the product containing water immiscible organic layer.

The dapagliflozin co-crystals obtained is first neutralized in water and a water immiscible solvent such as ethyl acetate optionally in presence of a base such as sodium or potassium carbonate or bicarbonate, ammonia and mixtures thereof. at a temperature of about 0° C. to about 50° C.; preferably at about 25° C. to about 35° C. Then, the water immiscible organic solvent layer may be separated from the reaction mass and thereafter the product containing organic layer may be evaporated under vacuum.

In a preferred embodiment, the product containing water immiscible organic layer is treated with water. At which point, the dapagliflozin co-crystals are breaking and the co-crystal former went to the aqueous layer. Then the product containing water immiscible organic solvent may be separated followed by distillation of solvent completely under reduce pressure to obtain pure dapagliflozin of Formula I. The resultant dapagliflozin may be isolated by crystallizing in a solvent or a mixture of solvent and an antisolvent. The solvent for the crystallization of dapagliflozin includes but are not limited to methanol, ethanol, methyl tert-butyl ether, n-heptane, n-hexane, cyclohexane, water and mixtures thereof.

In another embodiment, the present invention provides pure dapagliflozin of Formula I having a total purity greater than 99.5%, as measured by HPLC.

In another embodiment, The present invention provides the pure Dapagliflozin of Formula I or its solvates or co-crystals obtained by above process having chemical purity of at least about 95%, as measured by HPLC, preferably at least about 98%, as measured by HPLC and more preferably at least about 99.5%, as measured by HPLC; and contains less than 0.3% of total impurities, which include α-anomer impurity of Formula H and dimer impurity of Formula J as measured by HPLC.

In another embodiment, the present invention provides pure dapagliflozin of Formula I or its solvates or co-crystals having less than 0.1%, as measured by HPLC of each of α-anomer impurity of Formula H and dimer impurity of Formula J.

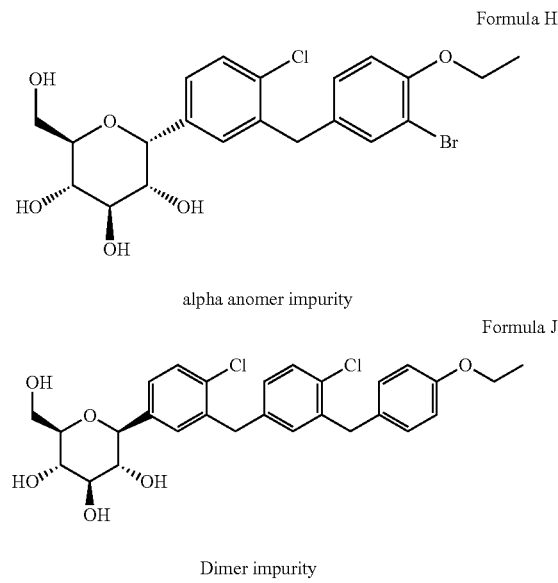

alpha anomer impurity

Dimer impurity

In another embodiment, the present invention provides a process for the preparation of dapagliflozin of Formula I or its solvates or co-crystals thereof; comprising:

i) reacting benzoic acid of Formula II with N,O-dimethyl hydroxyl amine or a salt thereof to obtain amide compound of Formula III, wherein "X1" represents a suitable leaving group;

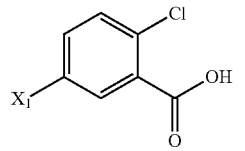

Formula II

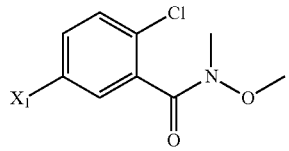

Formula III ii) reducing the compound of Formula III with a suitable reducing agent to obtain an aldehyde compound of Formula IV, wherein "$X_1$" represents a suitable leaving group;

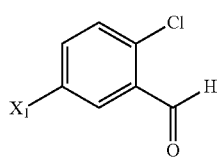

Formula IV iii) reacting the aldehyde compound of Formula IV with a compound of Formula V, wherein $X_1$ and $X_2$ independently represents a suitable leaving group;

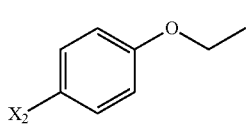

Formula V to obtain a compound of Formula VI, wherein "$X_1$" represents a suitable leaving group; and

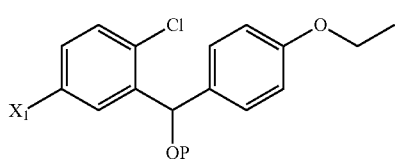

Formula VIa iv) converting the compound of Formula VI into dapagliflozin of Formula I.

In a preferred embodiment, $X_1$ and $X_2$ are independently represents a suitable leaving group; which is specifically represented as halogen such as fluoro, chloro, bromo, iodo and the like; preferably $X_1$ and $X_2$ are independently represented as bromo or iodo.

In a preferred embodiment, the compound of Formula VI is a compound of Formula VI-I:

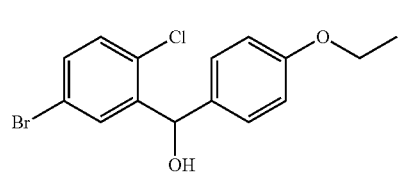

Formula VI-I

Step i) of the aforementioned process involves the reaction of 5-halo-2-chloro benzoic acid with N,O-dimethyl hydroxyl amine or a salt thereof, preferably a hydrochloric, hydrobromic, tartaric or succinic acid salt, in presence of a coupling agent, a base and a suitable solvent.

The coupling reagents used herein includes, but is not limited to 1,3-dicyclohexylcarbodiimide (DCC), 0-benzotriazole-1-yl-N,N,N',N'-tetramethyluronium hexafluorophosphate (HBTU), N,N'-Diisopropylcarbodiimide (DIC), 1-(3-dimethylaminopropyl)-3-ethylcarbodiimide hydrochloride (EDC.HCl), 1-[Bis(dimethylamino)methylene]-1H-1,2,3-triazolo[4,5-b]pyridinium 3-oxid hexafluorophosphate (HATU) and the like. The additive such as 1-hydroxybenzotriazole hydrate (HOBT) or 3,4-dihydro-3-hydroxy-4-oxo-1,2,3-benzotriazine (HOOBT) may or may not used in the reaction; preferably the coupling is carried out in presence of DCC as coupling agent.

The suitable base used herein includes, but is not limited to amine bases such as diethylamine, dimethyl amine, triethylamine, isopropyl ethylamine, diisopropyl amine, diisopropyl ethylamine; N-methyl morpholine, piperidine, pyridine and the like and mixtures thereof; preferably the base is diethylamine.

The suitable solvent used herein, includes but is not limited to halogenated hydrocarbons, ethers, aromatic hydrocarbons and mixtures thereof. The halogenated hydrocarbons include, but are not limited to methylene chloride, ethylene chloride, chloroform and the like; ethers include, but are not limited to tetrahydrofuran, 2-methyl tetrahydrofuran, methyl tertiary butyl ether, 1,4-dioxane and the like; aromatic hydrocarbons include, but are not limited to toluene, xylene and the like and mixture thereof; preferably the suitable organic solvent is methylene chloride.

The coupling reaction is carried out at a temperature of about −10° C. to about 50° C. followed by stirring the contents at the same temperature for a period of about 30 minutes to about 3 hours.

After, completion of the reaction, the resultant organic layer is concentrated under reduce pressure and strip off with a hydrocarbon solvent followed by isolating the product from a suitable hydrocarbon solvent such as heptane.

Step ii) of the aforementioned process involves the reduction of amide compound of Formula III with a suitable reducing agent in a suitable solvent to obtain an aldehyde compound of Formula IV.

The suitable reducing agent used herein for reduction is selected from lithium aluminium hydride (LAH), diisobutylalurninum hydride (DIBAL-H) or sodium bis(2-methoxyethoxy) aluminumhydride (vitride); preferably the reducing agent is lithium aluminium hydride (LAH).

The suitable solvent includes but are not limited to toluene, tetrahydrofuran, diethyl ether and the like; preferably toluene.

The reduction is carried out at a temperature of about −75° C. to about 0° C. followed by stirring the reaction mass at the same temperature for a period of about 30 minutes to about 5 hours.

The resultant aldehyde compound of Formula IV after reduction may be isolated by quenching the reaction mass with a base, for example with an aqueous sodium potassium tartrate solution and followed by extraction with organic solvent and concentrating the organic layer. The resulting residue was dilute with hydrocarbon solvents and cooled to about −10° C. to about 20° C. followed by stirring the reaction mass for a period of about 1-5 hours and isolating the compound of Formula IV by techniques known in the art, for example, filtration.

The organic solvent used for extraction includes, but is not limited to aromatic hydrocarbons, esters, halogenated hydrocarbons; water and mixtures thereof. The aromatic hydrocarbons include, but are not limited to toluene, xylene and the like; esters include, but are not limited to ethyl acetate, methyl acetate, isopropyl acetate and the like; halogenated hydrocarbons include, but are not limited to methylene chloride, ethylene chloride, chloroform and the like; water and mixtures thereof, preferably the organic solvent used for extraction is toluene.

The hydrocarbon solvent used herein includes, but is not limited to aromatic hydrocarbons, aliphatic hydrocarbons or alicyclic hydrocarbons and mixtures thereof. The aromatic hydrocarbons include, but are not limited to toluene, xylene and the like; aliphatic hydrocarbons or alicyclic hydrocarbons include, but are not limited to hexane, heptane, propane, cyclopropane, cyclobutane, cyclopentane, cyclohexane, methyl cyclohexane, cycloheptane, cyclooctane and the like; and mixtures thereof, preferably hydrocarbon solvent is heptane.

Step iii) of the afore mentioned process involves the reaction of an aldehyde compound of Formula IV with a compound of Formula V in presence of a suitable base and a suitable solvent at a temperature of about −100° C. to about 10° C., preferably at about −90 to −80° C. to obtain compound of Formula VI.

The suitable solvent used herein for step iii) includes, but is not limited to ethers, amides, nitriles, aromatic hydrocarbons and mixtures thereof; specifically the suitable solvent may be selected from tetrahydrofuran, dimethylformamide, acetonitrile, toluene, and mixtures thereof; preferably the solvent is tetrahydrofuran.

The suitable base used herein for step iii) includes, but is not limited to n-butyl lithium, sec-butyl lithium, tert-butyllithium, sodium hydride, potassium hydride, isopropylmagnesium chloride-lithium chloride complex, sec-butyl magnesium chloride lithium chloride complex, (trimethylsilyl) methyl lithium; preferably the base is n-butyl lithium.

The step iii) reaction is carried out at a temperature of about −90° C. to about −80° C. followed by stirring the reaction mass at the same temperature.

After completion of the reaction, the resultant compound of VI may be isolated. The isolation step involves, after completion of the reaction, the reaction mass is extracted with a water immiscible organic solvent such as ethyl acetate, methylene chloride, 2-methyl-THF, toluene, and the like; preferably with ethyl acetate. Thereafter the product containing water immiscible organic solvent may be evaporated under reduced pressure to obtain the compound of Formula VI as residue.

The compound of Formula VI, preferably the bromo compound of Formula VI-I thus obtained by the process of the present invention may contain Impurity of Formula A, Impurity of Formula B, Impurity of Formula C and dimer impurity of Formula D as impurities, which are present in the range of about 0.5% to about 2% by HPLC and each impurity represented as follows:

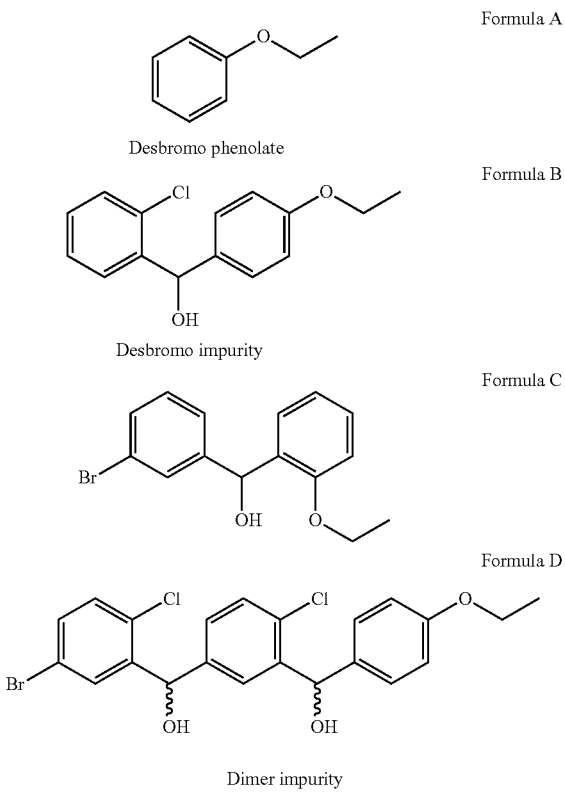

Desbromo phenolate — Formula A

Desbromo impurity — Formula B

Formula C

Dimer impurity — Formula D

Without removing these impurities at this stage of the synthesis, the same may carry forward to further steps in subsequent reactions and generates corresponding impurities in each stage up to the final stage, as a result getting the final product with low product yields and purity. In order to remove these impurities from each stage of the synthesis requires multiple purification processes that make the process lengthy and not viable on commercial scale.

The present inventors have found that purification of compound of Formula VI using a modified isolation and novel solvent system, which may efficiently, removing the above impurities and getting high pure compound of Formula VI thereby getting high pure dapagliflozin API using the pure compound of Formula VI.

In another embodiment, the present invention provides a process for purification of a compound of Formula VI using a suitable solvent system.

In another embodiment, the present invention provides a process for purification of a compound of Formula VI, comprising:
 i) dissolving a compound of Formula VI in a suitable solvent,
 ii) optionally adding an antisolvent to the step a) solution,
 iii) cooling the solution to precipitation, and
 iv) filtering the pure compound of Formula VI; wherein the suitable solvent is selected from the group consisting of alcohols, aromatic hydrocarbons, aliphatic or cyclic hydrocarbons and mixtures thereof.

The step i) of the aforementioned process may include dissolving a compound of Formula VI obtained by the process described as just above, in a suitable solvent at a suitable temperature. The suitable solvent includes, but are not limited to alcohols include, but are not limited to methanol, ethanol, isopropanol, n-propanol, n-butanol, isobutanol and the like; aromatic hydrocarbons include, but are not limited to toluene, xylene and the like; aliphatic or cyclic hydrocarbons include, but are not limited to n-hexane, n-heptane, cyclohexane, cycloheptane and the like; and mixtures thereof; preferably the suitable solvent is a mixture of isopropanol and cyclohexane.

The suitable temperature for step i) reaction is about 25° C. to about reflux temperature of the solvent used. Any other temperatures may also be acceptable, provided a clear solution of the concerned materials is obtained in the solvents chosen; preferably the step i) reaction is carried out at temperature of about 70° C. to about 85° C.

Optionally, an anti-solvent is added to the resulting solution containing compound of Formula VI to effect the crystallization of the product; wherein the antisolvent is selected from the group consisting of water, aromatic hydrocarbons, aliphatic or cyclic hydrocarbons and mixtures thereof. The aromatic hydrocarbons include, but are not limited to toluene, xylene and the like; aliphatic or cyclic hydrocarbons include, but are not limited to n-hexane, n-heptane, cyclohexane, cycloheptane and the like; water and mixtures thereof.

Then, the resulting reaction mass may be cooled to a temperature of about 25° C. to about 35° C. or lower to precipitate out the product and the resultant pure compound of Formula VI can be recovered by conventional techniques, for example filtration. The resultant pure compound of Formula VI may optionally be further dried at a temperature ranging from about 50° C. to about 60° C.

The compound of Formula VI; preferably the compound of Formula VI-I thus obtained according to purification process of the invention having less than 0.5% of impurity of Formula A, less than 0.1% of Impurity of Formula B, less than 0.1% of Impurity of Formula C and less than 0.2% of Impurity of Formula D as measured by HPLC.

In another embodiment, the compound of Formula VI, preferably compound of Formula VI-I obtained according to the processes of the invention can be used as an intermediate or as a starting material in the preparation of dapagliflozin of Formula I.

In another embodiment, the present invention provides a process for the preparation of dapagliflozin of Formula I having less than about 10 ppm of desethyl dapagliflozin of Formula XII; comprising:
a) reacting an aldehyde compound of Formula IV with a compound of Formula V to obtain a compound of Formula VI, wherein $X_1$ and $X_2$ independently represents a suitable leaving group; and
b) converting the compound of Formula VI into dapagliflozin of Formula I; wherein the compound of Formula V having less than about 10 ppm of desethyl compound of Formula Va:

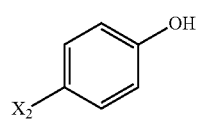

Formula Va

The desethyl analogue of dapagliflozin is very close to dapagliflozin by its chemical and physical properties; hence separation of each other is very difficult and cumbersome. Instead of doing cumbersome separation techniques to remove des ethyl analogue from the required dapagliflozin, selection of desethyl counterpart at the initial stage of the synthesis is considered as advantageous as it utilizes less quantity of raw materials in the further course of reactions and des ethyl analogue of dapagliflozin is well controlled up to the final stage of the synthesis. Thereby, with the process of the invention final dapagliflozin is obtained with required purity without necessity of repeated purifications.

Reaction of compound of formula IV and formula V having less than 10 ppm of des ethyl compound, wherein $X_1$ and $X_2$ independently represents a suitable leaving group; preferably $X_1$ and $X_2$ each independently bromo; is carried out using a procedure analogous to procedure described as above for the preparation of compound of formula IV.

In another embodiment, the present invention provides a process for the preparation of dapagliflozin of Formula I or its solvates or co-crystals thereof having less than about 10 ppm of desethyl dapagliflozin of Formula XII, less than about 0.15% of a compound of Formula XIII and a compound of Formula XIV, comprising:
a) reacting aldehyde compound of Formula IV with a compound of Formula V to obtain a compound of Formula VI, and
b) converting the compound of Formula VI into dapagliflozin of Formula I:
wherein the compound of Formula V comprises less than about 10 ppm of desethyl compound of Formula Va and/or less than 0.15% by weight of one or more of compound of Formula Vb, compound of Formula Vc, compound of Formula Vd and compound of Formula Ve.

The compound of Formula V used in the preparation of dapagliflozin having a leaving group at para-position of the phenyl ring. The suitable leaving group specifically can be represented as fluoro, chloro, bromo or iodo. During the process for the preparation of compound of Formula V, introduction of leaving group on the phenyl ring is always prone to attack other positions in addition to required para-position. This leads to formation of unwanted side products; the said unwanted side products may carry forward to subsequent reactions and formed as impurities in the final dapagliflozin.

The available compound of Formula V such as 1-ethoxy-4-bromo benzene contains traces of corresponding 2-bromo-1-ethoxybenzene impurity of Formula Vb, 2,4-dibromo-1-ethoxybenzene impurity of Formula Vc, 2,6-dibromo-1-ethoxybenzene impurity of Formula Vd, 2,4,6-tribromo-1-ethoxybenzene impurity of Formula Ve and 1-hydroxy-4-bromobenzene impurity of Formula Va. Hence purity of 1-ethoxy-4-bromobenzene, which is as starting material in the preparation of dapagliflozin, is important, as amount of dibromo, tribromo and 1-hydroxy compounds present in the 1-ethoxy-4-bromobenzene can lead to formation of dapagliflozin bromo impurities of Formula XV and XVI and desethoxy dapagliflozin of Formula XII respectively. The formation of these impurities in the final dapagliflozin complicates the purification of dapagliflozin and difficult to remove from final dapagliflozin. These by-product impurities cannot be in a product intended as to be marketed as an active pharmaceutical ingredients.

Reaction of compound of formula IV and formula V having less than about 10 ppm of desethyl compound of Formula Va and/or less than 0.15% by weight of one or more of compound of Formula Vb, compound of Formula Vc, compound of Formula Vd and compound of Formula Ve; is carried out using a procedure analogous to procedure described as above for the preparation of compound of Formula IV.

The one or more impurities of Formula Va, Vb, Vc, Vd and Ve are described as in below:

Formula Va
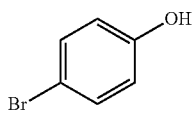

Formula Vb
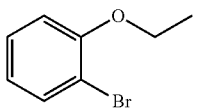

Formula Vc
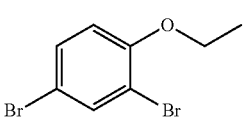

Formula Vd
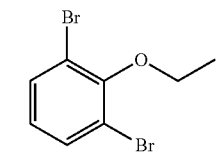

Formula Ve
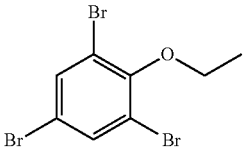

Thus the 1-ethoxy-4-bromobenzene used in the present process preferably having less than about 10 ppm of desethyl compound of Formula Va and/or less than 0.15% by weight of one or more positional isomers of Formula Vb, Vc, Vd and Ve by weight or molar ratio and provides the dapagliflozin of Formula I substantially free of impurities of Formula XIII and Formula XIV and desethoxy dapagliflozin of Formula XII.

Formula XIII
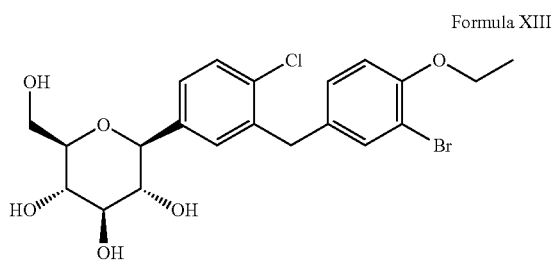

Formula XIV
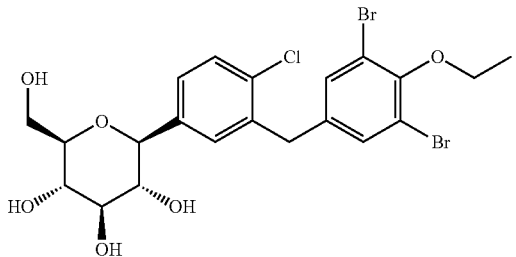

In another embodiment, the present invention provides dapagliflozin or its solvates or co-crystals thereof having less than about 10 ppm of desethyl dapagliflozin of Formula XII.

Formula XII
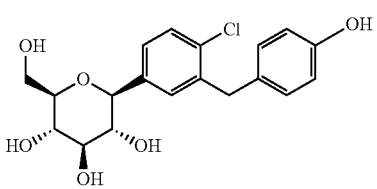

In another embodiment, the present invention provides dapagliflozin or its solvates or co-crystals thereof having less than about 0.15% of by weight of compounds of Formula XIII and/or compounds of Formula XIV.

Formula XIII
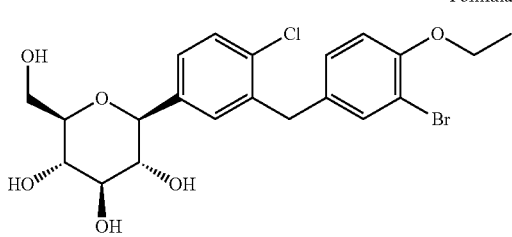

Formula XIV
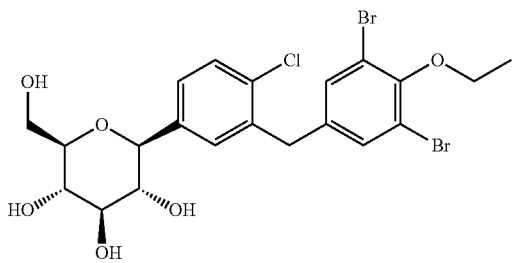

In one embodiment, the present invention provides a process for preparation of dapagliflozin of Formula I or its solvates or co-crystals thereof;

Formula I

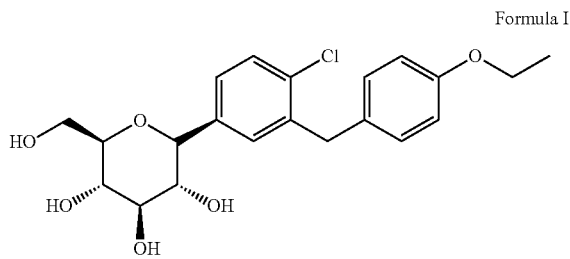

comprising:
a) reacting a compound of Formula VI or a reactive derivative thereof with a suitable amine source to obtain a compound of Formula VII;

Formula VI

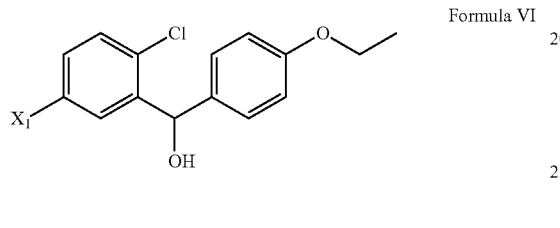

Formula VII

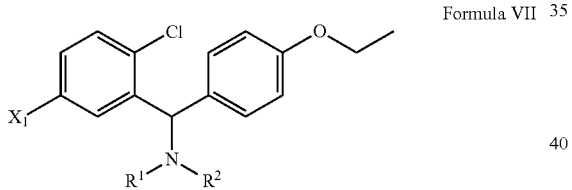

wherein "$X_1$" represents a suitable leaving group and $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring;

b) condensing the compound of Formula VII with glucono lactone of Formula VIII to obtain a compound of Formula IX'; wherein $R^1$ & $R^2$ are same as defined above and $P_1$, $P_2$, $P_3$, $P_4$ represents a suitable hydroxyl protecting group;

Formula VIII

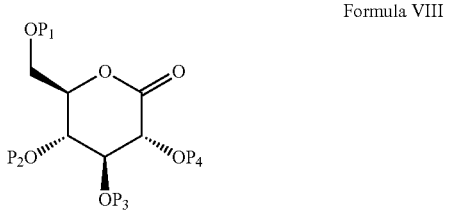

Formula IX'

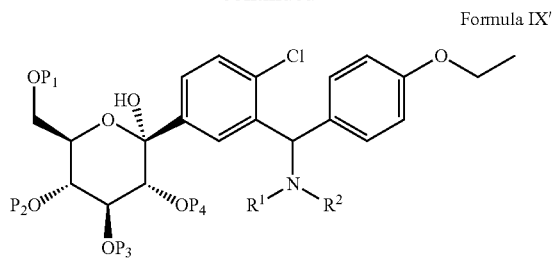

c) converting the compound of Formula IX' to a compound of Formula XI'; wherein $P_1$, $P_2$, $P_3$, $P_4$, $R^1$, and $R^2$ are same as defined above; and Formula XI'

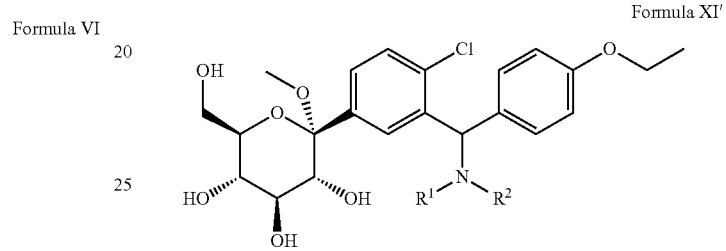

d) reducing the compound of Formula XI' with a suitable reducing agent to obtain dapagliflozin of Formula I.

The starting material of Formula VI is known in the art and can be prepared by any known method, for example WO 2011/051864 or alternatively, the starting material of Formula VI can be prepared according to the process of the present invention described herein above.

Step a) of the aforementioned process involves the reaction of a compound of Formula VI or its reactive derivative thereof with a suitable amine source to obtain compound of Formula VII; wherein "$X_1$" represents a suitable leaving group; $R^1$ and $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring.

Typically, the compound of Formula VI, wherein the "$X_1$" is a suitable leaving group, is first converted into its reactive derivative compound of Formula VIa' by treating with a suitable leaving group source to obtain a reactive derivative of compound of Formula VIa.

The suitable leaving group source includes, but are not limited to halogenating agents such as phosgene, oxalyl chloride, thionyl chloride, phosphorus oxychloride, phosphorous trichloride, phosphorus pentachloride, carbonyl dibromide, oxalyl bromide, thionyl bromide, phosphorous bromide and phosphorus oxybromide and the like; sulfonic acids, its halides or its anhydrides including but are not limited to methanesulfonic acid, benzenesulfonic acid, p-toluenesulfonic acid, trifluoromethane sulfonic acid, methanesulfonyl chloride, p-toluenesulfonyl chloride, trifluoromethane sulfonyl chloride, benzene sulfonyl chloride, methanesulfonic anhydride, p-toluenesulfonic anhydride, trifluoromethanesulfonic anhydride and the like; preferably the leaving group source is methanesulfonyl chloride.

In another embodiment, the compounds of Formula VI and Formula VIa used herein are represented as follows:

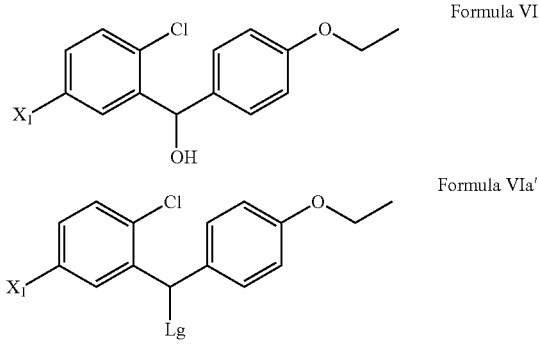

Formula VI

Formula VIa'

Wherein "X1" and Lg independently represents a suitable leaving group.

Conversion of compound of Formula VI into its reactive derivative compound of Formula VIa' is carried out in presence of a base and a suitable organic solvent at a temperature of about 0° C. to about 50° C.

The base used herein for the conversion of compound of Formula VI into a compound of Formula VIa' is selected from the group consisting of triethylamine, isopropyl ethylamine, diisopropyl amine, diisopropyl ethylamine, N-methyl morpholine, piperidine, pyridine and the like and mixtures thereof, preferably the base is triethyl amine.

The suitable organic solvent used herein for the conversion of compound of Formula VI in to a compound of Formula VIa' includes, but is not limited to halogenated hydrocarbons, ethers, amides and mixtures thereof. The halogenated hydrocarbons include, but are not limited to methylene chloride, ethylene chloride, chloroform and the like; ethers include, but are not limited to tetrahydrofuran, dimethyl ether, diisopropyl ether, methyl tertiary butyl ether, 1,4-dioxane and the like; amides include, but are not limited to dimethyl formamide, dimethyl acetamide and the like and mixtures thereof. Preferably the organic solvent is a mixture of methylene chloride and tetrahydrofuran.

The step a) reaction is carried out at a temperature of below room temperature; preferably the reaction is carried out at below 5° C. followed by raising the temperature about 25° C. to about 35° C. and maintained the reaction mass for a period of about 30 minutes to about 5 hours.

The resultant reactive derivative of compound of Formula VI thus formed can be isolated or further processed without isolating the reactive derivative in to next reaction with a suitable amine source to obtain compound of Formula VII, preferably it may be further processed in to next step without isolating the reactive derivative of compound of Formula VI.

In another embodiment, the present invention provides a compound of Formula VIa':

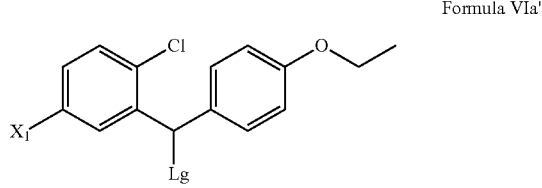

Formula VIa'

Wherein "$X_1$" and Lg independently represents a suitable leaving group.

In a preferred embodiment, the present invention provides a compound of Formula VIa1;

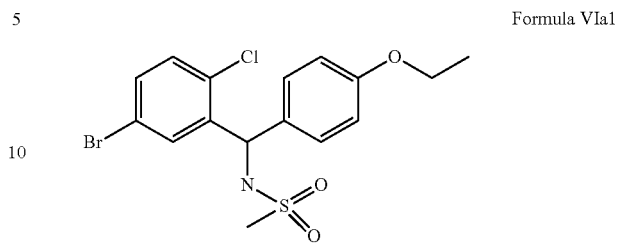

Formula VIa1

In a preferred embodiment, the compound of Formula VIa1 can be prepared according to the procedure described above with methane sulfonyl chloride as a suitable leaving group source.

Then, the reactive derivative of compound of Formula VIa' obtained according to the process described above is reacted with a suitable amine source in presence of a suitable base in a suitable solvent at a temperature of about 10° C. to reflux temperature to obtain a compound of Formula VII or a salt thereof.

The suitable amine source in the foregoing process may be a compound of Formula:

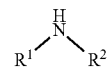

wherein $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring. The amine may be in the form of its free amine or its acceptable salt form for example hydrochloride salt.

The linear or branched alkyl group includes, but is not limited to methyl, ethyl, propyl, isopropyl, butyl, isobutyl, sec-butyl, tert-butyl, pentyl, hexyl, heptyl, octyl, nonyl, decyl group and the like; the linear or branched alkenyl group includes, but is not limited to an ethenyl or vinyl, propenyl or allyl,1-propenyl, n-butenyl, isobutenyl, 3-methylbut-2-enyl, n-pentenyl or hexenyl group and the like; the cycloalkyl includes, but is not limited to cyclopropyl, cyclobutyl, cyclopentyl, cyclohexyl, cyclooctyl and the like; an aryl group includes, but is not limited to phenyl, naphthyl and the like; an aralkyl group includes, but is not limited to benzyl, 1-phenylethyl and the like. The substituents on the aryl or aralkyl group may be selected from the group consisting of methyl, ethyl, propyl, methoxy, ethoxy, Br, Cl or I, nitro, amino, cyano, hydroxy, $CF_3$, $CCl_3$ and the like. The heterocyclic ring includes, but is not limited to morpholine, piperidine, pyrrolidine and the like.

Preferably, the amine source can be selected from the group consisting of diethylamine, diisopropylamine, di-n-propylamine, diallylamine, N-ethyl-N-phenylamine, diphenylamine, dibenzylamine, dicyclopropylamine, dicyclohexylamine, morpholine, piperidine, pyrrolidine and the like.

The suitable base used herein for the conversion of Formula VIa to a compound of Formula VII includes but is not limited to inorganic bases selected from alkali metal hydroxides such as lithium hydroxide, sodium hydroxide, potassium hydroxide and the like; alkali metal alkoxides such as sodium methoxide, sodium ethoxide, sodium tert-butoxide, potassium tert-butoxide and the like; alkali metal carbonates such as sodium carbonate, potassium carbonate, cesium carbonate and the like; alkali metal bicarbonates such as sodium bicarbonate, potassium bicarbonate and the like; organic bases selected from the group consisting of triethylamine, isopropyl ethylamine, diisopropyl amine, diisopropyl ethylamine, N-methyl morpholine, pyridine and the like; and mixtures thereof; Preferably the secondary amine $NHR_1R_2$ is selected from the group comprising of N,N-diethyl amine, N,N-diphenyl amine, N-ethyl-N-phenylamine, morpholine or piperidine; preferably the base is potassium carbonate.

The suitable solvent used herein for the conversion of Formula VIa to a compound of Formula VII includes but is not limited to nitriles, ethers, halogenated hydrocarbons, sulfoxides, ketones, amides and mixtures thereof. The nitriles include, but are not limited to acetonitrile, propionitrile and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride, chloroform and the like; sulfoxides include, but are not limited to dimethylsulfoxide, diethyl sulfoxide and the like; ketones include, but are not limited to acetone, methyl isobutyl ketone, methyl ethyl ketone and the like; amides include, but are not limited to dimethyl formamide, dimethyl acetamide, N-methyl pyrrolidinone and the like and mixtures thereof; preferably the suitable solvent is acetonitrile.

The step b) reaction is carried out at a temperature of about 20° C. to about 70° C. After completion of reaction, the resultant compound of Formula VII can be isolated as solid by known methods in the art.

The compound of Formula VII obtained according to the processes of above can be used as an intermediate or as a starting material in the preparation of dapagliflozin of Formula I.

In another embodiment, the present invention provides a compound of Formula VII;

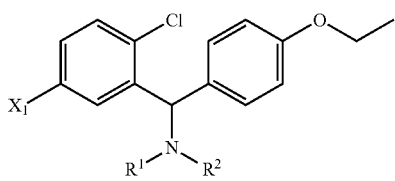

Formula VII wherein "$X_1$" represents a suitable leaving group and $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring.

In a preferred embodiment, the present invention provides a compound of Formula VII includes, but are not limited to a compound of Formula VIIa, VIIb, VIIc, VIId or VIIe;

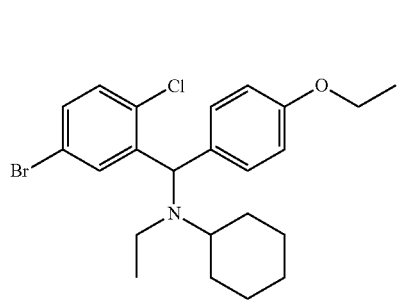

Formula VIIa

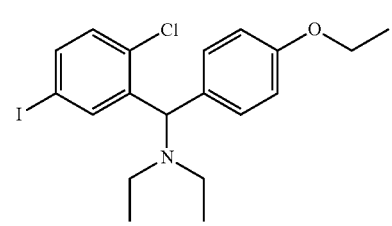

Formula VIIb

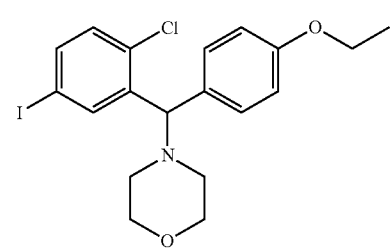

Formula VIIc

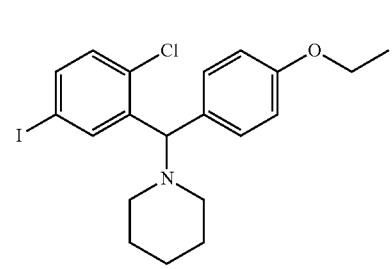

Formula VIId

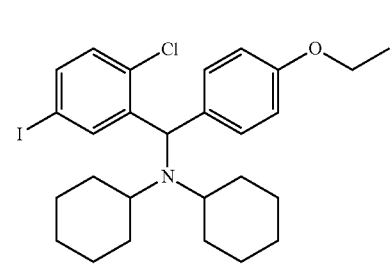

Formula VIIe

In another embodiment, the compound of Formula VII or a salt thereof can be used as an intermediate or as a starting material in the preparation of dapagliflozin of Formula I.

The compound of Formula VII obtained from the process described as above is converted in to a compound of Formula IX' by condensing compound of Formula VII with glucono lactone of Formula VIII, wherein the substituents "$P_1$", "$P_2$", "$P_3$" and "$P_4$" represents a "suitable hydroxyl protecting group" and $R^1$ and $R^2$ are defined as above, according to step b) of the aforementioned embodiment.

The step b) of the aforementioned process involves condensation of compound of Formula VII or a salt thereof with glucono lactone of Formula VIII to obtain a compound of Formula IX', wherein the substituents "$P_1$", "$P_2$", "$P_3$" and "P₄" represents a "suitable hydroxyl protecting group" and R¹ and R² are defined as above.

In another embodiment, the condensation reaction of compound of Formula VII with glucono lactone of Formula VIII may be carried out in presence of a base in a suitable solvent to obtain a compound of Formula IX'.

The base for step b) include, but are not limited to n-butyl lithium, sec-butyl lithium, tert-butyllithium, sodium hydride, potassium hydride, isopropylmagnesium chloride-lithium chloride complex, sec-butylmagnesium chloride lithium chloride complex, (trimethylsilyl) methyl lithium. Preferably, the base used is n-butyl lithium.

The solvent used herein for step b) includes but is not limited to ethers, aromatic hydrocarbons, alcohols, halogenated hydrocarbons and the like and mixtures thereof. The ethers include, but are not limited to tetrahydrofuran, dimethyl ether, diisopropyl ether, methyl tertiary butyl ether, 1,4-dioxane and the like; aromatic hydrocarbons include, but are not limited to toluene, xylene and the like; alcohols include, but are not limited to methanol, ethanol, isopropanol, n-propanol, t-butanol and the like; halogenated hydrocarbons include, but are not limited to methylene chloride, ethylene chloride, chloroform and the like; and mixture thereof; preferably the organic solvent is a mixture of toluene and tetrahydrofuran.

The step b) reaction is carried out at a temperature of about −80° C. to about 0° C. for about 1-5 hours. The resultant compound of Formula IX' thus formed can be isolated as a solid or proceed further without isolating the compound of Formula IX' in to subsequent reactions.

In another embodiment, the compound of Formula IX' thus obtained is used as such for the subsequent reactions without isolating from the reaction mass as solid.

In an embodiment, the present invention provides a glucono lactone of Formula VIII and a compound of Formula IX' as follows:

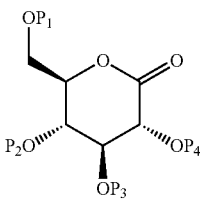

Formula VIII

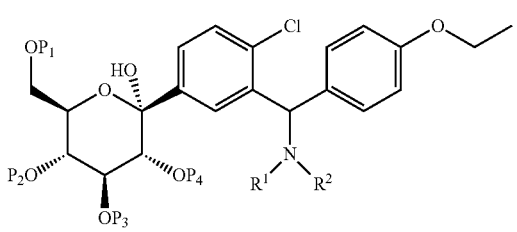

Formula IX' wherein the substituents "P", "P₁", "P₂", "P₃" and "P₄" represents hydrogen or a "suitable hydroxyl protecting group", wherein the hydroxyl protecting groups are selected from the group consisting of alkyl, allyl, pivaloyl, acetyl (Ac), tosyl (Ts), mesyl (Ms), trimethylsilyl (TMS), triethylsilyl (TES), triisopropylsilyl (TIPS), tertiary butyldimethylsilyl (TBS), 2-(trimethylsilyl) ethoxymethyl (SEM), benzyl (Bn), para-methoxybenzyl (PMB), trityl (Tr), para-bromobenzoyl, para-nitrobenzoyl, benzoyl (Bz), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), and the like. Further, the protecting group for hydroxyl groups may form acetal or silyl acetal together with adjacent hydroxyl groups; preferably the hydroxyl protecting group is trimethyl silyl group and R¹ & R² are defined as above.

In a preferred embodiment, the glucono lactone of Formula VIIIa can be represented as follows:

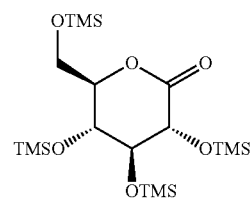

Formula VIIIa

In a still further preferred embodiment, the present invention provides a compound of Formula IX includes, but are not limited to a compound of Formula IX'a, IX'b, IX'c or IX'd;

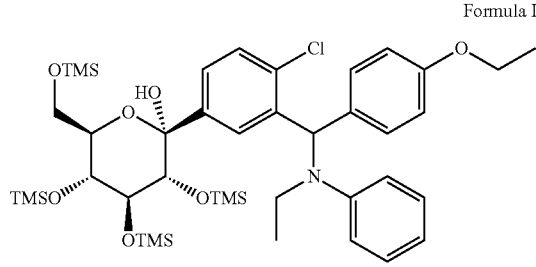

Formula IX'a

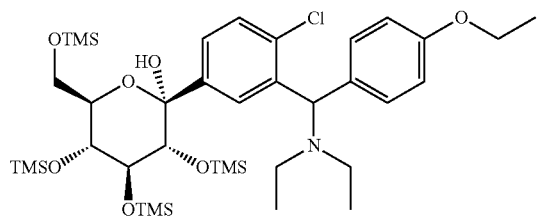

Formula IX'b

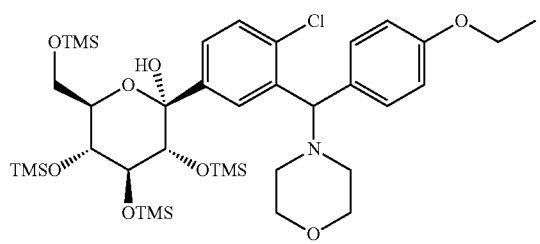

Formula IX'c

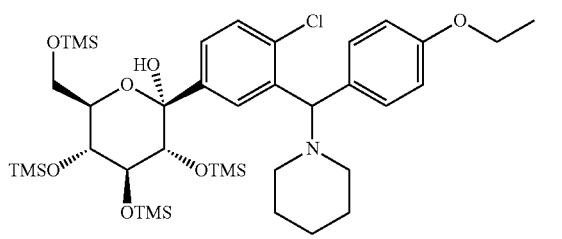

Formula IX'd

In another embodiment, the compound of Formula IX' or a salt thereof thus obtained can be used as an intermediate or as a starting material in the preparation of dapagliflozin of Formula I.

The compound of Formula IX' obtained from the process described as above is converted in to the compound of Formula XI' by glycosidation of compound of Formula IX', wherein the substituents "$P_1$", "$P_2$", "$P_3$" and "$P_4$" represents a "suitable hydroxyl protecting group" and $R^1$ and $R^2$ are defined as above, with a suitable acid according to step c) of aforementioned embodiment.

The step c) of the aforementioned process involves the conversion of compound of Formula IX' to a compound of Formula XI', wherein the substituents "$P_1$", "$P_2$", "$P_3$" and "$P_4$" represents a "suitable hydroxyl protecting group" and $R^1$ and $R^2$ are defined as above.

The conversion of compound of Formula IX' to compound of Formula XI' involves glycosidation of compound of Formula IX' with a glycosidation reagent in presence of a nucleophilic compound such as an alcohol, preferably with methanol in presence of a suitable solvent to obtain the compound of Formula XI' or a salt thereof. The acid used in glycosidation is capable of facilitating deprotection of the hydroxyl groups through the removal of the protecting groups "$P_1$", "$P_2$", "$P_3$" and "$P_4$" and substitute the hydroxyl group at the anomeric carbon site with an alcohol.

The glycosidation reagent used herein is selected from an organic acid such as formic acid, acetic acid, trifluoroacetic acid, methanesulfonic acid and the like; an inorganic acid such as hydrochloric acid, sulfuric acid, nitric acid and the like; and a Lewis acid such as boron trifluoride diethyletherate, scandium (III) trifluoromethanesulfonate, titanium (IV) isopropoxide, tin (IV) chloride, zinc (II) bromide, and zinc (II) chloride; preferably the glycosidation reaction is carried out by using methane sulfonic acid or hydrochloric acid gas in methanol medium.

The solvent used herein for the glycosidation reaction of step c) includes but is not limited to alcohols, ethers, aromatic hydrocarbons, halogenated hydrocarbons and the like and mixtures thereof. Alcohols include, but are not limited to methanol, ethanol, isopropanol, n-propanol, t-butanol and the like; ethers include, but are not limited to tetrahydrofuran, dimethyl ether, diisopropyl ether, methyl tertiary butyl ether, 1,4-dioxane and the like; aromatic hydrocarbons include, but are not limited to toluene, xylene and the like; halogenated hydrocarbons include, but are not limited to methylene chloride, ethylene chloride, chloroform and the like; and mixture thereof; preferably the organic solvent is a mixture of toluene and tetrahydrofuran.

The glycosidation reaction is carried out at a temperature of about −80° C. to about 50° C. for about 1-20 hours. After completion of the reaction, the resultant compound of Formula IX can be isolated by known methods in the art for example adjusting pH of the reaction mass to neutral or basic with a suitable base followed by separating the product containing organic layer and removal of solvent.

The suitable base for neutralizing the reaction mass include, but is not limited to sodium hydroxide, potassium hydroxide, ammonium hydroxide, sodium methoxide, sodium ethoxide, sodium carbonate, potassium carbonate, cesium carbonate, sodium bicarbonate, potassium bicarbonate and the like and mixtures thereof.

The resultant compound of Formula XI' thus formed can be isolated as a solid or proceed further without isolating the compound of Formula XI' in to subsequent reactions. Preferably the compound of Formula XI' is isolated as a solid from the reaction mass by using cyclic hydrocarbons as a solvent, for example, n-heptane.

In another embodiment, the present invention provides a compound of Formula XI';

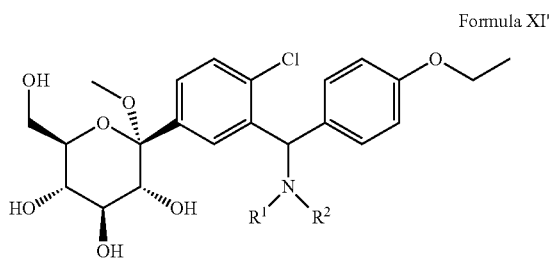

Formula XI' wherein $R^1$ & $R^2$ independently represents hydrogen; a linear or branched alkyl group, a linear or branched alkenyl group, a cycloalkyl group, substituted or unsubstituted aryl group or substituted or unsubstituted aralkyl group; or $R^1$ and $R^2$ together with the nitrogen atom to which they are attached to form a heterocyclic ring.

In preferred embodiment, the present invention provides a compound of Formula XI' includes, but are not limited to a compound of Formula XI'a, XI'b, XI'c or XI'd;

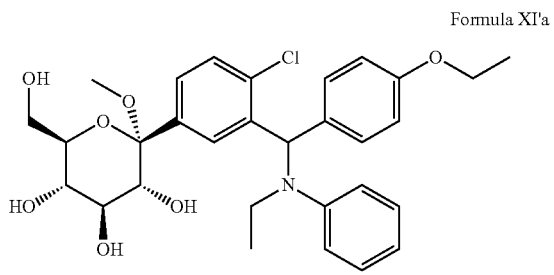

Formula XI'a

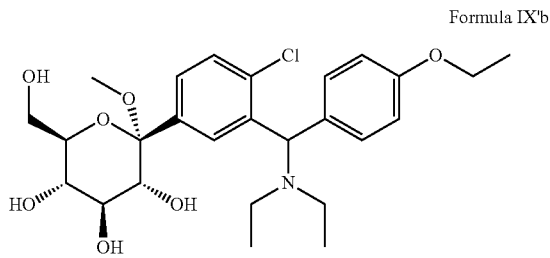

Formula IX'b

Formula XI'c

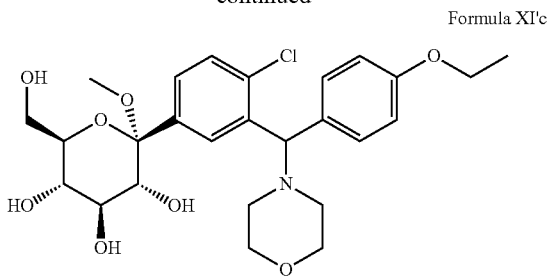

Formula XI'd

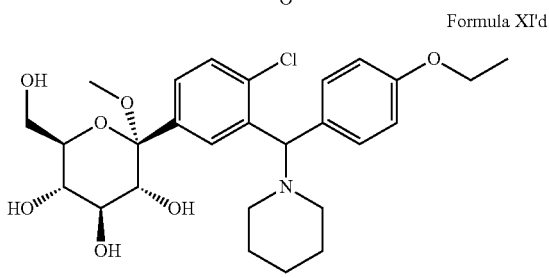

In another embodiment, the compound of Formula XI' or a salt thereof thus obtained can be used as an intermediate or as a starting material in the preparation of dapagliflozin of Formula I or its solvates or co-crystals thereof.

Step d) of aforementioned embodiment, involves the reduction of the compound of Formula XI' with a suitable reducing agents to obtain dapagliflozin of Formula I, wherein the reduction reaction is carried out with a suitable reducing agent in presence of a solvent.

The reducing agent and the solvent used herein for the reduction of compound of Formula XI' to dapagliflozin of Formula I are same as to the reducing agent and the solvent used above during the reduction of compound Formula XI to dapagliflozin of Formula I.

After completion of the reaction, the resultant dapagliflozin of Formula I can be isolated by known methods in the art for example adjusting pH of the reaction mass to neutral or basic with a suitable base followed by separating the product containing organic layer and removal of solvent. Optionally, the resultant dapagliflozin can be converted in to its co-crystal form with a suitable co-crystal former or its solvates with a suitable solvent as an intermediate in the preparation of pure dapagliflozin as mentioned above.

The X-Ray powder diffraction can be measured using PANalytical X'per³pro X-ray powder Diffractometer equipped with a Cu-anode ([λ]=1.54 Angstrom), X-ray source operated at kV, 40 mA. Two-theta calibration is performed using an NIST SRM 640c Si standard. The sample was analyzed using the following instrument parameters: measuring range=3-45° 2θ; step size=0.01°; and Time per step=48 sec.

In another embodiment, the present invention provides dapagliflozin obtained by the above process, as analyzed using high performance liquid chromatography ("HPLC") with the conditions are tabulated below:

| Column | Kinetex XB C18 (150 × 4.6) mm 2.6 um |
| --- | --- |
| Column temperature | 50° C. |
| Mobile phase | Mobile phase-A: Buffer:Methanol (90:10, v/v) |
| | Mobile phase-B: water:Methanol (10:90, v/v) |
| Buffer | 0.01M KH2PO4 in 1 L Milli-Q-water, pH adjusted to 3.0 with orthophosphoric acid (~10%, v/v) |
| Diluent | Buffer:Methanol (50:50, v/v) |
| Flow rate | 0.7 mL/min |
| Wave length | By UV at 225 nm |
| Injection volume | 10 µL |
| Elution mode | gradient |

As used herein the word "substantially free" refers to dapagliflozin having less than 0.1% of one or more of process impurities by HPLC, preferably less than 0.08% by HPLC.

In accordance with another embodiment, the present invention provides a pharmaceutical composition comprising dapagliflozin or its solvates or co-crystals thereof, prepared by the processes of the present invention and at least one pharmaceutically acceptable excipient.

EXAMPLES

The following non limiting examples illustrate specific embodiments of the present invention. They are not intended to be limiting the scope of the present invention in any way.

Example-1: Preparation of Amide Compound of Formula III (Wherein X=Bromo)

5-bromo-2-chloro benzoic acid (100 gms) and methylene chloride (900 ml) were added in to a round bottom flask and stirred for 5 mins at 25-35° C. N,O-dimethyl hydroxyl amine hydrochloride (49.73 gms) and diethyl amine (34.21 gms) were added to the reaction mass and allowed to cool to 5-10° C. Dicyclohexyl carbodiimide solution (131.62 gms in 100 ml of methylene chloride) was added to the reaction mass, stirred for 30 mins, filtered and washed with methylene chloride. The filtrate was washed with aqueous sodium bicarbonate solution, aqueous sodium chloride solution, the organic layer was concentrated and isolated the title compound in heptane as white solid. Yield: 88 gms.

Example-2: Preparation of 5-Halo-2-Chloro Benzaldehyde Compound of Formula IV (Wherein X=Bromo)

Amide compound of Formula III (wherein X=bromo; 88 gms) and toluene (440 ml) were added in to a round bottom flask at 25-35° C. and allowed to cool to −65° C. to −70° C. Diisobutyl aluminium hydride (1 Lt, 25% solution in toluene) was added to the reaction mass and stirred for 30 min at same temperature. The reaction mass was quenched with aqueous sodium potassium tartrate solution and heated the reaction mass to 25-35° C. The layers were separated and the aqueous layer was extracted with toluene then the organic layers were combined and washed with aqueous sodium chloride and dried over sodium sulphate. The organic layer was concentrated under reduced pressure at 45° C. and the obtained residue was diluted in heptane (200 ml) and allowed to cool to 5-10° C. The reaction mass was stirred for 1-2 hrs at 5-10° C., filtered, washed with chilled heptane and dried at 30-35° C. to get the title compound. Yield: 65 gms.

Example-3: Preparation of 5-Halo-2-Chloro-1-(4-Ethoxy Phenyl) Methanol Compound of Formula VI-I (Wherein X=Bromo)

4-bromo phenetole (398.53 gms) and tetrahydrofuran (3000 ml) were added into a round bottom flask at 25-35° C. and allowed to cool to −70 to −80° C. To this solution, n-butyl lithium in hexane (1.6M, 854.34 ml) was added slowly at −70 to −80° C. and stirred for 30 mins. Compound of Formula II (wherein X=bromo, 300 gms) in tetrahydrofuran (900 ml) was added to the above reaction mass slowly at −80 to −90° C. and maintained for 2-4 hrs at the same temperature. The reaction mass was treated with aq ammonium chloride solution (0.5 gms of ammonium chloride in 5 ml of water), stirred for 30 mins at 25-35° C. The organic layer was separated and the aqueous layer was extracted with ethyl acetate. Combined the organic layer, washed with water and concentered the organic layer up to 300 ml under reduced pressure at below 50° C. The resulting reaction mass was co-distilled with cyclohexane (900 ml) up to 300 ml twice and cooled the reaction mass to 25-35° C. 10% IPA in cyclohexane (900 ml) was added to the above reaction mass at 25-35° C. and raised the reaction mass temperature to 70-80° C. to get clear solution. The solution was cooled to 25-35° C. and stirred for 4-5 hrs, filtered, washed with cyclohexane and dried the material at 50-55° C. HPLC analysis revealed the content of impurity of Formula A: about 4 to 5%; impurity of Formula B: about 2 to 3%; impurity of Formula C: about 0.5% and impurity of Formula D: about 0.5 to 1%.

10% IPA in cyclohexane (900 ml) was added to the above material at 25-35° C., heated to 70-80° C. and maintained for 15-30 mins. The resulting solution was cooled to 25-35° C. and maintained for 4 hrs, filtered, washed with cyclohexane and dried at 50-55° C. under vacuum for 4 hrs to obtain the title compound. Yield: 225 gms; HPLC Purity: 99.0%; impurity of Formula A: less than 0.5%; impurity of Formula B: less than 0.1%; impurity of Formula C: less than 0.1% and impurity of Formula D: less than 0.2%.

1H NMR (300 MHz, CDCl$_3$) δ=7.17 (d, 1H), 7.33 (dd, 1H), 7.86 (d, 1H), 6.06 (d, 1H), 7.26 (m, 2H), 6.84 (m, 2H), 4.01 (q, 2H), 1.39 (t, 3H), 2.30 (d, OH); MS (ESI)[M+H]:− 340 The PXRD is set forth in FIG. 1.

Example-4: Preparation of Dimethoxy Dapagliflozin Compound of Formula XIa 5-halo-2-chloro-1-(4-ethoxy phenyl) methanol compound of Formula VI-I (wherein X=bromo; 230 gms) and methylene chloride (2300 ml) were added into a round bottom flask at 25-35° C. and stirred for 10 mins. To this solution, triethyl amine (136.25 gms) was added at 25-35° C., stirred for 10 mins and then trimethylsilyl chloride (109.71 gms) was added slowly at 25-35° C., stirred for 4 hrs and cooled to 0-10° C. Water (115000 ml) was added to the resulting reaction mass, the temperature was raised to 25-35° C. and the layers were separated. The organic layer was washed with 10% sodium phosphate monobasic dihydrate solution, stirred the reaction mass and the layers were separated. The organic layer was distilled completely under reduced pressure at below 35° C. Toluene (690 ml) was added to the resulting residue and distilled the solvent completely under reduced pressure at below 50° C. To the residue, toluene (1150 ml) and tetrahydrofuran (575 ml) were added at 25-35° C. The reaction mass was cooled to −80 to −90° C., n-butyl lithium solution (504.91) was added slowly at −80 to −90° C. and stirred for 90 mins. To the resulting reaction mass, 2,3,4,6-tetrakis-O-trimethylsilyl-ß-D-glucolactone solution (377. 19 gms dissolved in 690 ml of toluene) was added slowly at −80 to −90° C. and stirred for 2 hrs. To the reaction mass, pre-cooled methane sulfonic acid solution which is formed by dissolving 194 gm of methane sulfonic acid in 690 ml of methanol was added at −80 to −90° C. for 60 min. The temperature of the reaction mass was raised to 25-35° C. and stirred for 4 hrs at 25-35° C. The reaction mass was cooled to 0-5° C., saturated sodium bicarbonate solution was added to the reaction mass (220 gm of sodium bicarbonate dissolved in 2760 ml of water) at 0-5° C. The temperature of the reaction mass was raised to 25-35° C., settled and separated the layers. The aqueous layer was extracted with toluene and combined the organic layers. The combined organic layer was concentrated upto 230 ml under reduced pressure at below 50° C. The resulting reaction mass was co-distilled with cyclohexane (690 ml) up to 230 ml. The resulting reaction mass further treated with cyclohexane (690 ml) and distilled the solvent completely under reduced pressure at below 50° C. HPLC analysis revealed the content of impurity of Formula F: about 4 to 4.5%; Impurity of Formula G: about 2.5 to 3%.

t-butyl methyl ether (920 ml) was added to the above reaction mass at 25-35° C. and stirred for 30 mins to get the clear solution at 25-35° C. The resulting solution was added to precooled cyclohexane (4600 ml) 15° C. and maintained for 2 hrs, filtered, washed with cyclohexane and dried at 25-53° C. under vacuum for 5 hrs to obtain the title compound. Yield: 253 gms; HPLC Purity: 88%; impurity of Formula F: less than 2%; impurity of Formula G: less than 1%.

1H NMR (300 MHz, DMSO-d6) δ=7.832-7.756 (dd, 1H), 7.458-7.424 (dd, 1H), 7.347-7.342 (d, 1H), 7.261-7.174 (dd, 2H), 6.880-6.822 (dd, 2H), 5.509-5.492 (d, 1H), 4.990-4.971 (d, 1H), 4.876-4.745 (dd, 2H), 4.575-4.555 (t, 1H), 4.041-3.992 (m, 3H), 3.969-3.946 (d, 1H), 3.595-3.550 (m, 2H), 3.262-3.240 (m, 4H), 2.975-2.921 (d, 3H), 2.894-2.890 (m, 1H), 1.319-1.292 (t, 3H); MS (ESI-ve): m/z=515 [M+2Na]$^+$

Figure 2:
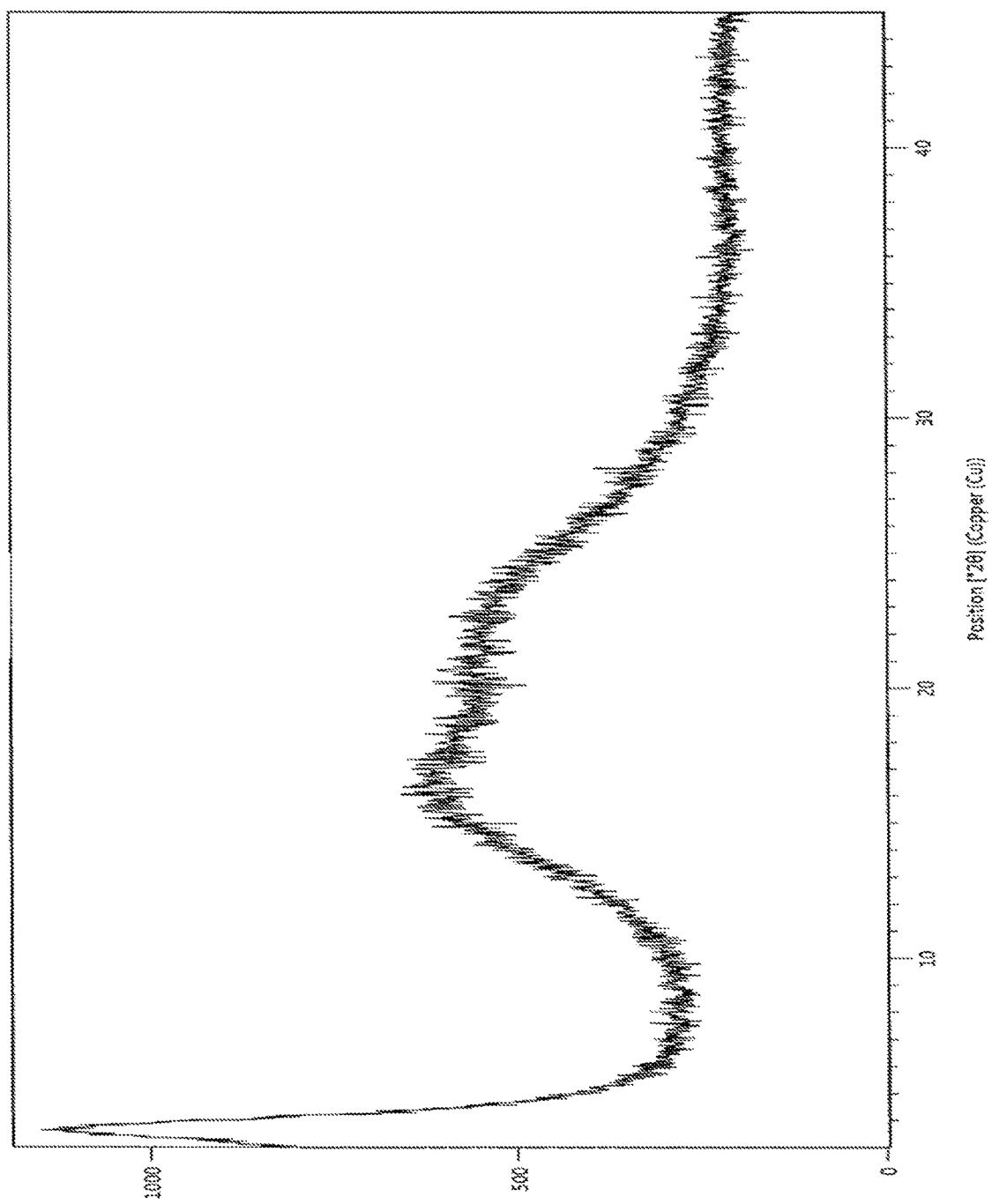
FIG. 02 is the PXRD spectrum of compound of Formula IXa1

The PXRD is set forth in FIG. 2.

Example-5: Preparation of Dapagliflozin DL-Pipecolic Acid Co-Crystals

Dimethoxy dapagliflozin of Formula XIa (253 gms), methylene chloride (2300 ml), acetonitrile (460 ml) and triethyl silane (391.42 gms) were added into a round bottom flask at 25-35° C. The reaction mass was cooled to −40 to −50° C. and boron trifluoride diethyl etherate (477.77 gms) was added slowly at −45 to −50° C. The temperature of the reaction mass was raised to 0-5° C. and stirred for 2 hr and quenched with aqueous sodium bicarbonate solution. The temperature of reaction mass was raised to 25-35° C., stirred for 10 mins and separated the layers. The aqueous layer was extracted with methylene chloride and combined the organic layers. 10% sodium chloride was added to the resulting combined organic layer, maintained for 40 mins and separated the layers. The organic layer was distilled completely under reduced pressure at below 30° C. Ethyl acetate (690 ml) was added to the reaction mass and distilled completely under reduced pressure at below 50° C. To the resulting reaction mass ethyl acetate (2300 ml) and DL-pipecolic acid (69.56 gms) were added at 25-35° C. The temperature of the reaction mass raised to 70-80° C., maintained for 2 hrs. The reaction mass was cooled to 25-35° C., maintained for 46 hrs, filtered, washed with ethyl acetate and dried at 50° C. for 8 hrs.

Ethyl acetate (10 ml), water (5 ml) and ammonia solution (0.15 ml) were added to the resulting dapagliflozin DL-pipecolic acid co-crystals at 25-35° C., stirred the reaction mass for 15-30 mins and separated the layers. The aqueous layer was extracted with ethyl acetate at 25-35° C. and the combined organic layers were washed with brine followed by drying over sodium sulphate. The organic layer was distilled under reduced pressure completely at below 50° C.

Ethyl acetate was added to the resulting material and distilled off solvent completely under reduced pressure at below 50° C., cooled to 25-35° C. To the resulting material ethyl acetate (10 vl) and DL-pipecolic acid (0.26 gms) were added at 25-35° C. The temperature of reaction mass was raised to 70-80° C., cooled to 25-35° C., maintained for 22 hrs, filtered, washed with ethyl acetate and dried at 50° C. to obtain title compound. Yield: 109 gms.

HPLC Purity: 99.8%; α-anomer impurity of Formula H: less than 0.1%; dimer impurity of Formula J: less than 0.1%

Mass Spectrum (ESI+ve): m/z=538.540 [M+H]$^+$

1H NMR (300 MHz, DMSO-d6) δ=8.253 (bs, 1H), 7.377-7.314 (dd, 2H), 7.214-7.207 (d, 1H), 7.105-7.076 (d, 2H), 6.838-6.809 (d, 2H), 5.025-4.031 (m, 4H), 3.999-3.917 (m, 4H), 3.706-3.667 (d, 1H), 3.469-3.048 (m, 9H), 2.749-2.710 (m, 1H), 2.036-1.395 (m, 6H), 1.316-1.270 (t, 3H)

Figure 3:
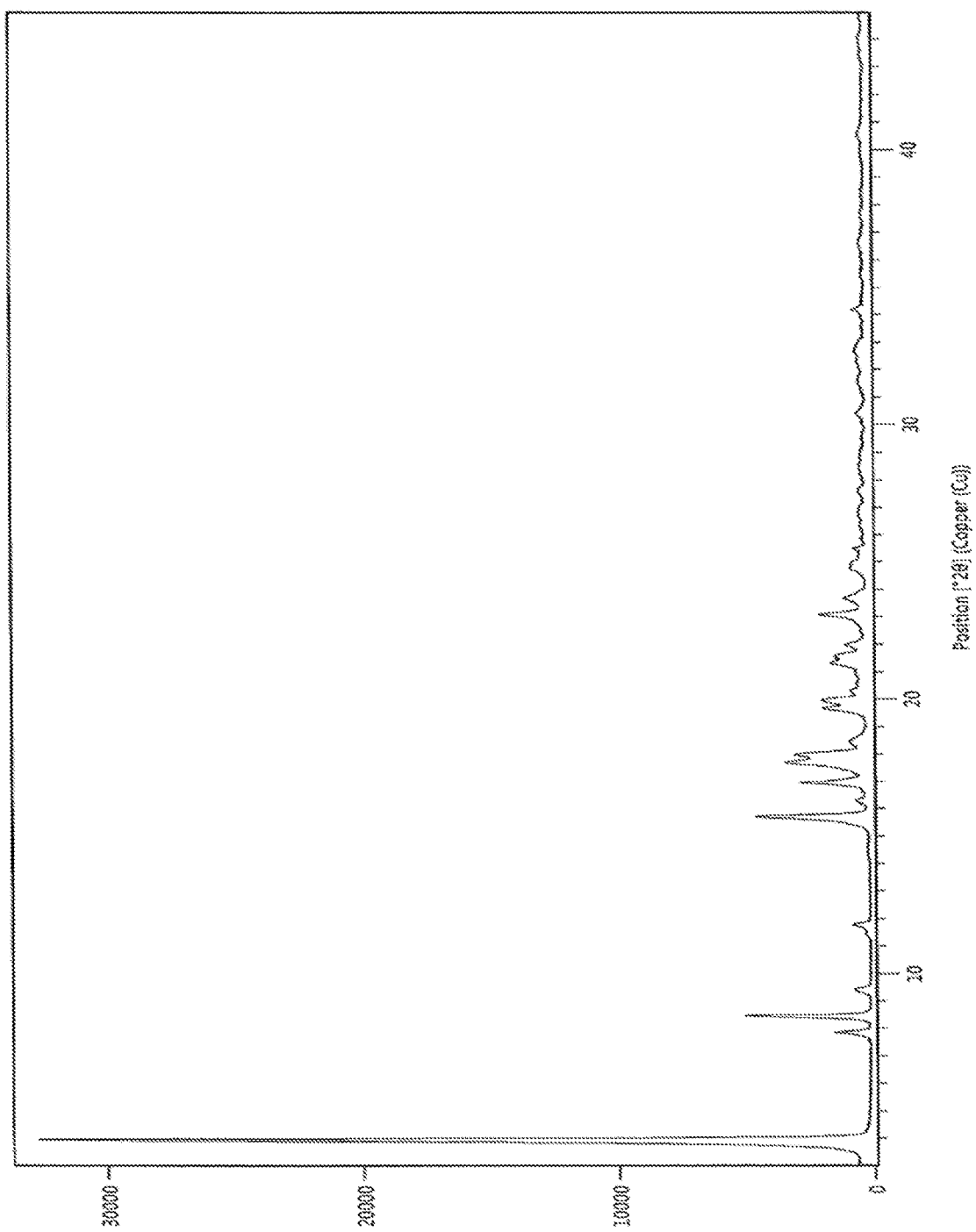
FIG. 03 is the PXRD pattern of dapagliflozin DL-pipecolic acid co-crystals.

The PXRD is set forth in FIG. 3.

Example-6: Preparation of Amorphous Dapagliflozin

Dapagliflozin DL-pipecolic acid co-crystals (100 gms) was added to ethyl acetate (1000 ml) and water (500 ml) at 25-35° C., stirred the reaction mass and separated the layers. The organic layer was washed with water (4*500 ml) and combined the organic layers. The combined organic layer was distilled under reduced pressure completely at below 50° C. The resulting residue was treated with n-heptane (500 ml) at below 50° C., stirred the reaction mass for 10-15 mins and distilled out n-heptane completely at below 50° C. The resulting residue was cooled to 25-35° C. and was treated with t-butyl methyl ether (500 ml), stirred for 15-30 min to get the clear solution at 25-35° C. The resulting solution was added to the pre-cooled n-heptane (3000 ml) at −8 to 2° C. and stirred for 2 hrs. The solids were filtered and washed with mixture of chilled t-butyl methyl ether (10 ml) & n-heptane (50 ml). The solids were dried initially under vacuum at 25-31° C. for 12 hrs, later dried at 31-37° C. for 12 hrs and finally dried at 37-43° C. for 12 hrs to obtain amorphous Dapagliflozin. Yield: 50 gms, HPLC Purity: 99.8%.

Example-7: Preparation of Amorphous Dapagliflozin

Dapagliflozin DL-pipecolic acid co-crystals (100 gms) was added to ethyl acetate (1000 ml) and water (500 ml) at 25-35° C., stirred the reaction mass and cooled to 10-15° C. The reaction mass pH was adjusted to 8.0-9.0 with aqueous ammonia at 10-15° C. The temperature of the reaction mass was raised to 25-35° C., stirred for 15 mins and separated the layers. The aqueous layer was extracted with ethyl acetate at 25-35° C. and the combined organic layers were washed with brine followed by drying over sodium sulphate. The organic layer was distilled under reduced pressure completely at below 50° C. The resulting residue was treated with methanol (200 ml) at below 50° C. and distilled off methanol completely at below 50° C. To the resulting residue, methanol (250 ml) was added and stirred for 10 min to get the clear solution at 25-35° C. The resulting methanol solution was added slowly into chilled water at 2-6° C. and stirred for 24 hrs at 2-6° C. The solids were filtered and washed with chilled water (100 ml). The solids were dried under vacuum at 45-50° C. for 16 hrs to obtain amorphous Dapagliflozin. Yield: 60 gms.

Example-8: Preparation of Compound of Formula VIa1 (Wherein X=Bromo)

5-halo-2-chloro-1-(4-ethoxy phenyl) methanol compound of Formula VI (wherein X=bromo; 60 gms) was added to a mixture of methylene chloride (300 ml) and tetrahydrofuran (300 ml) at 25-35° C. The contents were stirred for 10 min at 25-35° C. To this solution, triethylamine (53.5 gms) was added at 25-35° C., cooled to 0-5° C. and then mesyl chloride (80 gms) was added slowly over 20 min at below 5° C. The temperature of the reaction mass was raised to 25-35° C. and stirred for 1 hr at 25-35° C. After reaction completion, the inorganics were filtered and washed with tetrahydrofuran (120 ml). The reaction mass was distilled under reduced pressure at below 25° C. to obtain the residue as an oil. Yield: 180 gms.

Example-9: Preparation of Compound of Formula VIIa (Wherein X=Bromo)

5-halo-2-chloro-1-(4-ethoxy phenyl) methanol compound of Formula VI (wherein X=bromo; 60 gms) was added to a mixture of methylene chloride (300 ml) and tetrahydrofuran (300 ml) at 25-35° C. The contents were stirred for 10 min at 25-35° C. To this solution, triethylamine (53.5 gms) was added at 25-35° C., cooled to 0-5° C. and then mesyl chloride (80 gms) was added slowly over 20 min at below 5° C. The temperature of the reaction mass was raised to 25-35° C. and stirred for 1 hr at 25-35° C. After reaction completion, the inorganics were filtered and washed with tetrahydrofuran (120 ml). The reaction mass was distilled under reduced pressure at below 25° C. to obtain the residue (180 gms) as an oil. To the residue, acetonitrile (600 ml) was added, potassium carbonate (121.8 gms) was added at 25-35° C. and stirred for 10 min. N-ethyl-N-phenylamine (64.1 gms) was added slowly over 20 min at 25-35° C. and the reaction mass was heated to 50-55° C. and stirred for 2 hrs at 50-55° C. After reaction completion, the inorganics were filtered and washed with acetonitrile (180 ml). The reaction mass was distilled under reduced pressure at below 40° C. and allowed to cool to 25° C. To the reside, methylene chloride (600 ml) and water (600 ml) were added and stirred for 15 min at 25-35° C. The layers were separated and aqueous layer was extracted with methylene chloride (600 ml). The organic layers were combined and washed with water, 10% brine solution followed by drying the organic layer over sodium sulphate. The organic layer was distilled under reduced pressure completely at below 50° C. and then acetonitrile (120 ml) was added and allowed to cool to 0-5° C. The reaction mass was stirred for 1 hr at 0-5° C., filtered, washed with acetonitrile (60 ml) and dried at 45-50° C. to obtain title compound as white solid. Yield: 36 gms;

1H NMR (300 MHz, DMSO-d6) δ=7.539-7.503 (dd, 1H), 7.450-7.422 (d, 1H), 7.254-7.246 (d, 1H), 7.174-7.080 (m, 4H), 6.921-6.892 (d, 2H), 6.696-6.628 (m, 3H), 6.160 (s, 1H), 4.041-3.972 (q, 2H), 3.403-3.281 (m, 4H), 1.337-1.291 (t, 3H), 0.756-0.710 (t, 3H); MS (ESI)[M+H]:−445

Example—10-13

Compounds of Formula VIIb, VIIc, VIId and VIIe were prepared from a compound of Formula VI (wherein X=Iodo) with an appropriate amine compound analogous to procedure as described in Example 4 and the results tabulated as in Table 1:

TABLE 1

| Input | Amine | Yield | Analysis |
|---|---|---|---|
| Formula VI (X = Iodo) 92 gms | Diethylamine 86.5 gms | Formula VIIb (65 gms) | Mass Spectrum (ESI⁺): m/z = 444[M + H]⁺ 1H NMR (300 MHz, CDCl$_3$-d6) δ = 8.177-8.169 (d, 1H), 7.402-7.293 (m, 3H), 6.980-6.952 (d, 1H), 6.818-6.769 (m, 2H), 5.022 (s, 1H), 4.016-3.946 (q, 2H), 2.643-2.498(m, 4H), 1.400-1.353 (t, 3H), 0.959-0.911 (t, 3H) |
| Formula VI (X = Iodo) 10 gms | Morpholine 9 gms | Formula VIIc (7 gms) | Mass Spectrum (ESI⁺): m/z = 458[M + H]⁺ 1H NMR (300 MHz, DMSO-d6) δ = 8.110-8.103 (d, 1H), 7.589-7.5547 (dd, 1H), 7.257-7.161 (dd, 3H), 6.883-6.854 (d, 2H), 4.562 (s, 1H), 4.000-3.930 (q, 2H), 3.599-3.570 (t, 4H), 2.307-2.168 (dt, 4H), 1.309-1.263 (t, 3H) |
| Formula VI (X = Iodo) 10 gms | Piperidine 8.75 g | Formula VIId (7 gms) | Mass Spectrum (ESI⁺): m/z = 456[M + H]⁺ 1H NMR (300 MHz, DMSO-d6) δ = 8.087-8.080 (d, 1H), 7.567-7.532 (dd, 1H), 7.218-7.141 (dd, 3H), 6.868-6.839 (d, 2H), 4.529 (s, 1H), 3.997-3.928 (q, 2H), 3.599-3.570 (t, 4H), 2.220-2.204 (dt, 4H), 1.491-1.397 (m, 6H), 1.309-1.262 (t, 3H) |
| Formula VI (X = Iodo) 10 gms | Dicyclohexyl amine 18.55 g | Formula VIIe (7.1 gms) | 1H NMR (300 MHz, DMSO-d6) δ = 8.089-8.082 (d, 1H), 7.581-7.546 (dd, 1H), 7.112-6.982 (dd, 3H), 6.832-6.803 (d, 2H), 5.494 (s, 1H), 3.990-3.921 (q, 2H), 2.690 (t, 2H), 3.599-1.683-0.939 (m. 24H) |

Example—14: Preparation of Compound of Formula X'a

Compound of Formula VIIa (50 gms) was dissolved in a mixture of toluene (25 0 ml) and tetrahydrofuran (250 ml) at 25-35° C. under nitrogen atmosphere. The reaction mass was cooled to −68 to −78° C., n-butyl lithium (15.6 gms) was added slowly at −68 to −78° C. over 1 hr and stirred for 30 min at −78° C. After reaction completion, 2,3,4,6-tetra-O-trimethylsilyl-ß-D-glucolactone solution (63 gms dissolved in 200 ml of toluene) was added slowly at −78° C. for 1.5 hr, stirred for 120 min at −78° C. and cooled to −20° C. 20% Ammonium chloride solution (200 gms dissolved in 1000 ml of water) was added to the reaction mass at −20 to 10° C. in 30 min. The reaction mass was raised to 25-35° C., settled and the layers were separated. The aqueous layer was extracted with toluene, combined the organic layers and washed with water, 5% brine and dried over sodium sulphate. The organic layer was distilled completely under reduced pressure at below 50° C. and degassed the residue under vacuum for 30 min to obtain residue as oil (100 gms). To the residue, tetrahydrofuran (500 ml) and citric acid solution (50 gms dissolved in 500 ml) was added slowly at 25-35° C. over 1 hour and stirred for overnight. After reaction completion, tetrahydrofuran was distilled completely under reduced pressure at below 50° C. Ethyl acetate (1000 ml) was added to the reaction mass, cooled to 0-5° C. and pH adjusted to 7.5-8.0 by liq ammonia at 0-5° C. The reaction mass was raised to 25-35° C., settled and separated the layers. The aqueous layer was extracted with ethyl acetate and the resulting organic layer was washed with water, 5% brine solution followed by drying over sodium sulphate. The organic layer was distilled completely under reduced pressure at below 50° C. and purified by silica gel in ethyl acetate-hexane mixture to obtain title compound as pale yellow solid. Yield: 25 gms

Example—15: Preparation of Compound of Formula XI'a

Compound of Formula VIIa (100 gms) was dissolved in a mixture of toluene (500 ml) and tetrahydrofuran (250 ml) at 25-35° C. under nitrogen atmosphere. The reaction mass cooled to −68 to −78° C., n-butyl lithium (15.6 gms) was added slowly at −68 to −78° C. over 1 hr and stirred for 30 min at −78° C. After reaction completion, 2,3,4,6-tetra-O-trimethylsilyl-ß-D-glucolactone solution (126 gm of 2,3,4,6-tetra-O-trimethylsilyl-ß-D-glucolactone dissolved in 400 ml of toluene) was added slowly at −78° C. for 1.5 hr and stirred for 120 min at −78° C. To the reaction mass, pre-chilled methane sulfonic acid solution which is formed by dissolving 64.8 gm of methane sulfonic acid in 400 ml of methanol was added at −78° C. for 15 min. The temperature of the reaction mass was raised to 20° C. and stirred for 15 hrs at 20° C. the reaction mass was cooled to 0-5° C., pH adjusted to 8.0 by saturated sodium bicarbonate solution (112.0 gm of sodium bicarbonate dissolved in 1400 ml of water) at 0-5° C. The reaction mass was raised to 25-35° C., settled and separated the layers. The aqueous layer was extracted with ethyl acetate and the resulting organic layer was washed with water, 5% brine solution followed by dried over sodium sulphate. The organic layer was distilled completely under reduced pressure at below 50° C. To the residue heptanes (300 ml) was added and stirred for 1 hr. The material was filtered and dried at 50° C. to obtain title compound as pale yellow solid. Yield: 95 gms 1H NMR (300 MHz, DMSO-d6) δ=7.825-7.818 (d, 1H), 7.756-7.339 (m, 3H), 7.256-7.170 (dd, 3H) 7.022-6.849 (m, 4H), 6.827-6.696 (d, 1H), 5.505-5.490 (d, 1H), 4.802-4.545 (m, 6H), 4.016-3.947 (q, 3H), 3.746 (d, 2H), 3.593-3.520 (m, 3H), 3.398-3.183 (m) −2.970-2.489)(m, 6H), 1.332-1.170 (t, 6H); MS (ESI)[M+H]:−558

Example—16-18

Compounds of Formula XI'b, XI'c and XI'd were prepared from a compound of Formula VIIb, VIIc and VIId respectively with a compound of Formula VIIIa, analogous to procedure as described in Example 9. The results are tabulated as in Table 2:

TABLE 2

| Input | Compound VIIIa | Yield | Analysis |
|---|---|---|---|
| Formula VIIb (48 gms) | 61 gms | Formula XI'b (35 gms) | 1H NMR (300 MHz, CDCl$_3$-d6) δ = 8.076-8.041 (d, 1H), 7.399-7.338 (m, 2H), 7.261-7.161 (dd, 3H) 6.781-6.721 (m,2H), 5.084 (s, 1H), 4.811 (bs, 1H), 4.023-3.625 (m, 9H), 3.317-3.235 (q, 1H), 3.008-2.969 (d, 3H), 2.634-2.355 (m, 6H), 1.333-1.276 (t, 3H), 0.936-0.882 (t, 3H); MS (ESI)[M + H]:- 554 |
| Formula VIIc (6 gms) | 9.2 gms | Formula XI'c (3.9 gms) | 1H NMR (300 MHz, DMSO-d6) δ = 8.045-8.015 (d, 1H), 7.415-7.249 (m, 4H), 7.854-7.784 (dd, 2H), 5.000-4.763 (m, 2.321), 4.569-4.508 (t, 2H), 3.985-3.918 (dd, 2H), 3.770-3.578 (m, 7H), 3.442-3.215 (m, 5H), 2.975-2.846 (d, 3H), 2.508-2.135 (dt, 4H), 1.305-1.248 (t, 3H); MS (ESI)[M + H]:- 524 |
| Formula VIId (6 gms) | 9.2 gms | Formula XI'd (3.8 gms) | 1H NMR (300 MHz, DMSO-d6) δ = 8.02-7.966 (d, 1H), 7.385-7.213 (m,4H), 6.834-6.767 (dd, 2H), 4.998-4.737 (m, 2H), 4.571-4.506 (t, 2H), 3.970-3.939 (dd, 2H), 3.750-3.733 (dt, 3H), 3.617-3.336 (m, 4H), 3.230-2.852 (d, 3H), 2.497-2.266 (dt, 4H), 2.163-1.248 (t, 3H); MS (ESI)[M + H]:- 522 |

Example—19: Preparation of Dapagliflozin Pipecolic Acid Co-Crystals

Compound of Formula IX'a (13 gms) was added to methylene chloride (130 ml) and acetonitrile (26 ml) at 25-35° C. To the solution, triethyl silane (18.85 gms) was added at 25-35° C. and stirred for 5 min at 25-35° C. The reaction mass was cooled to −50 to −45° C. Boron trifluoride diethyl etherate (23.14 gms) was added slowly at −50 to −45° C. under nitrogen atmosphere and stirred for 15 min. The reaction mass was raised to 0-5° C. and stirred for 2 hr. pH of the reaction mass was adjusted to 7.5 using aqueous sodium bicarbonate solution. The resulting layers were separated, extracted the aqueous layer with methylene chloride and washed the resulting organic layer with brine. The methylene chloride layer was dried over sodium sulphate and concentrated under reduced pressure at 30-35° C. followed by isolating the crude compound from hexane. The crude compound was purified further on silica gel in ethyl acetate and hexanes to obtain as residue. The residue was dissolved in ethyl acetate (65 ml) at 25-35° C. and treated with pipecolic acid at 25-35° C. the reaction mass was stirred for 24 hrs at 25-35° C., filtered, washed with ethyl acetate and dried at 50° C. to obtain title compound as white solid. Yield: 3 gms

Example—20: Preparation of Dimethoxy Ethoxy Dapagliflozin Compound of Formula XIb Compound of Formula VIIa (50 gms) was dissolved in toluene (250 ml). The temperature of reaction mass was raised to 50° C. and distilled solvent completely under reduced pressure at below 50° C. Toluene (250 ml) and THF (125 ml) were added to the resulting residue at 25-35° C. The reaction mass cooled to −68 to −78° C., n-butyl lithium (84 ml) solution was added slowly at −68 to −78° C. over 15 mins and stirred for 30 min at −78° C. After reaction completion, 2,3,4,6-tetra-O-trimethylsilyl-ß-D-glucolactone solution (63 gm of 2,3,4,6-tetra-O-trimethylsilyl-ß-D-glucolactone dissolved in 200 ml of toluene) was added slowly at −78° C. for 15 mins and stirred for 90 min at −78° C. To the reaction mass, pre-chilled methane sulfonic acid solution which is formed by dissolving 32.4 gm of methane sulfonic acid in 150 ml of 2-methoxy ethanol was added at −78° C. for 15 min. The temperature of the reaction mass was raised to 20° C. and stirred for 15 hrs at 20-25° C. The reaction mass was cooled to 0-5° C., pH adjusted to 8.0 by saturated sodium bicarbonate solution (56.0 gm of sodium bicarbonate dissolved in 700 ml of water) at 0-5° C. The reaction mass was raised to 25-35° C., settled and separated the layers. The aqueous layer was extracted with ethyl acetate and the resulting organic layer was washed with water, 10% brine solution. The organic layer was distilled completely under reduced pressure at below 50° C. to obtain title compound. Yield: 42 gms.

Example 21: Characterization of Impurities of Formula B, Formula C, Formula D, Formula F, Formula G and Formula J by ¹H-NMR and Mass 1H NMR (300 MHz, DMSO-d6) δ = 7.70 (m, 1H), 7.38 (m, 1H), (7.36 (m, 1H), 7.26 (m, 1H), 7.20 (d, 2H), 6.84 (d, 2H), 5.92 (s, 2H), 3.97 (q, 2H), 1.29 (t, 3H)
Mass: ES(+ve) m/z: 245 (M + H −H$_2$O)

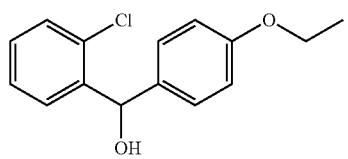

Desbromo impurity
Formula B

-continued

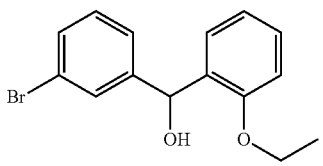

Formula C

1H NMR (300 MHz, DMSO-d6) δ = 7.48 (m, 1H), 7.45 (m, 1H), 7.35 (m, 1H), 7.34 (m, 1H), 7.23 (td, 1H), 6.94 (m, 1H), 6.92 (d, 1H), 6.20 (d, 1H), 5.90 (d, 1H) 3.94 (m, 2H), 1.22 (t, 3H)
Mass: ES(+ve) m/z: 465 (M + H − H$_2$O)

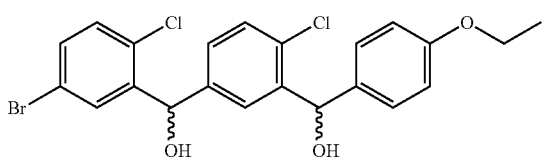

Dimer impurity
Formula D

1H NMR (300 MHz, DMSO-d6) δ = 7.78 (m, 1H), 7.75 (m, 1H), 7.50 (dd, 1H), 7.37 (dd, 1H), 7.30 (d, 1H), 7.17 (m, 1H), 7.16 (d, 2H), 6.82 (d, 2H), 6.34 (d, 1H), 5.95 (m, 2H), 5.88 (m, 1H), 3.97 (q, 2H), 1.26 (t, 3H)
Mass: ES(+ve) m/z: 465 (M + H − H$_2$O)

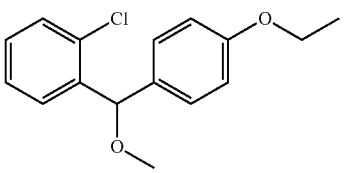

Desbromo methoxy impurity
Formula F

1H NMR (300 MHz, CDCl$_3$) δ = 7.594-7.588 (d, 1H), 7.568-7.246 (dd, 4H), 7.210-7.154 (dd, 1H), 6.847-6.818 (d, 2H), 5.614 (s, 1H), 4.027-3.957 (q, 2H), 3.366 (s, 3H), 1.402-1.356 (t, 3H).
Mass: ES(+ve) m/z: 245 (M + H − OCH$_3$)

Mass: ES(+ve) m/z: 439 (M + H − OTMS)

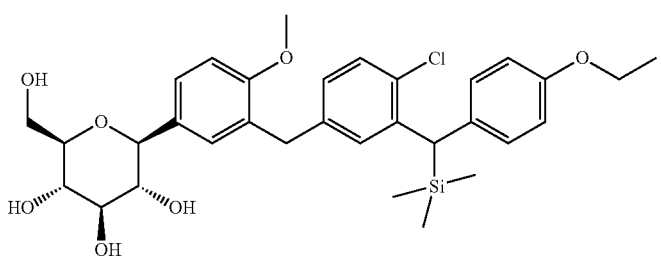

Mono methoxy monosilyl impurity
Formula G

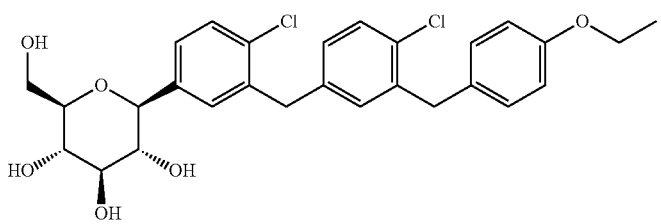

Dimer impurity
Formula J

1H NMR (300 MHz, DMSO-d6) δ = 7.386-7.227 (m, 5H), 7.086-6.998 (dd, 3H), 6.845-6.817 (d, 2H), 4.972 (t, 2H), 4.852-4.834 (d, 1H), 4.463-4.426 (t, 1H), 4.067-3.935 (m, 7H), 3.734-3.717 (m, 1H), 3.696-3.680 (m, 1H), 3.492-3.417 (m, 4H), 1.320-1.274 (t, 3H)
Mass: ES(−ve) m/z: 577 (M − H + HCOOH)

We claim:

1. A process for the preparation of dapagliflozin of Formula I or its solvates or co-crystals thereof,

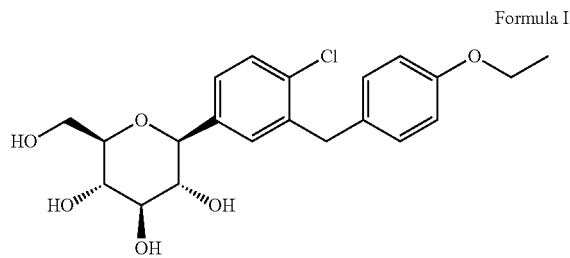 [SMILES: CCOc1ccc(Cc2cc([C@@H]3O[C@H](CO)[C@@H](O)[C@H](O)[C@H]3O)ccc2Cl)cc1]

Formula I comprising:
a) (i) reacting a compound of Formula VI with a leaving group source to form a compound of Formula VIa', (ii) reacting the compound of Formula VIa' with an amine source in the presence of a base and a solvent to obtain a compound of Formula VII,

Formula VI

Formula VIa'

Formula VII wherein $X_1$ and Lg each independently represent a leaving group; and R1 and R2 independently represent hydrogen, a linear or branched alkyl group, a linear or branched alkenyl group, a cycloalkyl group, a substituted or unsubstituted aryl group, or a substituted or unsubstituted aralkyl group, or R1 and R2 together with the nitrogen atom to which they are attached form a heterocyclic ring;

b) condensing the compound of Formula VII with a glucono lactone of Formula VIII in the presence of a base and a solvent to obtain a compound of Formula IX',

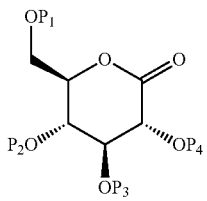

Formula VIII

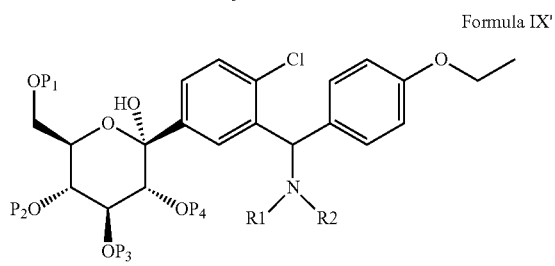

Formula IX' wherein R1 and R2 are as defined above and wherein $P_1$, $P_2$, $P_3$ and $P_4$ each independently represent a hydroxyl protecting group;

c) converting the compound of Formula IX' to a compound of Formula XI' with a glycosidation reagent in the presence of methanol,

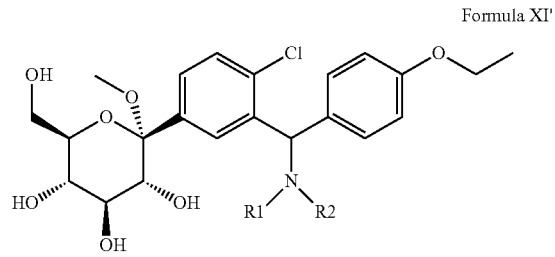

Formula XI' wherein $P_1$, $P_2$, $P_3$, $P_4$, R1, and R2 are as defined above; and d) reducing the compound of Formula XI' using a reducing agent to obtain the dapagliflozin of Formula I; and e) optionally, adding a solvent to the dapagliflozin of Formula I to obtain a solvate thereof, or adding a co-crystal former to form a co-crystal thereof.

2. The process of claim 1, wherein $X_1$ represents one of fluoro, chloro, bromo or iodo, and wherein the hydroxyl protecting group is selected from the group consisting of alkyl, allyl, pivaloyl, acetyl, tosyl, mesyl, trimethylsilyl, triethylsilyl, triisopropylsilyl, tertiary butyldimethylsilyl, 2-(trimethylsilyl) ethoxymethyl, benzyl, para-methoxybenzyl, trityl, para-bromobenzoyl, para-nitrobenzoyl, benzoyl, benzyloxymethyl, p-methoxybenzyloxymethyl, [(3,4-dimethoxybenzyl)oxy]methyl, methoxymethyl, 2-methoxyethoxymethyl and methylthiomethyl.

3. The process of claim 1, wherein the leaving group source is selected from the group consisting of phosgene, oxalyl chloride, thionyl chloride, phosphorus oxychloride, phosphorous trichloride, phosphorus pentachloride, carbonyl dibromide, oxalyl bromide, thionyl bromide, phosphorous bromide, phosphorus oxybromide, methanesulfonic acid, benzenesulfonic acid, p-toluenesulfonic acid, trifluoromethane sulfonic acid, methanesulfonyl chloride, p-toluenesulfonyl chloride, trifluoromethane sulfonyl chloride, benzene sulfonyl chloride, methanesulfonic anhydride, p-toluenesulfonic anhydride, and trifluoromethanesulfonic anhydride.

4. The process of claim 3, wherein the leaving group source is methanesulfonyl chloride.

5. The process of claim 1, wherein the amine source is selected from the group consisting of diethylamine, diisopropylamine, di-n-propylamine, diallylamine, N-ethyl-N-phenylamine, diphenylamine, dibenzylamine, dicyclopropylamine, dicyclohexylamine, morpholine, piperidine, and pyrrolidine.

6. The process of claim 1, wherein in step a) the base is selected from one or more of the group consisting of lithium hydroxide, sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, isopropyl ethylamine, diisopropyl amine, diisopropyl ethylamine, N-methyl morpholine, pyridine, and mixtures thereof.

7. The process of claim 1, wherein the solvent selected from one or more of the group consisting of nitriles selected from acetonitrile or propionitrile; ethers selected from tetrahydrofuran, dimethyl ether, diisopropyl ether, methyl tertiary butyl ether, or 1,4-dioxane; halogenated hydrocarbons selected from methylene chloride, ethylene chloride, or chloroform; sulfoxides selected from dimethylsulfoxide or diethyl sulfoxide; ketones selected from acetone, methyl isobutyl ketone, or methyl ethyl ketone; amides selected from dimethyl formamide, dimethyl acetamide, or N-methyl pyrrolidinone; and mixtures thereof.

8. The process of claim 1, wherein in step a) the amine source is one of diethylamine, N-ethyl-N-phenylamine, diphenylamine, morpholine or piperidine, wherein the base is potassium carbonate, and wherein the solvent is acetonitrile.

9. The process of claim 1, wherein in step b) the base is selected from the group consisting of n-butyl lithium, sec-butyl lithium, tert-butyllithium, sodium hydride, potassium hydride, isopropylmagnesium chloride-lithium chloride complex, sec-butylmagnesium chloride lithium chloride complex, and (trimethylsilyl) methyl lithium.

10. The process of claim 1, wherein in step b) the solvent is an ether, an aromatic hydrocarbon, or a mixture thereof.

11. The process of claim 1, wherein in step b) the base is n-butyl lithium and the solvent is a mixture of toluene and tetrahydrofuran.

12. The process of claim 1, wherein the glycosidation reagent is selected from the group consisting of an organic acid selected from formic acid, acetic acid, trifluoroacetic acid, methanesulfonic acid, oxalic acid, or p-toluene sulfonic acid; an inorganic acid selected from hydrochloric acid, sulfuric acid, or nitric acid; and a Lewis acid selected from boron trifluoride diethyletherate, scandium (III) trifluoromethanesulfonate, titanium (IV) isopropoxide, tin (IV) chloride, zinc (II) bromide, or zinc (II) chloride.

13. The process of claim 1, wherein the glycosidation reagent is one of methane sulfonic acid or hydrochloric acid.

14. The process of claim 1, wherein in step d) the reduction reaction is carried out with a reducing agent optionally in the presence of a Lewis or Brønsted acid in a solvent.

15. The process of claim 14, wherein the reducing agent is selected from the group consisting of triethyl silane, tripropyl silane, triisopropyl silane, and diphenylsilane, wherein the Brønsted acid is selected form the group consisting of hydrochloric acid, toluenesulphonic acid, trifluoroacetic acid, and acetic acid; and wherein the Lewis acid is selected from the group consisting of boron trifluoride diethyl etherate, trimethylsilyltriflate, titanium tetrachloride, tin tetrachloride, scandium triflate, and zinc iodide.

16. The process of claim 1, wherein the reduction is carried out using triethyl silane and boron trifluoride diethyl etherate.

17. A compound of Formula VII,

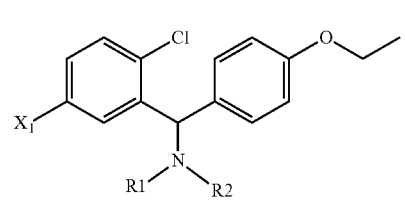

Formula VII wherein $X_1$ represents a leaving group; and

R1 and R2 each independently represents a linear or branched alkyl group, a linear or branched alkenyl group, a cycloalkyl group, a substituted or unsubstituted aryl group, or a substituted or unsubstituted aralkyl group or R1 and R2 together with the nitrogen atom to which they are attached form a heterocyclic ring.

18. The compound of claim 17, wherein the compound of Formula VII is (i) a compound of Formula VIIa,

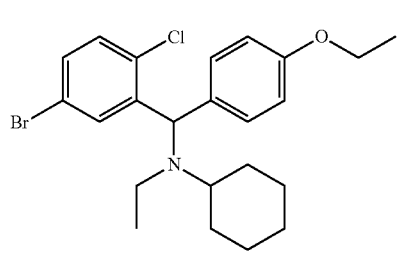

Formula VIIa (ii) a compound of Formula VIIb,

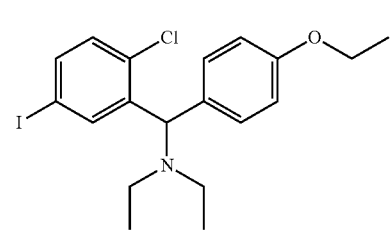

Formula VIIb (iii) a compound of Formula VIIc,

Formula VIIc

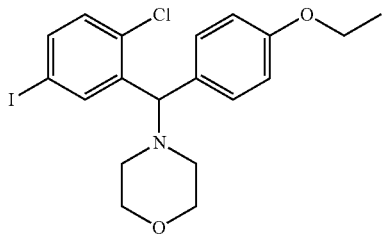

(iv) a compound of Formula VIId,

Formula VIId

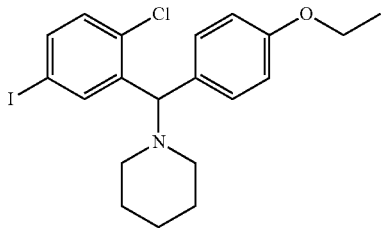

or
(v) a compound of Formula VIIe,

Formula VIIe

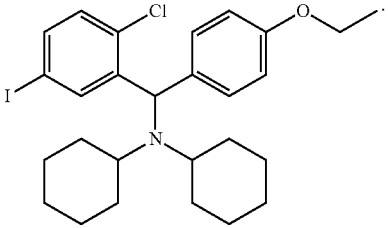

19. A compound of Formula IX',

Formula IX'

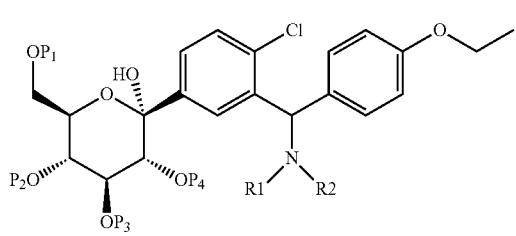

wherein R1 and R2 independently represents hydrogen, a linear or branched alkyl group, a linear or branched alkenyl group, a cycloalkyl group, a substituted or unsubstituted aryl group, or a substituted or unsubstituted aralkyl group, or R1 and R2 together with the nitrogen atom to which they are attached form a heterocyclic ring; and wherein $P_1$, $P_2$, $P_3$ and $P_4$ independently represents a hydroxyl protecting group.

20. The compound of claim 19, wherein the compound of Formula IX' is (i) a compound of Formula IX'a, Formula IX'a

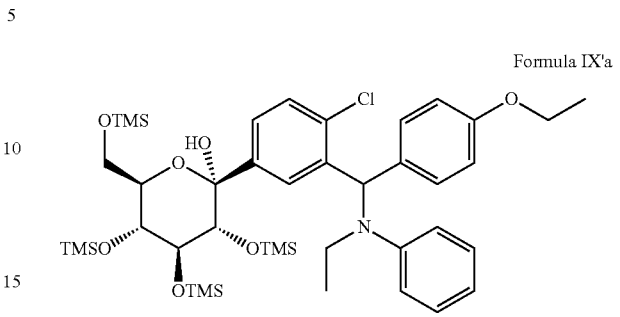

(ii) a compound of Formula IX'b,

Formula IX'b

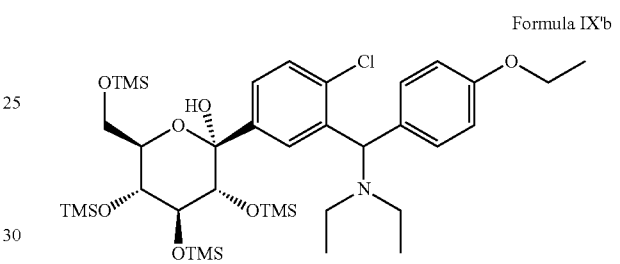

(iii) a compound of Formula IX'c,

Formula IX'c

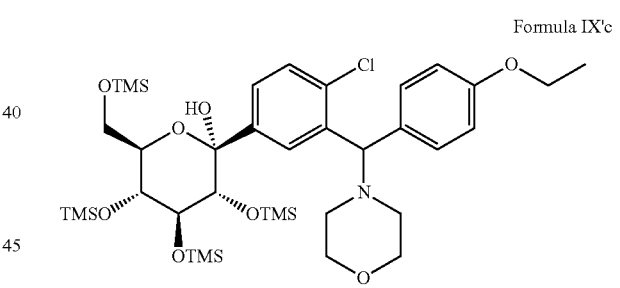

or
(iv) a compound of Formula IX'd,

Formula IX'd

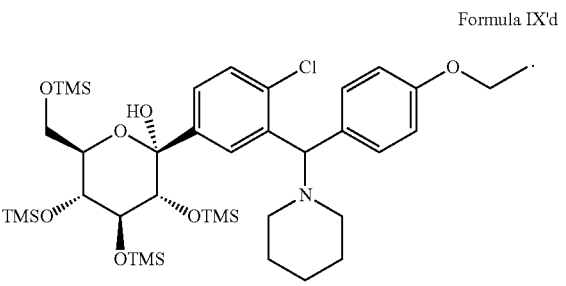

21. A compound of Formula XI'

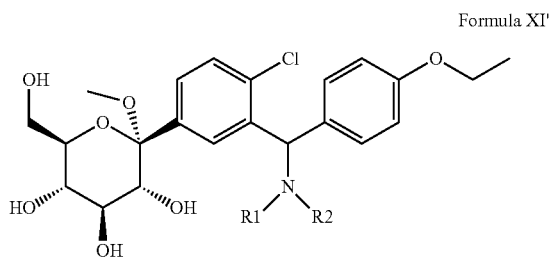

Formula XI' wherein R1 and R2 independently represents hydrogen, a linear or branched alkyl group, a linear or branched alkenyl group, a cycloalkyl group, a substituted or unsubstituted aryl group, or a substituted or unsubstituted aralkyl group, or R1 and R2 together with the nitrogen atom to which they are attached form a heterocyclic ring.

22. The compound of claim 21, wherein the compound of Formula XI' is
(i) a compound of Formula XI'a,

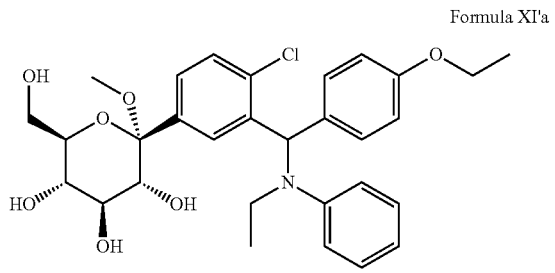 [SMILES: CCOc1ccc(C(c2cc([C@]3(OC)O[C@H](CO)[C@@H](O)[C@H](O)[C@H]3O)ccc2Cl)N(CC)c2ccccc2)cc1]

Formula XI'a (ii) a compound of Formula XI'b,

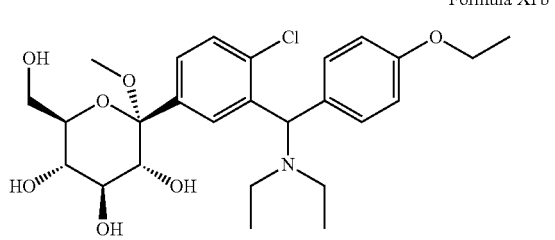

Formula XI'b (iii) a compound of Formula XI'c,

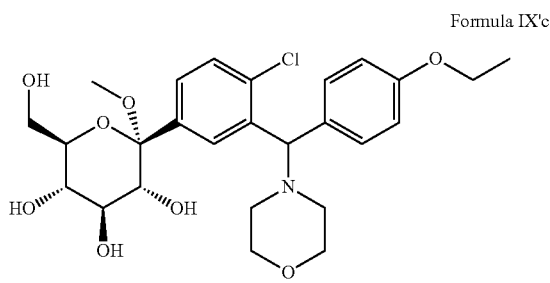 [SMILES: CCOc1ccc(C(c2cc([C@]3(OC)O[C@H](CO)[C@@H](O)[C@H](O)[C@H]3O)ccc2Cl)N2CCOCC2)cc1]

Formula IX'c or
(iv) a compound of Formula XI'd,

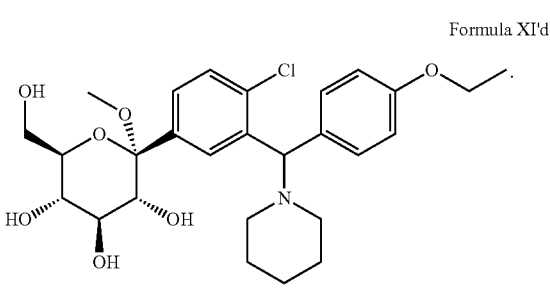 [SMILES: CCOc1ccc(C(c2cc([C@]3(OC)O[C@H](CO)[C@@H](O)[C@H](O)[C@H]3O)ccc2Cl)N2CCCCC2)cc1]

Formula XI'd

23. A process for preparing a pharmaceutical formulation of dapagliflozin or a solvate or co-crystal thereof comprising:
a) the process for the preparation of dapagliflozin or a solvate or co-crystal thereof of claim 1; and
b) preparing a pharmaceutical formulation comprising the dapagliflozin or solvate or cocrystal thereof, and at least one pharmaceutically acceptable excipient.

* * * * *